(12) United States Patent
Gong et al.

(10) Patent No.: US 7,960,427 B2
(45) Date of Patent: Jun. 14, 2011

(54) 5-HYDROXYINDOLE-3-CARBOXYLATE DERIVATIVES AND USES THEREOF

(75) Inventors: Ping Gong, Liaoning (CN); Yanfang Zhao, Liaoning (CN)

(73) Assignee: Shenyang Pharmaceutical University, Shenyang (CN)

( * ) Notice: Subject to any disclaimer, the term of this patent is extended or adjusted under 35 U.S.C. 154(b) by 660 days.

(21) Appl. No.: 10/592,619

(22) PCT Filed: Mar. 11, 2005

(86) PCT No.: PCT/CN2005/000301
§ 371 (c)(1),
(2), (4) Date: Sep. 11, 2006

(87) PCT Pub. No.: WO2005/087729
PCT Pub. Date: Sep. 22, 2005

(65) Prior Publication Data
US 2008/0249155 A1      Oct. 9, 2008

(30) Foreign Application Priority Data

Mar. 12, 2004 (CN) .......................... 2004 1 0021364

(51) Int. Cl.
*A61K 31/40* (2006.01)
*C07D 209/42* (2006.01)
(52) U.S. Cl. ........................................ 514/419; 548/492
(58) Field of Classification Search .................. None
See application file for complete search history.

(56) References Cited

U.S. PATENT DOCUMENTS
5,198,552 A  3/1993  Trofimov et al.

FOREIGN PATENT DOCUMENTS
| SU | 1685933 A1 | 10/1991 |
| WO | WO 90/08135 | 6/1990 |
| WO | WO 02/072549 A1 | 9/2002 |

OTHER PUBLICATIONS

STN Registry No. 25901-02-4 (entered Nov. 16, 1984).*
Han (Advances in Characterization of Pharmaceutical Hydrates. Trends in Bio/Pharmaceutical Industry, pp. 25-29. Mar. 2006).*
Vippagunta et al (Adv Drug Deliv Rev 48:3-26, 2001).*
Trofimov et al (Khimiko-Farmatsevticheskii Zhurnal 3(11):25-29, 1969) as evidenced by the attached STN Report (Accession No. 1970:90181).*
STN Report (Accession No. 1993:661973—containing Trofimov et al (Khimiko-Farmatsevticheskii Zhurnal 27(5):23-24, 1993)).*
Williams et al (Foye's Principles of Medicinal Chemistry, pp. 59-61, 2002).*
Patani et al (Chem Rev 96:3147-3176, 1996).*
Fadeeva, N. et al. (1993) "Inhibitors of the early stages of virus-cell interactions among derivatives of 3-ethoxycarbonyl-5-hydroxy-6-bromoindole" Khimiko-farmasevticheskii Zhurnal 26:17-20.

Grinev, A. et al. (1987) "Synthesis and antiviral activity of 2-alkylaminomethyl derivatives of 5-oxyindole" Khimiko-farmasevticheskii Zhurnal 21:52-55.
Mezentseva, M. et al. (1991) "Synthesis and antiviral activity of 2-phenoxymethyl derivatives of 5-hydroxyindole" Khimiko-farmasevticheskii Zhurnal 25:35-37.
Mezentseva, M. et al. (1991) "Synthesis and antiviral activity of 2-anilinomethyl derivatives of 5-hydroxyindole" Khimiko-farmasevticheskii Zhurnal 24:52-53.
Panisheva, E. et al. (1988) "Synthesis and biological activity of 5-oxy-6-bromoindole substitutes" Khimiko-farmasevticheskii Zhurnal 22:565-569.
Wang, D. et al. (2004) "Synthesis and in vitro antiviral activities of some new 2-arylthiomethyl-4-tertiaryaminomethylsubstituted derivatives of 6-bromo-3-ethoxycarbonyl-5-hydroxyindoles" Chinese Chemical Letters 15:19-22.
Zotova, S. et al (1995) "Synthesis and antiviral activity of indole and benzofuran sulfides" Pharmaceutical Chemistry Journal 29:57-59.
Zotova, S. et al. (1992) "Synthesis and biological activity of substituted sulfides of indole and benzofuran" Khimiko-farmasevticheskii Zhurnal 26:52-55.
Bean, P. 2005 "New Drug Targets for HIV" *Clinical Infectious Diseases* 41:S96-100.
Casiday, R. et al. 1998 "Drug Strategies to Target HIV: Enzyme Kinetics and Enzyme Inhibitors, Chemical Kinetics Experiment" retrieved from http://www.chemistry.wustl.edu/~edudev/LabTutorials/HIV/DrugStrategies.html.

(Continued)

*Primary Examiner* — Brandon J Fetterolf
*Assistant Examiner* — Craig Ricci
(74) *Attorney, Agent, or Firm* — Knobbe Martens Olson & Bear LLP

(57) ABSTRACT

The present invention relates to 5-hydroxy-indole-3-carboxylate derivatives of formula I, or racemic mixture or optical isomers or pharmaceutically acceptable salts and/or hydrates thereof,

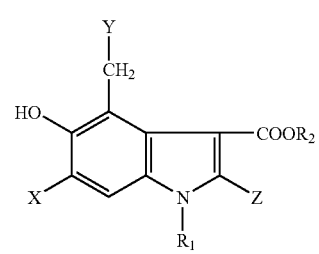

I wherein: substituents $R_1$, $R_2$, Z, X and Y are as defined in the description. The compounds of formula I can be useful for preparation of medicament for treatment and/or prophylaxis of virus infections, especially for preparation of medicament for anti-HBV (Hepatitis B virus) and anti-HIV (Human immunodeficiency virus).

11 Claims, No Drawings

OTHER PUBLICATIONS

Chai, H. et al. 2005 "Synthesis and in vitro anti-hepatitisu B virus activities of some ethyl 6-bromo-5-hydroxy-1$H$-indole-3-carboxylates" *Bioorganic & Medicinal Chemistry* 14:911-917.

Cianci, C. et al. 2005 "Antiviral activity and molecular mechanism of an orally active respiratory syncytial virus fusion inhibitor" *Journal of Antimicrobial Chemotherapy* 55:289-292.

Crumpacker, C.S. et al. 2002 "New anti-HSV therapeutics target the helicase-primase complex" *Nature Medicine* 8(4):327-328.

De Clercq, E. 2000 "Molecular Targets for Antiviral Agents" *Journal of Pharmacology and Experimental Therapeutics* 297:1-10.

Gariss, P.C. 2009 "Ribosomal frameshifting: An emerging drug target for HIV" *Current Opinion in Investigational Drugs* 10(2):121-128.

Ghany, M. et al. 2007 "Drug Targets and Molecular Mechanism of Drug Resistance in Chronic Hepatitis B" *Gastroenterology* 132:1574-1585.

Liuzzi, M. et al. 2005 "Inhibitors of Respiratory Syncytial Virus Replication Target Cotranscriptional mRNA Guanylylation by Viral RNA-Dependent RNA Polymerase" *Journal of Virology* 79(20):13105-13115.

Maltezou, H.C. et al. 2009 "Antiviral Agents for Influenza: Molecular Targets, Concerns of Resistance, and New Treatment Options" *Curretn Drug Targets* 10(10):1041-1048.

Richardson, J.Y. et al. 2005 "Respiratory Syncytial Virus (RSV) Infection Induces Cyclooxygenase 2: A Potential Target for RSV Therapy" *Journal of Immunology* 174:4356-4364.

Stein, L.L. et al. 2009 "Drug Targes in Hepatitisu B Virus Infection" *Infectious Disorders—Drug Targets* 9(2):105-116.

Sung, W-K. et al. "2009 Deregulated Direct Targets of the Hepatitis B Virus (HBV) Protein, HBx, Identified through Chromatin Immunoprecipitation and Expression Microarray Profiling" *Journal of Biological Chemistry* 284(33):21941-21954.

Zhao, C. et al. 2006 "Synthesis and in vitro anti-hepatitis B virus activites of some ethyl 5-hydroxy-1$H$-indole-3-carboxylates" *Bioorganic & Medicinal Chemistry* 14:2552-2558.

\* cited by examiner

5-HYDROXYINDOLE-3-CARBOXYLATE DERIVATIVES AND USES THEREOF

RELATED APPLICATIONS

This application is a U.S. National Phase of International application No.: PCT/CN2005/000301, filed Mar. 11, 2005, designating the U.S. and published not in English on Sep. 22, 2005 as WO 2005/087729, which claims the benefit of Chinese application No.: 200410021364.4, filed Mar. 12, 2004.

FIELD OF THE INVENTION

The present invention relates to a new series of 5-hydroxyindole-3-carboxylate derivatives, a pharmaceutical composition comprising the 5-hydroxyindole-3-carboxylate derivative as an effective constituent, their uses in the preparation of medicament for the treatment and/or prophylaxis of virus infection, especially Hepatitis B virus (HBV) infection and Human immunodeficiency virus (HIV) infection.

BACKGROUND OF THE INVENTION

Virus infection can lead to many diseases which are severely harmful to the health and life of the human being. Today, more than 3000 species of viruses over the whole world have been discovered and new types of viruses are being found. According to statistics, 60%-65% epidemic infectious diseases are caused by virus infection. Because of complexity of reciprocal action between viruses and hosts, most of antiviral agents, when exerting therapeutic action, have side-effects on the human being or have lower antiviral function. This is the main reason why the antiviral drugs are developed so slowly. As for the types of existing antiviral drugs, the antiviral drugs now used in clinic are still very scarce and are far from meeting the need of preventing and curing the virus diseases. It is important to investigate new antiviral drugs which have new antiviral mechanism, potent inhibitory activity and low toxicity.

5-hydroxyindole-3-carboxylate derivatives were originally studied as a new type of anti-influenza virus drug. The literatures, such as Grinev A. H., et al. Khim-Farm Zh, 1987, 21(1), 52; Parisheva E. K. et al. Khim Farm Zh, 1988, 22(5), 565; Mezentseva M. V. et al. Khim Farm Zh, 1990, 24(10), 52; Otova S. A., et al. Khim Farm Zh, 1992, 26(1), 52; Zotova S. A. et al. Khim Farm Zh, 1995, 29(1), 51, reported the synthesis of some 5-hydroxyindole-3-carboxylate derivatives and their pharmacological activity. The experimental results show that some of them had anti-influenza virus activity and interferon-inducing and immunostimulative functions.

Ethyl 6-bromo-4-[(dimethylamino)methyl]-5-hydroxy-1-methyl-2-(phenyl-thiomethyl)-1H-indole-3-carboxylate hydrochloride monohydrate (Arbidol, PCT Int Appl. WO 9008135(RUSS), 1990-6-26), one of 5-hydroxyindole-3-carboxylates, was launched in Russia Federation by VNIKhFI Co. Ltd. in 1993 for the prophylaxis and treatment of influenza A and B and acute respiratory viral infections.

In order to develop new type of highly effective antiviral drugs, the inventor has performed extensive studies on 5-hydroxy-indole-3-carboxylate derivatives. Modifications and changes are made on several structural sites and a new series of 5-hydroxyindole-3-carboxylate derivatives are synthesized. Their antiviral activities are determined in vitro and the results showed that they had anti-influenza virus activity. Surprisingly, they are found to have potent anti-HBV and anti-HIV activities. So the compounds are studied intensively and the invention is thereby completed.

SUMMARY OF THE INVENTION

The invention is directed to 5-hydroxyindole-3-carboxylate derivatives of formula I, or racemic mixture or optical isomers or pharmaceutically acceptable salts and/or hydrates thereof,

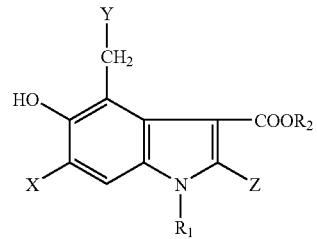

wherein:

$R_1$ is H, $C_1$-$C_6$ alkyl, or $C_3$-$C_7$ cycloalkyl, wherein said alkyl and cycloalkyl are optionally substituted with 1 to 2 substituents selected from the group consisting of hydroxyl, nitro, halo, cyano, trifluoromethyl and trifluoromethoxy;

$R_2$ is $C_1$-$C_6$ alkyl, wherein the alkyl is optionally substituted with 1 to 2 substituents selected from the group consisting of hydroxyl, nitro, halo, cyano, trifluoromethyl and trifluoromethoxy;

X is H, nitro, halo, cyano, trifluoromethyl or trifluoromethoxy;

Y is —$NR_3R_4$;

Z is —$CH_2$—S—$R_5$,

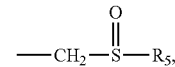

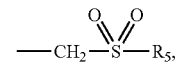

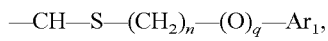

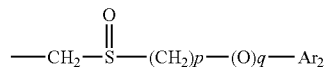

and

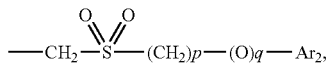

wherein n and p represent the integer from 0 to 4, q represents the integer 0 or 1. When both n and p are 0, q is 0. When both n and p represent the integer from 1 to 4, q represents the integer 0 or 1;

$R_3$ and $R_4$, which are same or different, are selected independently from the group consisting of H, amino, $C_1$-$C_{10}$ alkyl, $C_3$-$C_7$ cycloalkyl, $C_2$-$C_{10}$ alkenyl and $C_2$-$C_{10}$ alkynyl, wherein said alkyl, cycloalkyl, alkenyl and alkynyl are optionally substituted by 1 to 3 same or different $R_8$;

Or $R_3$ and $R_4$ are covalently bonded together with the nitrogen atom to which they are attached to form guanidyl, 5- to 10-membered heterocyclic radical or 5- to 10-membered heteroaryl radical. Except the nitrogen atom to which $R_3$ and $R_4$ are attached, said heterocyclic and heteraryl radicals may have optionally 1 to 4 heteroatoms selected from N, O or S. Except the nitrogen atom to which $R_3$ and $R_4$ are attached, said heterocyclic radical may optionally have 1 to 2 carbon-carbon double bond or triple bond. Said heterocyclic and heteroaryl radicals can be optionally substituted with 1 to 3 same or different $R_8$;

$R_5$ is $C_1$-$C_{10}$ alkyl, $C_3$-$C_{10}$ cycloalkyl, $C_2$-$C_{10}$ alkenyl, or $C_2$-$C_{10}$ alkynyl, which can be optionally substituted with 1 to 3 same or different $R_9$;

When n is 0, $Ar_1$ represents 5- to 10-membered heteroaryl radical having 2 to 3 heteroatoms selected from N, O or S and $Ar_1$ can be optionally substituted with 1 to 3 same or different $R_9$;

When n is the integer from 1 to 4, $Ar_1$ represents $C_6$-$C_{10}$ aryl, 5- to 10-membered heteroaryl radical or 5- to 10-membered heterocyclic radical, wherein said heteroaryl and heterocyclic radicals can have 1 to 3 heteroatom selected from N, O or S and $Ar_1$ can be optionally substituted with 1 to 3 same or different $R_9$;

$Ar_2$ represents $C_6$-$C_{10}$ aryl, 5- to 10-membered heteroaryl radical or 5- to 10-membered heterocyclic radical, wherein said heteroaryl and heterocyclic radicals can have 1 to 3 heteroatoms selected from N, O or S and $Ar_2$ can be optionally substituted with 1 to 3 same or different $R_9$;

$R_8$ represents $C_1$-$C_4$ alkyl, $C_1$-$C_4$ alkoxyl, halo, hydroxyl, cyano, carboxyl, ester group or nitro;

$R_9$ represents $C_1$-$C_6$ alkyl, $C_1$-$C_6$ alkoxyl, hydroxyl, $C_1$-$C_6$ alkyl or $C_1$-$C_6$ alkoxyl which is optionally substituted with hydroxyl, amino or halo, $C_1$-$C_6$ alkylsulfanyl, carboxyl group which can be free or form ester group, amide, or salts, halo, $C_1$-$C_6$ alkylacyl, nitro, cyano, amino, $C_1$-$C_6$ alkylamide group, or amine group substituted with ($C_1$-$C_6$ alkyl)$_n$, where n is 1 or 2;

provided that:
When Z is —$CH_2SR_5$, Y is —$N(CH_3)_2$, $R_1$ is methyl, $R_2$ is ethyl and when X is bromo, $R_5$ is not cyclohexyl;

When Z is —$CH_2$—S—$(CH_2)_n$—$(O)_q$—$Ar_1$, wherein n is 0 and q is 0, Y is —N $(CH_3)_2$, $R_1$ is methyl, $R_2$ is ethyl and when X is bromo, $Ar_1$ is not 2-benzol[d]thiazolyl.

When Z is —$CH_2$—S—$(CH_2)_n$—$(O)_q$—$Ar_1$, wherein n is 1 and q is 0, Y is —N $(CH_3)_2$, $R_1$ is methyl, $R_2$ is ethyl and when X is bromo, $Ar_1$ is not phenyl;

When Z is

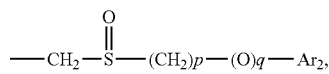

wherein p is 0 and q is 0, Y is —N $(CH_3)_2$, $R_1$ is methyl, $R_2$ is ethyl and when X is bromo, $Ar_2$ is not phenyl.

The invention also relates to the compound of formula I, or racemic mixture or optical isomers or pharmaceutically acceptable salts and/or hydrates thereof, wherein:
$R_1$ is H, $C_1$-$C_6$ alkyl or $C_3$-$C_7$ cycloalkyl;
$R_2$ is $C_1$-$C_6$ alkyl;
X is H, or halo;
Y is —$NR_3R_4$;
Z is

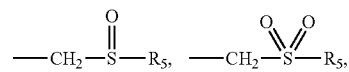

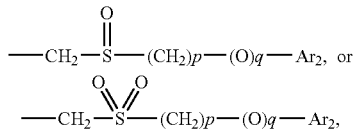

wherein n and p represent the integer from 0 to 4, q represents the integer 0 or 1. When both n and p are 0, q is 0. When both n and p represent the integer from 1 to 4, q represents the integer 0 or 1;

$R_3$ and $R_4$, which may be same or different, are selected independently from H, $C_1$-$C_{10}$ alkyl, $C_3$-$C_7$ cycloalkyl, which can be optionally substituted by 1 to 3 same or different $R_8$;

Or $R_3$ and $R_4$ are covalently bonded together with the nitrogen atom to which they are attached to form guanidyl, 5- to 10-membered heterocyclic radical or 5- to 10-membered heteroaryl radical. Except the nitrogen atom to which $R_3$ and $R_4$ are attached, said heterocyclic and heteraryl radicals may have optionally 1 to 4 heteroatoms selected from N, O or S. Said heterocyclic and heteroaryl radicals can be optionally substituted with 1 to 3 same or different $R_8$;

$R_5$ is $C_1$-$C_{10}$ alkyl, $C_3$-$C_{10}$ cycloalkyl, which can be optionally substituted with 1 to 3 same or different $R_8$;

When n is 0, $Ar_1$ represents 5- to 10-membered heteroaryl radical having 2 heteroatoms selected from N, O or S and $Ar_1$ can be optionally substituted with 1 to 3 same or different $R_9$;

When n is the integer from 1 to 4, $Ar_1$ represents $C_6$-$C_{10}$ aryl or $C_5$-$C_{10}$ heteroaryl radical, wherein said heteroaryl radical can have 1 to 3 heteroatoms selected from N, O or S, and $Ar_1$ can be optionally substituted with 1 to 3 same or different $R_9$;

$Ar_2$ represents $C_6$-$C_{10}$ aryl or 5- to 10-membered heteroaryl radical, wherein said heteroaryl radical can contain 1 to 3 heteroatom(s) selected from N, O or S and $Ar_2$ can be optionally substituted with 1 to 3 same or different $R_9$.

In a preferred embodiment, the invention relates to the compound of formula I or racemic mixture or optical isomers or pharmaceutically-acceptable salts and/or hydrates thereof, wherein:
$R_1$ is H, $C_1$-$C_4$ alkyl or $C_3$-$C_7$ cycloalkyl;
$R_2$ is $C_1$-$C_4$ alkyl;
X is H, or halo;
Y is —$NR_3R_4$;
Z is —$CH_2$—S—$(CH_2)_n$—$(O)_q$—$Ar_1$,

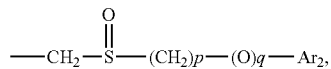

or $$-CH_2-\overset{O}{\underset{\parallel}{\underset{\parallel}{S}}}-(CH_2)_p-(O)_q-Ar_2,$$

wherein n represents the integer from 1 to 4, p represents the integer from 0 to 4, and q represents the integer 0 or 1. When p is 0, q is 0;

$R_3$ and $R_4$, which may be same or different, independently stand for $C_1$-$C_6$ alkyl, or $C_3$-$C_7$ cycloalkyl, which can be substituted by 1 to 3 same or different $R_8$;

Or $R_3$ and $R_4$ are covalently bonded together with the nitrogen to which they are attached to form guanidyl, 5- to 10-membered heterocyclic radical or 5- to 10-membered heteroaryl radical. Except the nitrogen atom to which $R_3$ and $R_4$ are attached said heterocyclic and heteroaryl radicals may have optionally 1 to 4 heteroatoms selected from N, O or S. Said heterocyclic and heteroaryl radicals can be optionally substituted with 1 to 3 same or different $R_8$;

$Ar_1$ and $Ar_2$ represent $C_6$-$C_{10}$ aryl or $C_5$-$C_{10}$ heteroaryl, wherein the heteroaryl may contain 1 to 2 heteroatom(s) selected from N, O or S and $Ar_1$ and $Ar_2$ can be optionally substituted with 1 to 3 same or different $R_9$.

In another preferred embodiment, the invention relates to the compound of formula I or racemic mixture or optical isomers or pharmaceutically-acceptable salts and/or hydrates thereof, wherein:

$R_1$ is $C_1$-$C_4$ alkyl or $C_3$-$C_7$ cycloalkyl;
$R_2$ is $C_1$-$C_4$ alkyl;
X is H, or halo;
Y is —$NR_3R_4$;
Z is —$CH_2$—S—$(CH_2)_n$—$(O)_q$—$Ar_1$, $$-CH_2-\overset{O}{\underset{\parallel}{S}}-(CH_2)_p-(O)_q-Ar_2,$$

or $$-CH_2-\overset{O}{\underset{\parallel}{\underset{\parallel}{S}}}-(CH_2)_p-(O)_q-Ar_2,$$

wherein n represents the integer from 1 to 4, p represents the integer from 0 to 4, q represents the integer 0 or 1, and when p is 0, q is 0;

$R_3$ and $R_4$, which may be same or different, independently stand for $C_1$-$C_6$ alkyl, or $C_3$-$C_7$ cycloalkyl;

Or $R_3$ and $R_4$ are covalently bonded together with the nitrogen to which they are attached to form guanidyl, 5- to 6-membered heterocyclic radical or 5- to 6-membered heteroaryl radical. Except the nitrogen atom to which $R_3$ and $R_4$ are attached, said heterocyclic and heteroaryl radicals may have optionally 1 to 4 heteroatoms selected from N, O or S. Said heterocyclic and heteroaryl radicals can be optionally substituted with 1 to 3 same or different $R_8$;

$Ar_1$ and $Ar_2$ represent phenyl, substituted phenyl or 5- to 6-membered heteroaryl. Said heteroaryl radical may have 1 to 2 heteroatoms selected from N, O or S and $Ar_1$ and $Ar_2$ can be optionally substituted with 1 to 3 same or different $R_9$.

In a particularly preferred embodiment, the invention relates to the compound of formula I or racemic mixture Qr optical isomers or pharmaceutically-acceptable salts and/or hydrates thereof, wherein:

$R_1$ is methyl, ethyl, propyl, isopropyl, or cyclopropyl;
$R_2$ is $C_1$-$C_4$ alkyl;
X is H, or halo;
Y is —$NR_3R_4$;
Z is $$-CH_2-\overset{O}{\underset{\parallel}{S}}-(CH_2)_p-(O)_q-Ar_2$$

or $$-CH_2-\overset{O}{\underset{\parallel}{\underset{\parallel}{S}}}-(CH_2)_p-(O)_q-Ar_2.$$

p represents the integer from 1 to 2. q represents the integer 0 or 1. When p is 0, q is 0;

$R_3$ and $R_4$, which may be same or different, independently stand for $C_1$-$C_6$ alkyl, or $C_3$-$C_7$ cycloalkyl;

Or $R_3$ and $R_4$ are covalently bonded together with the nitrogen to which they are attached to form guanidyl, 4-morpholino, 4-methyl-1-piperazinyl, 1-piperidino, 1-pyrrolidinyl, 1H-1,2,4-triazol-1-yl, 1-imidazolyl, 2-methyl-1-imidazolyl or 1H-tetrazol-1-yl;

$Ar_2$ represents phenyl, substituted phenyl or 5- to 6-membered heteroaryl, wherein the heteroaryl may contain 1 to 2 heteroatoms selected from N, O or S and $Ar_2$ can be optionally substituted with 1 to 3 same or different $R_9$;

In a particularly preferred embodiment, the invention relates to the compound of formula I or racemic mixture or optical isomers or pharmaceutically acceptable salts and/or hydrates thereof, wherein:

$R_1$ is methyl, ethyl, propyl, isopropyl, or cyclopropyl;
$R_2$ is $C_1$-$C_4$ alkyl;
X is H, or halo;
Y is —$NR_3R_4$;
Z is $$-CH_2-\overset{O}{\underset{\parallel}{S}}-(CH_2)_p-(O)_q-Ar_2$$

or $$-CH_2-\overset{O}{\underset{\parallel}{\underset{\parallel}{S}}}-(CH_2)_p-(O)_q-Ar_2.$$

p represents the integer from 0 to 2. q represents the integer 0;

$R_3$ and $R_4$, which may be same or different, independently stand for $C_1$-$C_4$ alkyl;

Or $R_3$ and $R_4$ are covalently bonded together with the nitrogen to which they are attached to form guanidyl, 4-morpholino, 4-methyl-1-piperazinyl, 1-piperidino, 1-pyrrolidinyl, 1H-1,2,4-triazol-1-yl, 1-imidazolyl, 2-methyl-1-imidazolyl or 1H-tetrazol-1-yl;

$Ar_2$ represents phenyl or phenyl optionally substituted with 1 to 3 same or different $R_9$.

In a preferred embodiment, the invention further relates to the compound of formula I or racemic mixture or optical isomers or pharmaceutically acceptable salts and/or hydrates thereof, wherein:

Z is

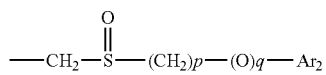

or

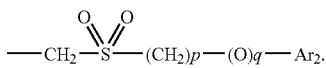

In a particularly preferred embodiment, the invention relates to the compound of formula I or racemic mixture or optical isomers or pharmaceutically acceptable salts and/or hydrates thereof, wherein:
Z is

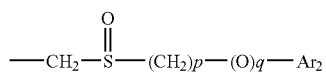

or

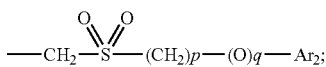

$Ar_2$ represents phenyl, substituted phenyl or 5- to 6-membered heteroaryl, wherein the heteroaryl and heterocycle radicals may contain 1 to 3 heteroatoms selected from N, O or S and $Ar_2$ can be optionally substituted with 1 to 3 same or different $R_9$. $Ar_2$ is preferably selected from phenyl or phenyl substituted by 1 to 3 halogens.

In a preferred embodiment, the invention relates to the compound of formula I or racemic mixture or optical isomers or pharmaceutically acceptable salts and/or hydrates thereof, wherein:
X is H, or bromine.

In a most preferred embodiment, the invention relates to the following compounds of formula I or racemic mixture or optical isomers or pharmaceutically acceptable salts and/or hydrates thereof:

Ethyl 2-[(benzo[d]imidazol-2-yl)thiomethyl]-6-bromo-4-[(dimethylamino)methyl]-5-hydroxy-1-methyl-1H-indole-3-carboxylate (Example 3)
Ethyl 6-bromo-4-[(dimethylamino)methyl]-2-[(4-fluorobenzyl)thiomethyl]-5-hydroxy-1-methyl-1H-indole-3-carboxylate (Example 5)
Ethyl 6-bromo-1-cyclopropyl-2-[(2-fluorobenzyl)thiomethyl]-5-hydroxy-4-[(1-pyrrolidinyl)methyl]-1H-indole-3-carboxylate (Example 14)
Ethyl 6-bromo-5-hydroxy-1-methyl-2-[(5-methoxybenzo[d]imidazol-2-yl)thiomethyl]-4-(morpholinomethyl)-1H-indole-3-carboxylate (Example 25)
Ethyl 6-bromo-1-cyclopropyl-4-[(dimethylamino)methyl]-5-hydroxy-2-[(4-thiazolylmethyl)sulfinylmethyl]-1H-indole-3-carboxylate (Example 52)
Ethyl 6-bromo-4-[(dimethylamino)methyl]-5-hydroxy-1-methyl-2-[(3-methoxyphenyl)sulfonylmethyl]-1H-indole-3-carboxylate (Example 55)
Ethyl 6-bromo-5-hydroxy-1-methyl-2-[(2-methylphenyl)sulfinylmethyl]-4-(morpholinomethyl)-1H-indole-3-carboxylate (Example 57)
Ethyl 6-bromo-2-[(4-fluorophenyl)sulfinylmethyl]-5-hydroxy-1-methyl-4-(morpholinomethyl)-1H-indole-3-carboxylate (Example 58)
Ethyl 6-bromo-2-[(3-chlorophenyl)sulfinylmethyl]-5-hydroxy-1-methyl-4-(morpholinomethyl)-1H-indole-3-carboxylate (Example 59)
Ethyl 6-bromo-5-hydroxy-1-methyl-4-(morpholinomethyl)-2-[(4-fluorobenzyl)sulfinylmethyl]-1H-indole-3-carboxylate (Example 64)
Ethyl 6-bromo-1-cyclopropyl-2-[(3,4-difluorophenyl)sulfinylmethyl]-5-hydroxy-4-[(4-methyl-1-piperazinyl)methyl]-1H-indole-3-carboxylate dihydrochloride (Example 67)
Ethyl 6-bromo-2-[(2-furylmethyl)sulfinylmethyl]-5-hydroxy-1-methyl-4-(1-pyrrolidinylmethyl)-1H-indole-3-carboxylate (Example 71)
Ethyl 5-hydroxy-2-[(3-methoxyphenyl)sulfonylmethyl]-1-methyl-4-(1-pyrrolidinylmethyl)-1H-indole-3-carboxylate (Example 72)
Ethyl 2-[(3-furylmethyl)sulfinylmethyl]-5-hydroxy-1-methyl-4-(piperidinomethyl)-1H-indole-3-carboxylate (Example 77)
Ethyl 6-bromo-1-cyclopropyl-4-[(dimethylamino)methyl]-5-hydroxy-2-[(4-trifluoromethylphenyl)sulfinylmethyl]-1H-indole-3-carboxylate (Example 79)
Ethyl 6-bromo-4-[(dimethylamino)methyl]-5-hydroxy-1-methyl-2-[(4-fluorobenzyl)sulfinylmethyl]-1H-indole-3-carboxylate (Example 80)
Ethyl 6-bromo-4-[(dimethylamino)methyl]-5-hydroxy-1-methyl-2-[(3-fluorobenzyl)sulfinylmethyl]-1H-indole-3-carboxylate (Example 81)
Ethyl 6-bromo-5-hydroxy-1-methyl-4-(1-pyrrolidinylmethyl)-2-[(4-trifluoromethylphenyl)sulfonylmethyl]-1H-indole-3-carboxylate (Example 82)
Ethyl 6-bromo-1-cyclopropyl-5-hydroxy-4-(1-pyrrolidinylmethyl)-2-[(3-trifluoromethylphenyl)sulfonylmethyl]-1H-indole-3-carboxylate (Example 83)
Ethyl 6-bromo-5-hydroxy-1-methyl-4-(1-pyrrolidinylmethyl)-2-[(4-fluorobenzyl)sulfonylmethyl]-1H-indole-3-carboxylate (Example 84)
Ethyl 1-cyclopropyl-5-hydroxy-4-(2-pyrrolidinylmethyl)-2-[(1-furylmethyl)sulfonylmethyl]-1H-indole-3-carboxylate (Example 85)
Ethyl 6-bromo-5-hydroxy-1-methyl-4-(1-piperidinomethyl)-2-[(4-fluorobenzyl)sulfinylmethyl]-1H-indole-3-carboxylate (Example 86)
Ethyl 6-bromo-2-[(3-fluorobenzyl)sulfinylmethyl]-5-hydroxy-1-methyl-4-(morpholinomethyl)-1H-indole-3-carboxylate (Example 87)
Ethyl 2-(benzylthiomethyl)-6-bromo-1-cyclopropyl-5-hydroxy-4-[(1-imidazolyl)methyl]-1H-indole-3-carboxylate (Example 91)
Ethyl 6-bromo-2-[(4-fluorobenzyl)thiomethyl]-5-hydroxy-4-[(1-imidazolyl)methyl]-1-methyl-1H-indole-3-carboxylate (Example 92)
Ethyl 6-bromo-5-hydroxy-4-[(1-imidazolyl)methyl]-1-methyl-2-[(benzo[d]imidazol-2-yl)thiomethyl]-1H-indole-3-carboxylate (Example 94)
Ethyl 6-bromo-2-[(4-fluorobenzyl)thiomethyl]-5-hydroxy-1-methyl-4-[(2-methyl-1-imidazolyl)methyl]-1H-indole-3-carboxylate (Example 100)
Ethyl 6-bromo-4-(guanidinylmethyl)-5-hydroxy-1-methyl-2-(benzylthiomethyl)-1H-indole-3-carboxylate (Example 104)
Ethyl 6-bromo-5-hydroxy-4-[(1-imidazolyl)methyl]-1-methyl-2-(phenylsulfinylmethyl)-1H-indole-3-carboxylate (Example 116)

Ethyl 6-bromo-1-cyclopropyl-5-hydroxy-4-(1-imidazolylmethyl)-2-[(4-fluorophenyl)sulfinylmethyl]-1H-indole-3-carboxylate (Example 117)

Ethyl 6-bromo-1-cyclopropyl-2-[(3,4-difluorophenyl)sulfinyl-methyl]-5-hydroxy-4-[(1-imidazolyl)methyl]-1H-indole-3-carboxylate (Example 119)

Ethyl 6-bromo-2-[(4-fluorophenyl)sulfinylmethyl]-5-hydroxy-4-[(1-imidazolyl)methyl]-1-methyl-1H-indole-3-carboxylate (Example 122)

Ethyl 6-bromo-5-hydroxy-4-[(1-imidazolyl)methyl]-1-methyl-2-[(2-fluorophenyl)sulfinylmethyl]-1H-indole-3-carboxylate (Example 125)

Ethyl 2-(benzylsulfinylmethyl)-6-bromo-1-cyclopropyl-5-hydroxy-4-[(1-imidazolyl)methyl]-1H-indole-3-carboxylate (Example 126)

Ethyl 6-bromo-1-cyclopropyl-5-hydroxy-4-[(1-imidazolyl)methyl]-2-[(4-thiazolylmethyl)sulfinyl methyl]-1H-indole-3-carboxylate (Example 128)

Ethyl 6-bromo-1-cyclopropyl-5-hydroxy-4-[(1-imidazolyl)methyl]-2-[(2-furylmethyl)sulfinylmethyl]-1H-indole-3-carboxylate (Example 130)

Ethyl 6-bromo-5-hydroxy-1-methyl-4-[(2-methyl-1-imidazolyl)methyl]-2-[(3,4-difluorophenyl)sulfinylmethyl]-1H-indole-3-carboxylate (Example 133)

Ethyl 6-bromo-5-hydroxy-1-methyl-4-[(2-methyl-1-imidazolyl)methyl]-2-[(3-methylphenyl)sulfinylmethyl]-1H-indole-3-carboxylate (Example 134)

Ethyl 6-bromo-5-hydroxy-1-methyl-4-[(2-methyl-1-imidazolyl)methyl]-2-[(2-methoxyphenyl)sulfinylmethyl]-1H-indole-3-carboxylate (Example 135)

Ethyl 6-bromo-1-cyclopropyl-2-[(2,6-dichlorophenyl)sulfinylmethyl]-5-hydroxy-4-[(2-methyl-1-imidazolyl)methyl]-1H-indole-3-carboxylate (Example 137)

Ethyl 6-bromo-1-cyclopropyl-2-[(4-fluorophenyl)sulfinylmethyl]-5-hydroxy-4-[(2-methyl-1-imidazolyl)methyl]-1H-indole-3-carboxylate (Example 138)

Ethyl 5-hydroxy-1-methyl-4-[(2-methyl-1-imidazolyl)methyl]-2-[(4-methylphenyl)sulfinylmethyl]-1H-indole-3-carboxylate (Example 142)

Ethyl 6-bromo-5-hydroxy-1-methyl-2-(phenylsulfinylmethyl)-4-[(1H-1,2,4-triazol-1-yl)methyl]-1H-indole-3-carboxylate (Example 146)

Ethyl 6-bromo-5-hydroxy-1-methyl-4-[(1H-1,2,4-triazol-1-yl)methyl]-2-[(4-fluorobenzyl)sulfinylmethyl]-1H-indole-3-carboxylate (Example 149)

Ethyl 6-bromo-4-(guanidinylmethyl)-5-hydroxy-1-methyl-2-[(2-methoxyphenyl)sulfinylmethyl]-1H-indole-3-carboxylate (Example 151)

Ethyl 6-bromo-4-(guanidinylmethyl)-5-hydroxy-1-methyl-2-[(4-methylphenyl)sulfinylmethyl]-1H-indole-3-carboxylate (Example 152)

Ethyl 6-bromo-4-(guanidinylmethyl)-5-hydroxy-1-methyl-2-[(4-fluorophenyl)sulfinylmethyl]-1H-indole-3-carboxylate (Example 153)

Ethyl 6-bromo-1-cyclopropyl-4-(guanidinylmethyl)-5-hydroxy-2-[(4-fluorophenyl)sulfinylmethyl]-1H-indole-3-carboxylate (Example 154)

Ethyl 6-bromo-4-[(2-aminoethylthio)methyl]-5-hydroxy-1-methyl-2-[(2-pyridyl)sulfinylmethyl]-1H-indole-3-carboxylate (Example 158)

Ethyl 6-bromo-1-cyclopropyl-5-hydroxy-4-[(1-imidazolyl)methyl]-2-(2-furylmethyl)sulfonylmethyl]-1H-indole-3-carboxylate (Example 162)

Ethyl 6-bromo-5-hydroxy-4-[(1-imidazolyl)methyl]-1-methyl-2-[(4-fluorobenzyl)sulfonylmethyl]-1H-indole-3-carboxylate (Example 163)

Ethyl 1-cyclopropyl-5-hydroxy-4-[(1-imidazolyl)methyl]-2-[(4-methylphenyl)sulfonylmethyl]-1H-indole-3-carboxylate (Example 164)

Ethyl 6-bromo-1-cyclopropyl-5-hydroxy-4-[(2-methyl-1-imidazolyl)methyl]-2-[(2-fluorobenzyl)sulfonylmethyl]-1H-indole-3-carboxylate (Example 165)

Ethyl 6-bromo-5-hydroxy-1-methyl-4-[(2-methyl-1-imidazolyl)methyl]-2-(phenylsulfonylmethyl)-1H-indole-3-carboxylate (Example 166)

Ethyl 6-bromo-5-hydroxy-1-methyl-4-[(2-methyl-1-imidazolyl)methyl]-2-(benzylsulfonylmethyl)-1H-indole-3-carboxylate (Example 168)

Ethyl 6-bromo-4-(guanidinylmethyl)-5-hydroxy-1-methyl-2-(benzylsulfonylmethyl)-1H-indole-3-carboxylate (Example 173)

Ethyl 6-bromo-5-hydroxy-4-[(1-imidazolyl)methyl]-1-methyl-2-(benzylthiomethyl)-1H-indole-3-carboxylate (Example 176)

Ethyl 6-bromo-5-hydroxy-4-[(1-imidazolyl)methyl]-1-methyl-2-[(4-trifluoromethylphenyl)sulfinylmethyl]-1H-indole-3-carboxylate (Example 177)

Ethyl 6-bromo-1-cyclopropyl-5-hydroxy-4-[(2-methyl-1-imidazolyl)methyl]-2-(benzylsulfonylmethyl)-1H-indole-3-carboxylate (Example 178)

Ethyl 6-bromo-5-hydroxy-1-methyl-4-[(2-methylimidazolyl)methyl]-2-[(1-adamantanyl)sulfonylmethyl]-1H-indole-3-carboxylate (Example 179)

Ethyl 6-bromo-5-hydroxy-1-methyl-4-[(2-methyl-1-imidazolyl)methyl]-2-[(4-trifluoromethylphenyl)sulfonylmethyl]-1H-indole-3-carboxylate (Example 180)

Ethyl 6-bromo-1-cyclopropyl-5-hydroxy-4-[(2-methyl-1-imidazolyl)methyl]-2-[(4-thiazolylmethyl)sulfinylmethyl]-1H-indole-3-carboxylate hydrochloride (Example 182)

Ethyl 6-bromo-1-cyclopropyl-5-hydroxy-4-[(2-methyl-1-imidazolyl)methyl]-2-[(2-fluorobenzyl)sulfinylmethyl]-1H-indole-3-carboxylate (Example 183)

Ethyl 6-bromo-5-hydroxy-1-methyl-4-[(2-methyl-1-imidazolyl)methyl]-2-[(4-fluorobenzyl)sulfinylmethyl]-1H-indole-3-carboxylate (Example 184)

Ethyl 6-bromo-5-hydroxy-1-methyl-4-[(2-methyl-1-imidazolyl)methyl]-2-[(4-fluorobenzyl)sulfonylmethyl]-1H-indole-3-carboxylate (Example 185)

Ethyl 6-bromo-1-cyclopropyl-2-[(2-fluorobenzyl)thiomethyl]-5-hydroxy-4-[(1H-1,2,4-triazol-1-yl)methyl]-1H-indole-3-carboxylate (Example 186)

Ethyl 6-bromo-5-hydroxy-1-methyl-4-[(1H-1,2,4-triazol-1-yl)methyl]-2-[(4-fluorobenzyl)thiomethyl]-1H-indole-3-carboxylate (Example 187)

Ethyl 2-(benzylthiomethyl)-6-bromo-1-cyclopropyl-4-(guanidinylmethyl)-5-hydroxy-1H-indole-3-carboxylate (Example 188)

Ethyl 2-[(benzo[d]imidazol-2-yl)thiomethyl]-6-bromo-4-(guanidinylmethyl)-5-hydroxy-1-methyl-1H-indole-3-carboxylate (Example 189).

The invention also relates to the use of the compound of formula II or racemic mixture or optical isomers or pharmaceutically acceptable salts and/or hydrates thereof in the preparation of medicament for treatment and/or prophylaxis of HBV and HIV infections:

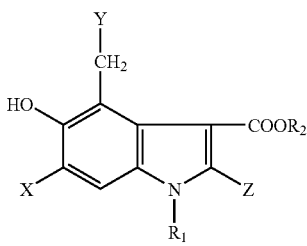

wherein:

$R_1$ is H, $C_1$-$C_6$ alkyl, $C_3$-$C_7$ cycloalkyl, wherein the alkyl and cycloalkyl can be optionally substituted by 1 or 2 groups selected from hydroxyl, nitro, halo, cyano, trifluoromethyl and trifluoromethoxy;

$R_2$ is $C_1$-$C_6$ alkyl which is optionally substituted by 1 or 2 groups selected from hydroxyl, nitro, halo, cyano, trifluoromethyl and trifluoromethoxy;

X is H, nitro, halo, cyano, trifluoromethyl or trifluoromethoxy;

Y is —$NR_3R_4$ or —$S(CH_2)_mR_8$ wherein m represents the integer from 1 to 4;

Z is —$CH_2$—S—$R_5$,

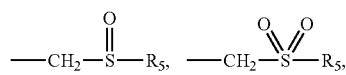

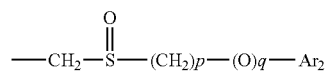

or

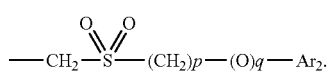

n and p represent the integer from 0 to 4. When both n and p are 0, q is 0. When both n and p represent the integer from 1 to 4, q represents the integer 0 or 1;

$R_3$ and $R_4$, which may be same or different, are selected independently from H, amino, $C_1$-$C_{10}$ alkyl, $C_3$-$C_7$ cycloalkyl, $C_2$-$C_{10}$ alkenyl, and $C_2$-$C_{10}$ alkynyl, which can be optionally substituted by 1 to 3 same or different $R_8$;

Or $R_3$ and $R_4$ are covalently bonded together with the nitrogen to which they are attached to form guanidyl, 5- to 10-membered heterocyclic radical or 5- to 10-membered heteroaryl radical. Except the nitrogen atom to which $R_3$ and $R_4$ are attached, said heterocyclic and heteraryl radicals may have optionally 1 to 4 heteroatoms selected from N, O or S. Except the nitrogen atom to which $R_3$ and $R_4$ are attached, said heterocyclic radical may optionally have 1 to 2 carbon-carbon double bond or triple bond. Said heterocyclic and heteroaryl radicals can be optionally substituted with 1 to 3 same or different $R_8$;

$R_5$ is $C_1$-$C_{10}$ alkyl, $C_3$-$C_{10}$ cycloalkyl, $C_2$-$C_{10}$ alkenyl, and $C_2$-$C_{10}$ alkynyl which can be optionally substituted with 1 to 3 same or different $R_8$;

$Ar_1$ and $Ar_2$ represent $C_6$-$C_{10}$ aryl, 5- to 10-membered heteraryl radical or 5- to 10-membered heterocyclic radical. Said heteroaryl and heterocyclic radicals can have 1 to 3 heteroatoms selected from N, O or S. $Ar_1$ and $Ar_2$ can be optionally substituted with 1 to 3 same or different $R_9$;

$R_8$ represents $C_1$-$C_4$ alkyl, $C_1$-$C_4$ alkoxy, halo, hydroxyl, cyano, carboxyl, ester group, or nitro radicals;

$R_9$ represents $C_1$-$C_6$ alkyl, $C_1$-$C_6$ alkoxy, hydroxyl, $C_1$-$C_6$ alkyl or $C_1$-$C_6$ alkoxy which is optionally substituted with hydroxyl, amino or halo, $C_1$-$C_6$ alkylthio, free carboxylic acid or salt, ester or amide thereof, halo, $C_1$-$C_6$ alkylacyl, nitro, cyano, amino, $CONH(C_1$-$C_6$ alkyl), or amine group substituted with $(C_1$-$C_6$ alkyl)$_n$, wherein n is 1 or 2.

According to several conventional methods in the art which the present invention pertains to, above 5-hydroxyindole-3-carboxylate derivatives of formula I or II can react with acids to form their pharmaceutically acceptable salts. Said acids can include inorganic and organic acids, and the pharmaceutically acceptable salts formed by using the following acids are particularly preferred: hydrochloric acid, hydrobromic acid, sulphuric acid, phosphoric acid, methanesulfonic acid, ethanesulfonic acid, toluenesulfonic acid, benzenesulfonic acid, naphthalene disulfonic acid, acetic acid, propionic acid, lactic acid, trifluoroacetic acid, maleic acid, citric acid, fumaric acid, tartaric acid, benzoic acid and p-toluene sulfonic acid.

The compounds of the present invention may contain one or more asymmetric atoms and exist in the forms of enantiomer and diastereomer. All of the compounds are included within the scope of the present invention. The racemic mixture can be separated by proper methods known per se to obtain the single ingredient.

Furthermore, the present invention includes the pro-drug of the compounds of the invention. According to the invention, the pro-drugs are the derivatives of the formula I or II, which have low biological activity or even have no biological activity, but which can be converted to the corresponding biologically-active form under the physiological condition upon administration, such as by the way of metabolism, solvent decomposition and so on.

DETAILED DESCRIPTION OF THE PREFERRED EMBODIMENT

Unless indicated otherwise, the following terms, as used herein, have the following meaning:

"halo"—all halogens, that is fluoro, chloro, bromo or indo;

"alkyl"—straight or branched chain alkyl,

"cycloalkyl"—substituted or unsubstituted cycloalkyl;

"alkenyl"—straight or branched chain alkenyl;

"alkynyl"—straight or branched chain alkynyl;

"aryl"—the organic radicals which are obtained by loss of a hydrogen of aromatic hydrocarbon, such as phenyl and naphthyl;

"5- to 10-membered heteroaryl"—an aromatic ring system of 5 to 10 atoms in which one or more rings are contained. It can have one or more heteroatoms selected from N, O or S. The examples are such as, but not limited to, imidazolyl, pyridyl, pyrimidinyl, pyrazolyl, (1,2,3)- or (1,2,4)-triazolyl, pyrazinyl, tetrazolium group, furyl, thienyl, isoxazolyl, oxazolyl, pyrazolyl, pyrrolyl, thiazolyl, benzothiophenyl, benzofuranyl, benzimidazolyl, benzothiazolyl, indolyl, quinolinyl and so on.

"5- to 10-membered heterocyclic"—a wholly or partially saturated and nonaromatic 5- to 10-membered ring system which contain one or more rings and have one or more heteroatoms selected from N, O or S, including, but not limited to, pyrrolidinyl, morpholinyl, piperazinyl, piperidyl, thiazolinyl and so on.

The certain compounds of the invention may have asymmetric centers, so they can exist in the forms of different enantiomer and diastereomer. The present invention relates to the optical isomer, racemate and racematic mixture of the compounds according to the invention. "Racemate" is defined to be a mixture of equal amount of enantiomers.

Because 5-hydroxy-indole-3-carboxylate derivatives of formula I or II according to the present invention have antiviral activity, especially anti-HBV, anti-HIV and anti influenza virus activities, they can be used to prepare the medicaments for the treatment and/or prophylaxis of virus infection, especially HBV, HIV, influenza A/B virus, respiratory syncytial virus, parainfluenze virus, rhinoviruses and adenovirus infection.

The compounds of the present invention can be used as active constitutents for treatment and prophylaxis of acquired immune deficiency syndrome, hepatitis B, acute respiratory viral infections and influenza. The present invention provides a method for the treatment or prophylaxis of above diseases, wherein a therapeutically effective amount of compound according the present invention is administrated to a patient suffering from or susceptible to the diseases.

The present invention also includes a pharmaceutical composition, which comprises 5-hydroxyindole-3-carboxylate derivatives of formula I or II or a pharmaceutically acceptable salt thereof as the active ingredient and a pharmaceutically acceptable excipient. The excipient can be any of diluents, adjuvants and/or carrier usable in pharmacology. The compounds can be combined with other active ingredients as long as they are not deleterious to the recipient thereof, such as allergic action.

The pharmaceutical composition according to the present invention can be formulated into several dosage forms, for example oral formulations (such as tablet, capsule, solution or suspension), injectable formulations (such as injectable solution or suspension, or injectable dry powder which can be reconstituted by adding water for injection immediately before use), topical formulations (such as cream or solution), and they can comprise some conventional excipients in the pharmacology art.

The formulations may conveniently be presented in unit dosage and may be prepared by any of the methods well known in the art of pharmacy. Some methods include the step of mixing the active compounds with a carrier, e.g binders, lubricants, disintegrating agents, auxiliary solvents, diluents, stabilizers, suspending agents, pigments or flavoring agents for oral preparation, preservatives (including antioxidants), diluents or stabilizers for injectable preparation, matrix, diluents, stabilizers, lubricants or preservatives (including antioxidants) for topical administration and so on. The formulations include those suitable for oral or parenteral (including subcutaneous, intraperitoneal, intravenous and topical) administration. If drugs are unstable in the condition of stomach, they can be formulated to coating tablets.

The amount of compound of formula I or II required to be effective, will, of course, be varied. The factors to be considered include the condition being treated and bioavailability, the rate of metabolism and discretion, the patient's age, sex and the period of disease. However, a suitable effective dose for an adult is in the range of about 10 to 500 mg per day, preferably in the range about 50 to 300 mg per day. Thus when considering the effective dose mentioned above, a unit of pharmaceutical preparation is in the range of about 10 to 500 mg of 5-hydroxy-indole-3-carboxylate derivatives of formula I or II defined above, preferably in the range of about 50 to 300 mg. According to the instructions of doctors or physician, the preparation can be administered several times at intervals (preferable once to six times).

The compounds of formula I or II of the present invention may be prepared by the procedures shown in Schemes A to D. As described by the schemes, all the starting materials can be purchased or prepared by the methods known to ordinary skilled artisan in organic chemistry art. All of final products in the present invention are prepared by the methods described in these schemes or similar methods. These methods are well known to those skilled in organic chemistry art. The variable factors using in the schemes can be defined as follows.

In scheme A, as for the compounds of formula I or II according to the present invention, Y is —$NR_3R_4$, wherein $R_3$ and $R_4$ which may be same or different stand for hydrogen, amino, $C_1$-$C_{10}$ alkyl, $C_3$-$C_7$ cycloalkyl, $C_2$-$C_{10}$ alkenyl and $C_2$-$C_{10}$ alkynyl, which can be substituted by 1 to 3 same or different $R_8$. Or $R_3$ and $R_4$ are covalently bonded together with the nitrogen to which they are attached to form 5- to 10-membered heterocyclic radical. Except the nitrogen atom to which $R_3$ and $R_4$ are attached, said heterocyclic radical may have optionally 1 to 4 heteroatoms selected from N, O or S. Except the nitrogen atom to which $R_3$ and $R_4$ are attached, said heterocyclic radical may optionally have 1 to 2 carbon-carbon double bond or triple bond. Said heterocyclic radical can be optionally substituted with 1 to 3 same or different $R_8$; Q is $R_5$, —$(CH_2)_n$—$(O)_q$—$Ar_1$ or —$(CH_2)_p$—$(O)_q$—$Ar_2$ n and p are the integer from 0 to 4. When n and p are both 0, q is 0. When n and p are both the integer from 1 to 4, q is 0 or 1. Substituents $R_1$, $R_2$, $R_5$, $Ar_1$ and $Ar_2$ are as defined in Summary of the invention.

The key intermediate 1-alkyl-5-hydroxy-2-methyl-1H-indole-3-carboxylate (A-2) is synthesized from commercially available acetoacetic ester and ammonia or an appropriate amine substituted by $R_1$, followed by Nentizescu condensation of 3-substituted amino-2-crotonate (A-1) and 1,4-benzoquinone refluxing in the 1,2-dichloroethane. Acetyl chloride is added to the solution of A-2 and pyridine to give 5-acetoxy-1-alkyl-2-methyl-1H-indole-3-carboxylate (A-3). In the presence of catalyst (benzoylperoxide), A-3 is refluxing with bromine in tetrachloromethane to gives A-4 (1-alkyl-5-acetoxy-6-bromo-2-bromomethyl-1H-indole-3-carboxylate), which is then substituted with appropriate QISH under the basic condition to give A-5. A-5 reacts with formaldehyde and $R_3R_4NH$ to give A-6 of formula I or II (Mannich reaction).

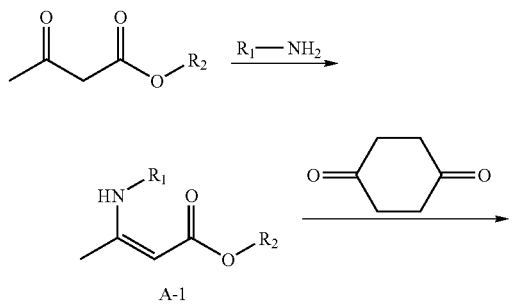

Scheme A

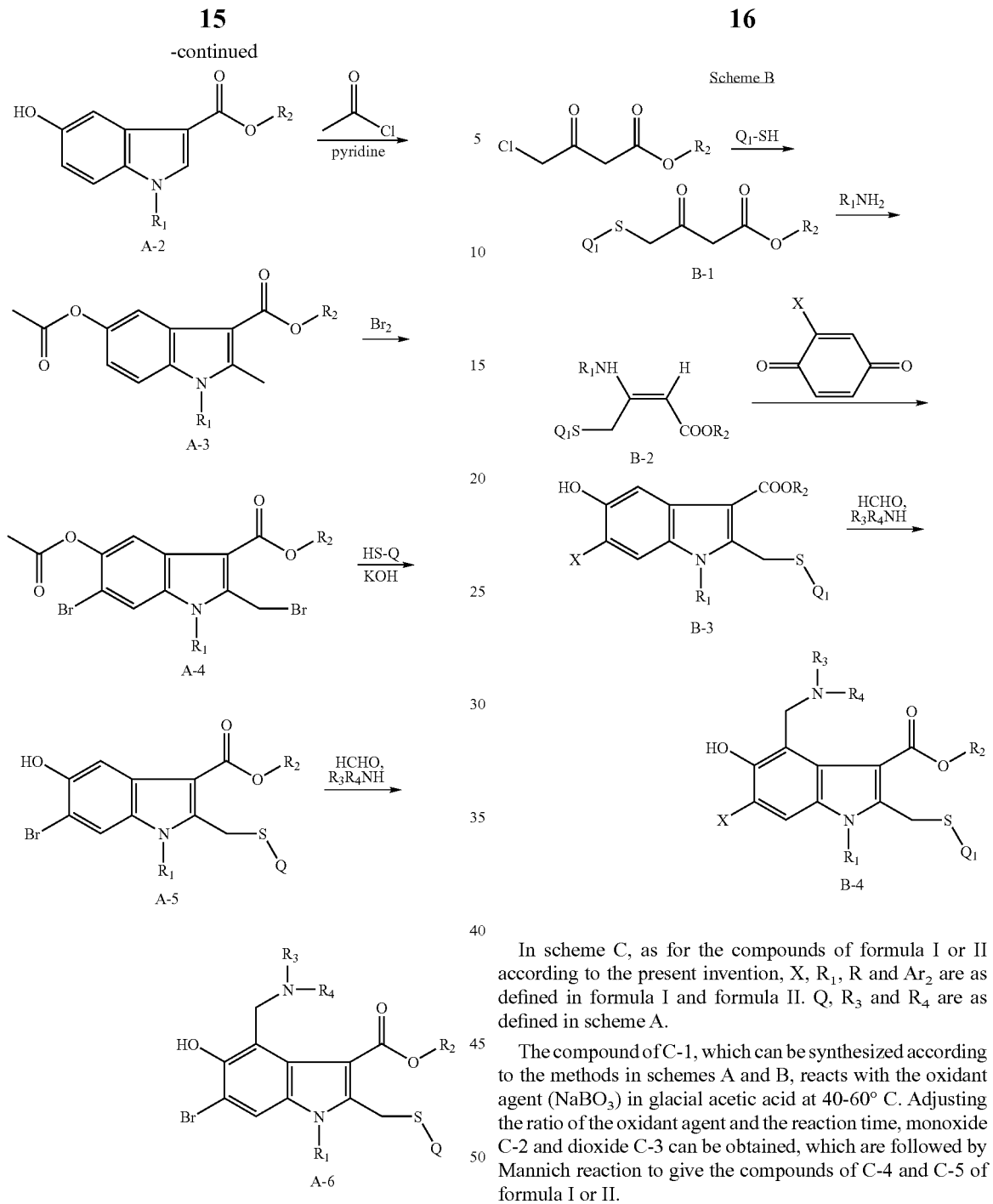

In scheme B, as for the compounds of formula I or II according to the present invention, X is H, F, Cl, I, —$NO_2$, —CN, —$CF_3$, or —$OCF_3$. Other substituents are as defined in scheme A.

The compound (B-1) is synthesized from commercial chloroacetoacetaic ester and $Q_1SH$ under basic condition at room temperature, and followed by refluxing with substituted amine in 1,2-dichloroethane for 12-24 h to give B-2. B-2 reacts with 1,4-benzoquinone under refluxing in 1,2-dichloroethane for 6-12 h. The solution is cooled and the precipitate is collected by filtration and dried to give B-3. Mannich reaction of B-3 gives B-4 of formula I or II.

In scheme C, as for the compounds of formula I or II according to the present invention, X, $R_1$, R and $Ar_2$ are as defined in formula I and formula II. Q, $R_3$ and $R_4$ are as defined in scheme A.

The compound of C-1, which can be synthesized according to the methods in schemes A and B, reacts with the oxidant agent ($NaBO_3$) in glacial acetic acid at 40-60° C. Adjusting the ratio of the oxidant agent and the reaction time, monoxide C-2 and dioxide C-3 can be obtained, which are followed by Mannich reaction to give the compounds of C-4 and C-5 of formula I or II.

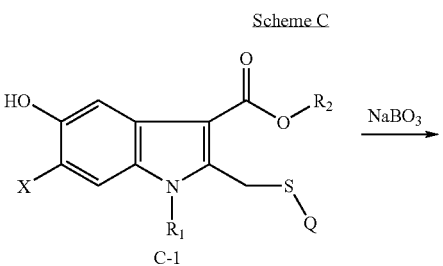

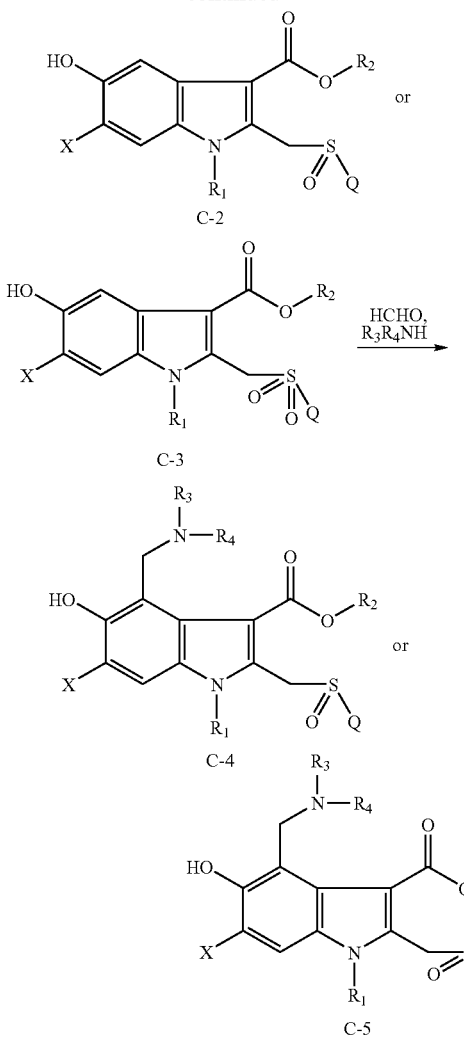

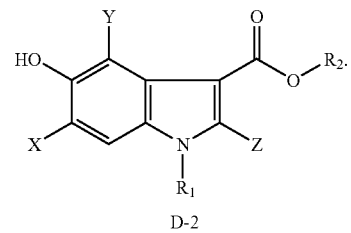

In Scheme D, as for the compounds of formula I or II according to the present invention, Y is —$NR_3R_4$ or —$S(CH2)mR_8$, wherein m is the integer from 1 to 4. $R_1$, $R_2$ and Z are as defined in formula I and formula II. $R_3$ and $R_4$ are covalently bonded together with the nitrogen to which they are attached to form guanidyl or 5- to 10-membered heteroaryl radical. Except the nitrogen atom to which $R_3$ and $R_4$ are attached, said heteraryl radical may have optionally 1 to 4 heteroatoms selected from N, O or S. Said heteroaryl radical can be optionally substituted with 1 to 3 same or different $R_8$. Other substituents are as defined in formula I and formula II.

Scheme D

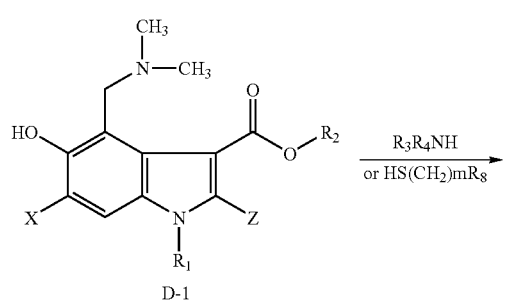

The compound of D-1 can be obtained according to methods provided by schemes A, B, C. The compound of D-1 reacts with $HNR_3R_4$ or $HS(CH_2)mR_8$ in ethanol-water (1:1, V/V) at 60-80° C. for 4-12 h. The solution is concentrated, extracted by dichloromethane, dried, evaporated to dryness and at last recrystallized in methanol or ethanol or chromatographed over silica gel to give D-2 of the formula I or II.

EXAMPLES

The examples are provided for purposes of illustration only and are not to be construed as limiting the scope of the instant invention. Proton ($^1H$) nuclear magnetic resonance spectroscopy was performed using Bruker ARX-300. Mass spectra (MS) were determined on Agilent 1100 LC-MSD. The reagents used were all analytically pure or chemically pure.

Preparation of the Thioalcohol and Thiophenol Intermediates:

Some thioalcohols and thiophenols are commercially available and others are prepared as follows:

Method 1: The Preparation of $R_5SH$

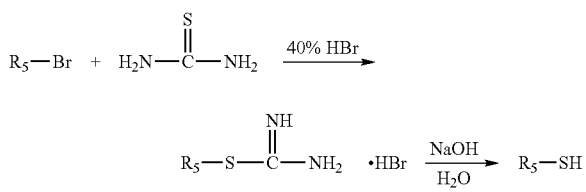

To 700 mL of acetic acid were added 0.1 mol of $R_5Br$, 0.2 mol of thiourea and 0.3 mol of 40% hydrobromic acid. The reaction mixture was stirred under reflux for 3 h, and then cooled to room temperature. The precipitate was filtered and dried to give 40%-60% yield of the isothiuronium bromide of $R_5$.

To 200 mL of ethanol were added 0.1 mol of the isothiuronium bromide of $R_5$, 0.22 mol of sodium hydroxide and 50 mL of water. The solution was stirred at room temperature for 16-24 h., and then filtered. The solvent was evaporated in vacuo and a small amount of water was added. The aqueous solution was adjusted to pH 2-3 with diluted hydrochloride acid. The oil was separated from the water, which was then extracted with diethyl ether. The organic phase was washed with water, dried, and evaporated in vacuo to give R₅SH.

Method 2: The Preparation of ArSH

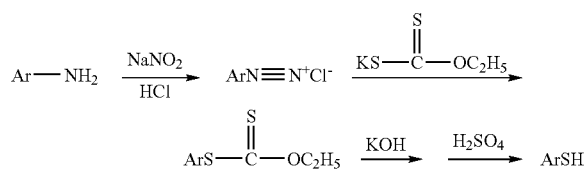

Wherein Ar is $C_6$-$C_{10}$ aryl radical, 5- to 10-membered heteroaryl radical and 5- to 10-membered heterocyclic radical. Said heterocyclic and heteroaryl radicals may have optionally 1 to 3 heteroatoms selected from N, O or S. Ar can be optionally substituted with 1 to 3 same or different $R_9$.

To a solution of 0.24 mol of concentrated hydrochloric acid and 20 g of crushed ice was added 0.1 mol of ArNH₂ dropwise under stirring. The mixture was cooled to 0° C., and a cold solution of 0.11 mol of sodium nitrile (NaNO₂) in 20 mL of water was added dropwise with the temperature being kept below 4° C. To 150 mL of water were added 0.12 mol of potassium ethyl xanthate and 0.37 mol of potassium hydroxide. The mixture was warmed to 40° C. and the previously synthesized diazonium solution was added slowly. After the addition, the mixture was kept at 40-45° C. for 0.5 h, and then cooled down, extracted with diethyl ether, washed with water, and dried. The ether was removed in vacuo to give ArSH.

Method 3: Preparation of HS—(CH₂)$_p$—(O)$_q$—Ar
(p is an Integer from 1 to 4, and q is 0 or 1)

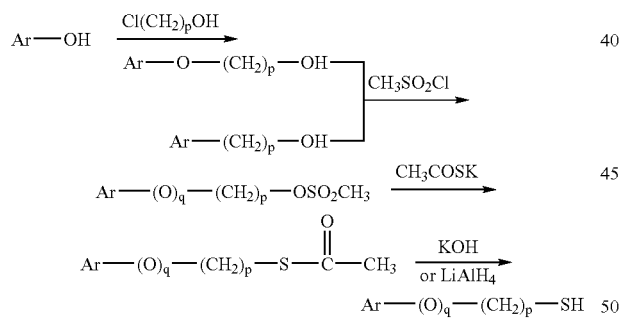

To 150 mL of N,N-dimethylformamide were added 0.1 mol of substituted phenol (ArOH), 0.2 mol of Cl(CH₂)$_p$OH and 0.2 mol of anhydrous potassium carbonate and the resulted mixture was kept at 110° C. for 6-10 h. Then the solvent was distilled, and a small amount of water was added. After being extracted with methylene chloride, the solution was washed with dilute sodium hydroxide, then washed with water to neutral, dried. The solution was evaporated to give ArO(CH₂)$_p$OH which was used directly in the next reaction.

To 150 mL of methylene chloride were added 0.1 mol of ArO(CH₂)$_p$OH or Ar(CH₂)$_p$OH and 0.2 mol of pyridine, and then a solution of 0.11 mol of methylsulfonyl chloride in 150 mL of methylene chloride was added dropwise below 10° C. after the temperature was cooled to −5° C. by ice-salt bath. After stirring at 5-10° C. for 12-18 h, the solvent was poured into 100 mL of water, and the organic phase was washed with water to neutral, dried, and evaporated to give the methylsulfonyl ester of ArO(CH₂)$_p$OH or Ar(CH₂)$_p$OH which was used directly in the next reaction.

To 200 mL of absolute ethanol were added 0.1 mol of the methylsulfonyl ester of ArO(CH₂)$_p$OH or Ar(CH₂)$_p$OH and 0.13 mol of potassium thioacetate. After stirring at 50-60° C. for 6-12 h, the mixture was added to a small amount of water, and then extracted with methylene chloride, washed with water, dried, and evaporated to give

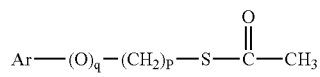

which was used directly in the next reaction.

When q is 0,

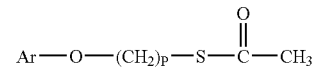

was hydrolyzed in the solution of potassium hydroxide in methanol.

0.1 mol of

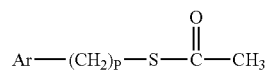

was added to methanol, and then the solution was cooled to 0-5° C. After a solution of 0.11 mol of potassium hydroxide in methanol was added below 5° C., the mixture was stirred at 0-5° C. until that TLC indicated the reaction was complete. The solution was poured into a small amount of water, extracted with ethyl acetate, washed with water, dried, and evaporated to give Ar—(CH₂)$_p$—SH which was used directly in the next reaction.

When q is 1, Ar—O—(CH₂)$_p$—SH is obtained by the reduction of

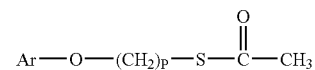

with lithium aluminium hydride.

To the suspension of 0.1 mol of lithium aluminium hydride in diethyl ether was added dropwise the solution of 0.1 mol of

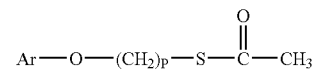

in absolute diethyl ether, the reaction temperature kept at 20-25° C. Then 1 mol/L hydrochloride acid was added dropwise after the solution was stirred for 0.5-4 h. The organic phase was separated, washed with water, dried, evaporated to give Ar—O—(CH₂)$_p$—SH which was used directly in the next reaction.

General Procedure 1 for the Preparation (Scheme A)

Step A: Preparation of 3-alkylaminocrotonate (A-1)

A gas generation device was set up and 1.4 mol of Methylamine or ethylamine solution was added dropwise to 300 mL of 50% solution of sodium hydroxide in three-necked bottle under stirring and gently heating. The methylamine or ethylamine gas was conducted into 1.3 mol of acetoacetic ester with temperature at 35-40° C. 300 mL of diethyl ester was then added to the reaction solution after stirring at room temperature for 17 h. The organic phase was separated, washed with water to pH 8, dried over anhydrous sodium sulfate and evaporated in vacuo to give 70-90% yield of 3-methylamino(ethylamino)-2-crotonate. The residue was used directly in the next reaction.

As for the preparation of 3-alkylamino-2-crotonate wherein the hydrocarbyl radicals is $C_3$-$C_6$ alkyl, $C_3$-$C_7$ cycloalkyl or substituted alkyl and cycloalkyl, the alkyl substituted amine could be dropped directly into acetoacetic ester according to above procedure without gas generating equipment.

Step B: Preparation of 1-alkyl-5-hydroxy-2-methyl-1H-indole-3-carboxylate (A-2)

To 100 mL of 1,2-dichloroethane was added 0.096 mol of 1,4-benzoquinone, and the mixture was stirred and heated to 60° C. After 1,4-benzoquinone was dissolved, Compound A-1 was added dropwise to the solution and reacted under refluxing for 8 h. The solution was cooled to room temperature and kept overnight. The precipitate was collected by filtration, washed with cold acetone, dried, and recrystallized from acetone to give 40-60% yield of compound A-2.

Step C: Preparation of 5-acetoxy-1-alkyl-2-methyl-1H-indole-3-carboxylate (A-3)

To 80 mL of acetone were added 0.05 mol of compound A-2 and 10 mL (0.1 mol) of pyridine, and when compound A-2 was completely dissolved, 5.5 mL (0.075 mol) of acetyl chloride was added dropwise under 30° C. The solution was stirred at room temperature for 4 h, then poured into icy water and kept overnight. The precipitate was collected by filtration, washed with water, and dried to give 75-90% yield of compound A-3.

Step D: Preparation of 5-acetoxy-1-alkyl-6-bromo-2-bromomethyl-1H-indole-3-carboxylate (A-4)

0.04 mol of Compound A-3 was added to 50 mL of carbon tetrachloride, and the reaction mixture was heated under reflux until A-3 was dissolved completely. Catalytic amount of benzoyl peroxide was added and then 5.1 mL (0.1 mol) of dry bromine was added under reflux. After refluxing for 5 h, the mixture was cooled and the precipitate was collected by filtration, washed with water and then methanol to give compound A-4 in 65-85% yield.

Step E: Preparation of 1-alkyl-6-bromo-5-hydroxy-2-(substituted thiomethyl)-1H-indole-3-carboxylate (A-5)

To 40 mL of methanol were added 5 g (0.09 mol) of potassium hydroxide and 0.03 mol of substituted thioalcohols or thiophenols, and the mixture was stirred at room temperature for 2 h. 0.03 mol of Compound A-4 was added portionwise and then the reaction mixture was stirred at room temperature for 6-8 h. The resulting mixture was neutralized with diluted hydrochloric acid, and the resulting precipitate was collected by filtration, washed successively with water, methanol and acetoacetic ester, recrystallized from ethanol and dried to give 60-90% yield of compound A-5.

Step H: Preparation of 4-[(aliphatic amino)methyl]-1-alkyl-6-bromo-5-hydroxy-2-(substituted thiomethyl)-1H-indole-3-carboxylate (A-6)

To 50 mL of glacial acetic acid were successively added 0.032 mol of aliphatic amine, 1.1 mL (0.014 mol) of 37% formalin solution, and 0.013 mol of compound A-5, and the reaction mixture was stirred at 50-55° C. for 6-8 h. The solvent was evaporated in vacuo, and 20 mL of water was added in one portion. The pH of resulted mixture was adjusted to 10 with 20% sodium hydroxide solution, and extracted with methylene chloride. The organic phase was pooled and dried over anhydrous magnesium sulfate, evaporated to yield oily compound.

The oil was dissolved in 30 mL of acetone. To the solution was added some diethyl ether dropwise, and the precipitate was filtered, washed with a little acetone and diethyl ether to give 40-70% yield of compound A-6;

Alternatively, the oil was dissolved in 30 mL of acetone. To the solution was added the ethanol solution of hydrochloride acid to adjust pH to 1-2, and then some diethyl ether was added dropwise to form a turbid solution. The resulted mixture was kept overnight, and crystallized to give 40-70% yield of compound A-6 hydrochloride.

Following the general procedure 1, the compounds of Examples 1-32 were synthesized respectively (Table 1).

TABLE 1

| Example No. | Chemical Name | Structure | $^1$H-NMR Data (300 Hz) d (ppm) |
|---|---|---|---|
| 1 | Ethyl 6-bromo-1-cyclopropyl-4-[(dimethylamino)methyl]-5-hydroxy-2-[(3-trifluoromethylphenyl)thiomethyl]-1H-indole-3-carboxylate hydrochloride | 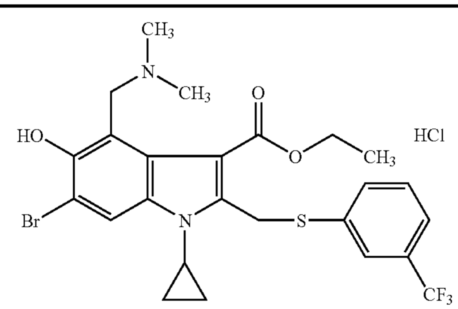 | (CDCl$_3$): 1.13 (m, 2 H), 1.23 (m, 2 H), 1.31 (t, 3 H), 2.80 (d, 6 H), 3.05 (m, 1 H), 4.21 (q, 2 H), 4.80 (s, 2 H), 5.18 (d, 2 H), 7.38 (m, 2 H), 7.52 (d, 1 H), 7.61 (s, 1 H), 7.93 (s, 1 H), 10.88 (br s, 1 H). |

TABLE 1-continued

| Example No. | Chemical Name | Structure | $^1$H-NMR Data (300 Hz) d (ppm) |
|---|---|---|---|
| 2 | Ethyl 6-bromo-4-[(dimethylamino)methyl]-5-hydroxy-1-isopropyl-2-[(4-isopropylphenyl)thiomethyl]-1H-indole-3-carboxylate hydrochloride | 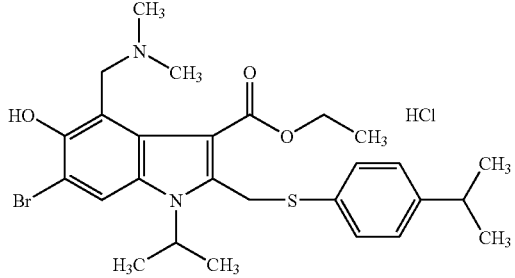 | (CDCl$_3$): 1.22 (d, 6 H), 1.28 (t, 3 H), 1.64 (d, 6 H), 2.83-2.89 (m, 7 H), 4.15 (q, 2 H), 4.54 (s, 2 H), 4.76 (m, 1 H), 5.04 (s, 2 H), 7.12 (d, 2 H), 7.23 (d, 2 H), 7.85 (s, 1 H), 9.90 (br s, 2 H). |
| 3 | Ethyl 6-bromo-4-[(dimethylamino)methyl]-5-hydroxy-1-methyl-2-[(benzo[d]imidazol-2-yl)thiomethyl]-1H-indole-3-carboxylate | 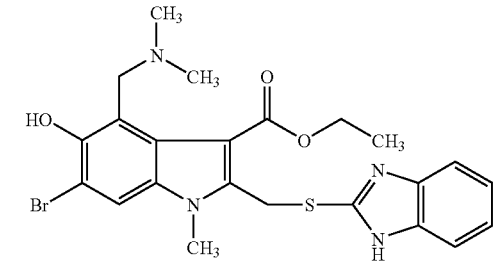 | (DMSO): 1.30 (t, 3 H), 2.28 (s, 6 H), 3.79 (s, 3 H), 4.09 (s, 2 H), 4.26 (q, 2 H), 5.02 (s, 2 H), 7.15 (m, 2 H), 7.37 (m, 1 H), 7.55 (m, 1 H), 7.73 (s, 1 H), 12.62 (brs, 1 H). |
| 4 | Ethyl 6-bromo-1-cyclopropyl-4-[(dimethylamino)methyl]-5-hydroxy-2-[(4-thiazolylmethyl)thiomethyl]-1H-indole-3-carboxylate dihydrochloride | 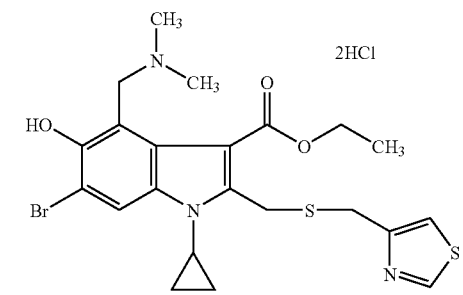 | (DMSO): 1.03 (m, 2 H), 1.19 (m, 2 H), 1.30 (t, 3 H), 2.77 (d, 6 H), 3.24 (m, 1 H), 4.01 (s, 2 H), 4.27 (q, 2 H), 4.45 (s, 2 H), 4.83 (d, 2 H), 7.56 (d, 1 H), 7.94 (s, 1 H), 9.10 (s, 1 H). |
| 5 | Ethyl 6-bromo-4-[(dimethylamino)methyl]-5-hydroxy-1-methyl-2-[(4-fluorobenzyl)thiomethyl]-1H-indole-3-carboxylate hydrochloride | 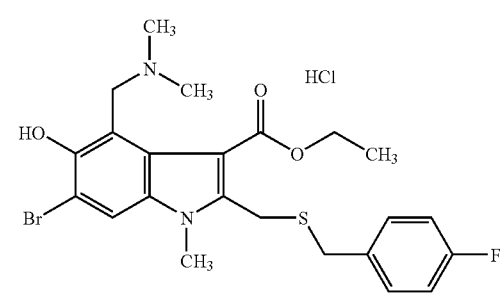 | (CDCl$_3$) 1.34 (t, 3 H), 2.84 (d, 6 H), 3.65 (s, 3 H), 3.75 (s, 3 H), 4.19 (s, 2 H), 4.28 (q, 2 H), 5.21 (d, 2 H), 6.99 (t, 2 H), 7.29 (d, 2 H), 7.61 (s, 1 H). |
| 6 | Ethyl 6-bromo-4-[(dimethylamino)methyl]-5-hydroxy-1-methyl-2-[(phenoxyethyl)thiomethyl]-1H-indole-3-carboxylate hydrochloride | 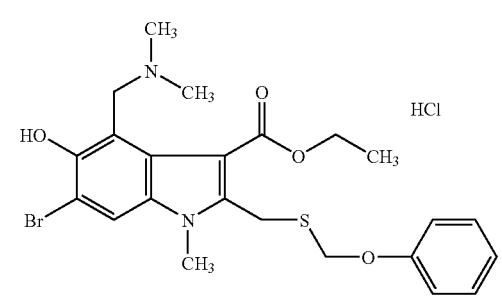 | (CDCl$_3$): 1.42 (t, 3 H), 2.83 (s, 6 H), 2.98 (t, 2 H), 3.78 (s, 3 H), 4.09 (t, 2 H), 4.38 (m, 4 H), 5.21 (d, 2 H), 6.82 (d, 2 H), 6.96 (t, 1 H), 7.26 (m, 2 H), 7.64 (s, 1 H), 10.90 (brs, 1 H). |

TABLE 1-continued

| Example No. | Chemical Name | Structure | ¹H-NMR Data (300 Hz) d (ppm) |
|---|---|---|---|
| 7 | Ethyl 6-bromo-5-hydroxy-1-methyl-4-[(N-methyloctylamino)methyl]-2-[(3-methylphenyl)thiomethyl]-1H-indole-3-carboxylate hydrochloride | 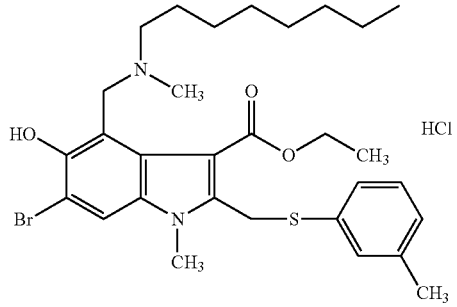 | (CDCl$_3$): 0.88 (t, 3 H), 1.27 (m, 13 H), 1.96 (m, 2 H), 2.26 (s, 3 H), 2.63 (d, 3 H), 3.13 (m, 2 H), 3.58 (s, 3 H), 4.19 (q, 2 H), 4.47 (d, 1 H), 4.59 (d, 1 H), 4.98 (m, 1 H), 5.47 (m, 1 H), 7.05-7.16 (m, 4 H), 8.29 (s, 1 H), 10.50 (br s, 1 H). |
| 8 | Ethyl 6-bromo-1-ethyl-5-hydroxy-4-(1-pyrrolidinylmethyl)-2-[(4-methylphenyl)thiomethyl]-1H-indole-3-carboxylate hydrochloride | 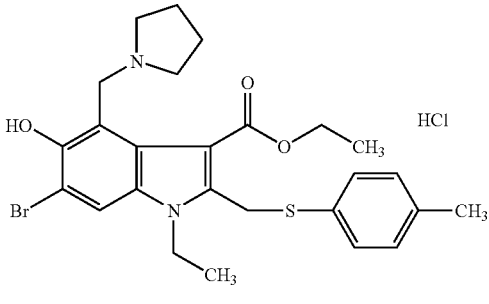 | (CDCl$_3$): 1.34 (t, 3 H), 1.38 (t, 3 H), 2.08 (m, 2 H), 2.15 (m, 2 H), 2.32 (s, 3 H), 3.17 (m, 2 H), 3.54 (m, 2 H), 4.09 (q, 2 H), 4.18 (q, 2 H), 5.24 (d, 2 H), 5.26 (s, 2 H), 7.05 (d, 2 H), 7.17 (d, 2 H), 8.10 (s, 1 H), 8.10 (br s, 1 H), 10.76 (br s, 1 H). |
| 9 | Ethyl 6-bromo-1-cyclopropyl-5-hydroxy-4-(1-pyrrolidinylmethyl)-2-[(3-trifluoromethylphenyl)thiomethyl]-1H-indole-3-carboxylate hydrochloride | 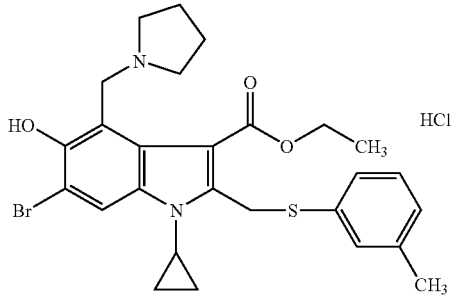 | (CDCl$_3$): 1.13 (m, 2 H), 1.27 (m, 2 H), 1.33 (t, 3 H), 2.10 (m, 2 H), 2.17 (m, 2 H), 3.08 (m, 1 H), 3.13 (m, 2 H), 3.54 (m, 2 H), 4.22 (q, 2 H), 4.81 (s, 2 H), 5.22 (d, 2 H), 7.39 (m, 2 H), 7.53 (d, 1 H), 7.61 (s, 1 H), 7.93 (s, 1 H), 10.85 (br s, 1 H). |
| 10 | Ethyl 6-bromo-1-cyclopropyl-5-hydroxy-4-(1-pyrrolidinylmethyl)-2-[(3-methoxyphenyl)thiomethyl]-1H-indole-3-carboxylate hydrochloride | 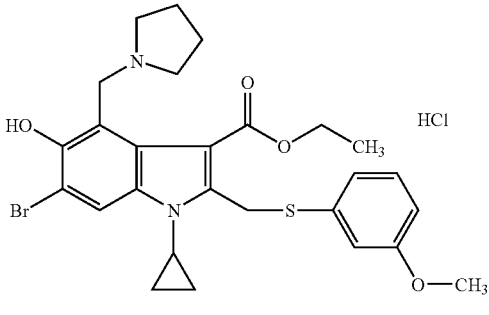 | (CDCl$_3$): 1.10 (m, 2 H), 1.23 (m, 2 H), 1.35 (t, 3 H, J = 7.1 Hz), 2.05-2.15 (m, 4 H), 2.97 (m, 1 H), 3.13 (m, 2 H), 3.50 (m, 2 H), 3.68 (s, 3 H), 4.23 (q, 2 H), 4.73 (s, 2 H), 5.21 (d, 2 H), 6.79~6.81 (m, 2 H), 6.88 (d, 1 H), 7.17 (t, 3 H), 7.89 (s, 1 H), 8.05 (br s, 1 H), 10.79 (br s, 1 H). |
| 11 | Ethyl 6-bromo-1-ethyl-5-hydroxy-4-(1-pyrrolidinylmethyl)-2-[(2,6-dichlorophenyl)thiomethyl]-1H-indole-3-carboxylate hydrochloride | 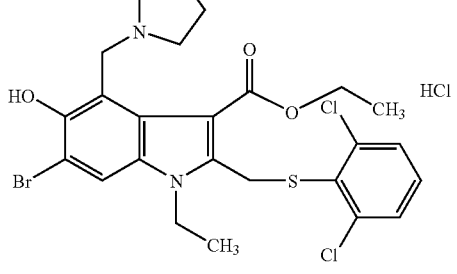 | (CDCl$_3$): 1.35 (t, 3 H), 1.46 (t, 3 H), 2.05 (m, 2 H), 2.17 (m, 2 H), 3.12 (m, 2 H), 3.49 (m, 2 H), 4.15 (q, 2 H), 4.24 (q, 2 H), 4.54 (s, 2 H), 5.15 (d, 2 H), 7.22 (q, 1 H), 7.32 (d, 2 H), 7.63 (s, 1 H), 10.80 (br s, 1 H). |

TABLE 1-continued

| Example No. | Chemical Name | Structure | $^1$H-NMR Data (300 Hz) d (ppm) |
|---|---|---|---|
| 12 | Ethyl 6-bromo-1-ethyl-5-hydroxy-4-(1-pyrrolidinylmethyl)-2-[(3-chlorophenyl)thiomethyl]-1H-indole-3-carboxylate hydrochloride | 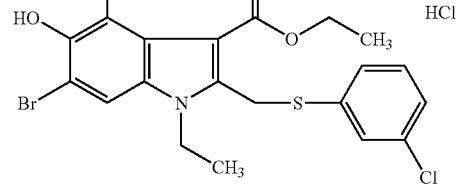 | (CDCl$_3$): 1.34 (t, 3 H), 1.44 (t, 3 H), 2.08~2.18 (m, 4 H), 3.15 (m, 2 H), 3.54 (m, 2 H), 4.14~4.25 (m, 4 H), 4.59 (s, 2 H), 5.23 (s, 2 H), 7.10~7.25 (m, 3 H), 7.33 (s, 1 H), 10.79 (s, 1 H). |
| 13 | Ethyl 6-bromo-1-cyclopropyl-5-hydroxy-4-(1-pyrrolidinylmethyl)-2-[(4-trifluoromethoxyphenyl)thiomethyl]-1H-indole-3-carboxylate hydrochloride | 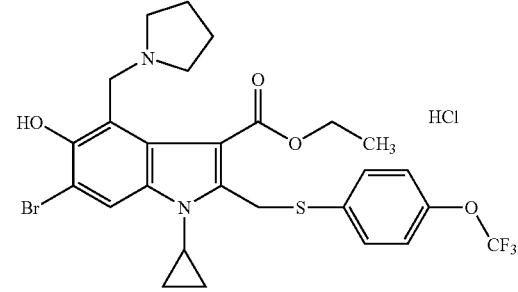 | (CDCl$_3$): 1.10 (m, 2 H), 1.26 (m, 2 H), 1.32 (t, 3 H), 2.07 (m, 2 H), 2.18 (m, 2 H), 3.02 (m, 1 H), 3.13 (m, 2 H), 3.54 (m, 2 H), 4.19 (q, 2 H), 4.73 (s, 2 H), 5.20 (d, 2 H), 7.11 (d, 2 H), 7.31 (d, 2 H), 7.91 (s, 1 H), 10.77 (br s, 1 H). |
| 14 | Ethyl 6-bromo-1-cyclopropyl-5-hydroxy-4-(1-pyrrolidinylmethyl)-2-[(2-fluorobenzyl)thiomethyl]-1H-indole-3-carboxylate hydrochloride | 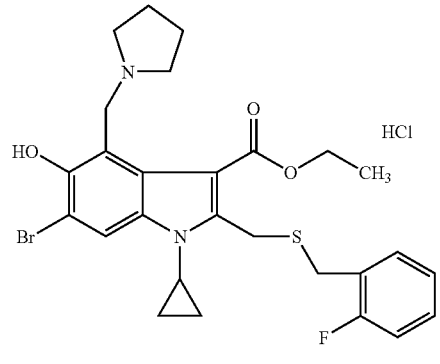 | (CDCl$_3$): 1.08 (m, 2 H), 1.13 (m, 2 H), 1.35 (t, 3 H), 2.13 (m, 4 H), 3.15 (m, 3 H), 3.53 (m, 2 H), 3.81 (s, 2 H), 4.28 (q, 2 H), 4.37 (s, 2 H), 5.21 (d, 2 H), 6.98~4.10 (m, 2 H), 7.19 (m, 1 H), 7.33 (m, 1 H), 7.88 (s, 1 H), 10.81 (brs, 1 H). |
| 15 | Ethyl 6-bromo-1-cyclopropyl-5-hydroxy-4-(1-pyrrolidinylmethyl)-2-[(3-chlorobenzyl)thiomethyl]-1H-indole-3-carboxylate hydrochloride | 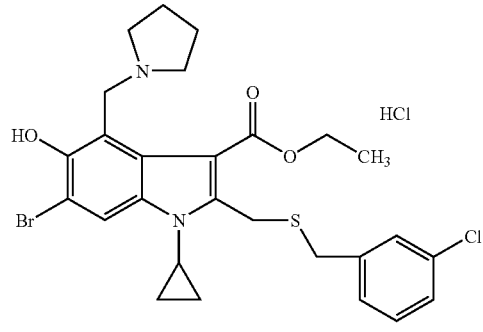 | (CDCl$_3$): 1.02 (m, 2 H), 1.13 (m, 2 H), 1.35 (t, 3 H), 1.93 (m, 4 H), 2.89 (m, 4 H), 3.12 (m, 1 H), 3.72 (s, 2 H), 4.26 (s, 2 H), 4.29 (q, 2 H), 4.51 (s, 2 H), 7.17 (m, 3 H), 7.28 (s, 1 H), 7.72 (s, 1 H). |
| 16 | Ethyl 6-bromo-5-hydroxy-1-methyl-4-(1-pyrrolidinylmethyl)-2-[(5-difluoromethylbenzo[d]imidazol-2-yl)thiomethyl]-1H-indole-3-carboxylate | 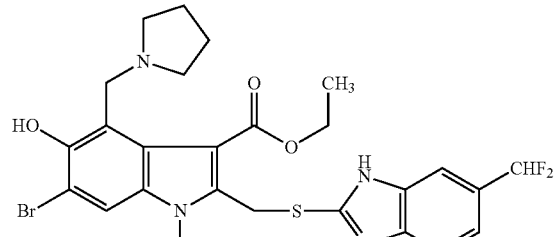 | (DMSO): 1.33 (t, 3 H), 1.88 (m, 2 H), 2.01 (m, 2 H), 3.22 (m, 2 H), 3.37 (m, 2 H), 3.89 (s, 3 H), 4.31 (q, 2 H), 4.96 (d, 2 H), 5.18 (s, 2 H), 6.98 (s, 0.25 H), 7.07 (d, 1 H), 7.23 (s, 0.5 H), 7.34 (s, 1 H), 7.48 (s, 0.25 H), 7.54 (d, 1 H), 8.05 (s, 1 H), 9.32 (br s, 2 H). |

TABLE 1-continued

| Example No. | Chemical Name | Structure | $^1$H-NMR Data (300 Hz) d (ppm) |
|---|---|---|---|
| 17 | Ethyl 6-bromo-5-hydroxy-1-methyl-4-[(4-methyl-1-piperazinyl)methyl]-2-[(4-fluorophenyl)thiomethyl]-1H-indole-3-carboxylate dihydrochloride | 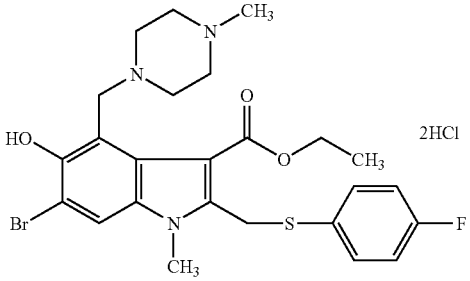 | (DMSO): 1.26 (t, 3 H), 2.78 (s, 3 H), 3.43-3.94 (m, 12 H), 4.19 (m, 2 H), 4.70 (s, 2 H), 8.04 (s, 1 H), 12.25 (s, 2 H). |
| 18 | Ethyl 6-bromo-1-ethyl-5-hydroxy-4-[(4-methyl-1-piperazinyl)methyl]-2-[(4-chlorophenyl)thiomethyl]-1H-indole-3-carboxylate dihydrochloride | 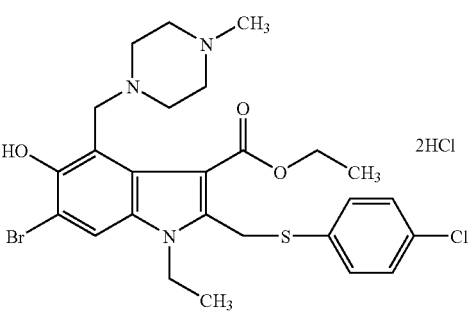 | (DMSO): 1.22 (t, 3 H), 1.28 (t, 3 H), 2.78 (s, 3 H), 3.29~3.60 (m, 8 H), 4.20 (m, 2 H), 4.29 (m, 2 H), 4.74 (s, 2 H), 4.74 (s, 2 H), 7.42 (m, 4 H), 8.06 (s, 1 H), 12.05(s, 2 H). |
| 19 | Ethyl 6-bromo-1-cyclopropyl-5-hydroxy-4-[(4-methyl-1-piperazinyl)methyl]-2-[(4-fluorophenyl)thiomethyl]-1H-indole-3-carboxylate dihydrochloride | 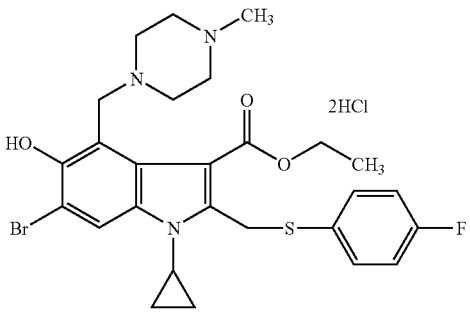 | (DMSO): 1.04 (s, 2 H), 1.23-1.28 (m, 5 H), 2.77 (m, 3 H), 3.09 (s, 2 H), 3.10~3.41 (m, 9 H), 4.18 (m, 2 H), 4.70 (s, 2 H), 7.18 (m, 2 H), 7.39 (m, 2 H), 7.86 (s, 1 H). |
| 20 | Ethyl 6-bromo-1-cyclopropyl-5-hydroxy-4-[(4-methyl-1-piperazinyl)methyl]-2-[(3,4-difluorophenyl)thiomethyl]-1H-indole-3-carboxylate dihydrochloride | 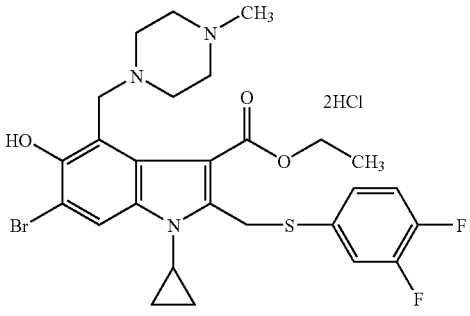 | (DMSO): 1.06 (m, 2 H), 1.26-1.28 (m, 5 H), 2.79 (d, 3 H), 3.17 (m, 1 H), 3.57 (m, 4 H), 3.93 (m, 4 H), 4.23 (q, 2 H), 4.79 (s, 2 H), 5.0 (br s, 2 H), 7.22 (m, 1 H), 7.13 (q, 1 H), 7.53 (m, 1 H), 7.95 (s, 1 H), 9.88 (br s, 2 H), 11.95 (br s, 1 H). |
| 21 | Ethyl 6-bromo-1-ethyl-5-hydroxy-4-(morpholinomethyl)-2-[(4-fluorophenyl)thiomethyl]-1H-indole-3-carboxylate hydrochloride | 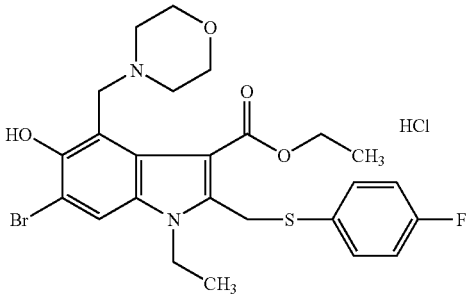 | (CDCl$_3$): 1.36 (t, 3 H), 1.41 (t, 3 H), 3.18-3.21 (m, 4 H), 3.87-3.91 (m, 2 H), 4.11 (q, 2 H), 4.21 (q, 2 H), 4.27-4.36 (m, 2 H), 4.50 (s, 2 H), 5.27 (d, 2 H), 6.94 (m, 2 H), 7.23 (m, 2 H), 7.67 (s, 1 H), 9.46 (br s, 1 H), 11.20 (br s, 1 H). |

TABLE 1-continued

| Example No. | Chemical Name | Structure | ¹H-NMR Data (300 Hz) d (ppm) |
|---|---|---|---|
| 22 | Ethyl 6-bromo-5-hydroxy-1-isopropyl-4-(morpholinomethyl)-2-(phenylthiomethyl)-1H-indole-3-carboxylate hydrochloride | 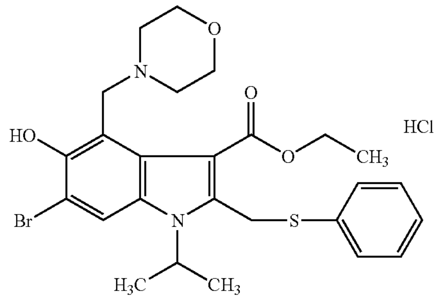 | (CDCl$_3$): 1.31 (t, 3 H), 1.67 (d, 2 H), 3.18 (br s, 4 H), 3.87 (m, 2 H), 4.19 (q, 2 H), 4.32 (m, 2 H), 4.59 (s, 2 H), 4.81 (m, 1 H), 5.19 (d, 2 H), 7.26 (m, 5 H), 7.91 (s, 1 H), 11.18 (br s, 1 H). |
| 23 | Ethyl 6-bromo-1-cyclopropyl-5-hydroxy-4-(morpholinomethyl)-2-[(3,4-dimethoxyphenyl)thiomethyl]-1H-indole-3-carboxylate hydrochloride | 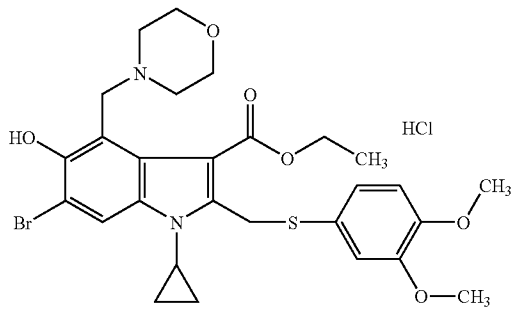 | (CDCl$_3$): 0.99 (m, 1 H), 1.17 (m, 2 H), 1.33 (t, 3 H), 2.63 (m, 4 H), 2.85 (m, 1 H), 3.56 (s, 3 H), 3.77 (m, 4 H), 3.85 (s, 3 H), 4.18 (m, 4 H), 4.56 (s, 2 H), 6.58 (d, 1 H), 6.72 (d, 1 H), 6.93 (d, 1 H), 7.69 (s, 1 H). |
| 24 | Ethyl 6-bromo-5-hydroxy-1-methyl-4-(morpholinomethyl)-2-[(2-pyridyl)thiomethyl]-1H-indole-3-carboxylate hydrochloride | 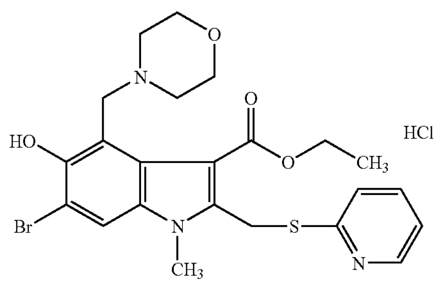 | (DMSO): 1.30 (s, 3 H), 3.29 (m, 4 H), 3.71 (m, 2 H), 3.84 (s, 3 H), 3.96 (m, 2 H), 4.31 (m, 2 H), 4.94 (s, 2 H), 5.01 (s, 2 H), 7.20 (m, 1 H), 7.36 (d, 1 H), 7.68 (m, 1 H), 8.05 (s, 1 H), 8.52 (d, 1 H), 9.46 (s, 1 H). |
| 25 | Ethyl 6-bromo-5-hydroxy-1-methyl-4-(morpholinomethyl)-2-[(5-methoxybenzo[d]imidazol-2-yl)thiomethyl]-1H-indole-3-carboxylate | 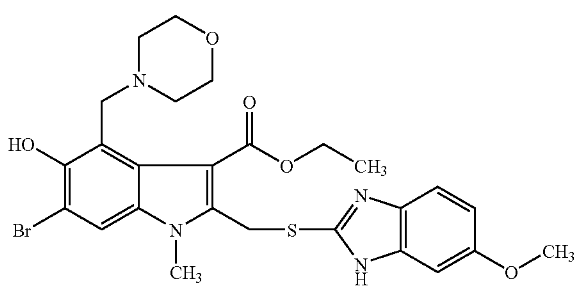 | (DMSO): 1.30 (t, 3 H), 2.49 (m, 4 H), 3.60 (m, 4 H), 3.79 (s, 6 H), 4.12 (s, 2 H), 4.25 (q, 2 H), 4.96 (s, 2 H), 6.73 (dd, 1 H), 6.96 (d, 1 H), 7.32 (d, 1 H), 7.73 (s, 1H). |
| 26 | Ethyl 6-bromo-5-hydroxy-1-methyl-4-(morpholinomethyl)-2-(benzylthiomethyl)-1H-indole-3-carboxylate hydrochloride | 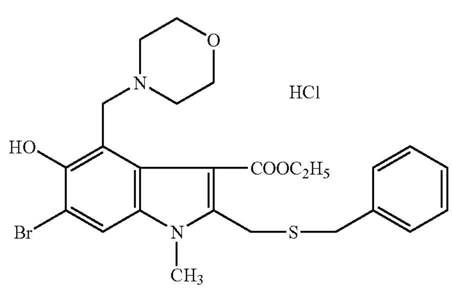 | (CDCl$_3$): 1.34 (t, 3 H), 3.22 (m, 4 H), 3.59 (s, 3 H), 3.78 (s, 2 H), 3.87 (m, 2 H), 4.17 (s, 2 H), 4.23~4.33 (m, 4 H), 5.29 (d, 2 H), 7.25~7.31 (m, 5 H), 7.62 (s, 1 H). |

TABLE 1-continued

| Example No. | Chemical Name | Structure | ¹H-NMR Data (300 Hz) d (ppm) |
|---|---|---|---|
| 27 | Ethyl 6-bromo-1-cyclopropyl-5-hydroxy-4-(morpholinomethyl)-2-[(3-chlorobenzyl)thiomethy]-1H-indole-3-carboxylate hydrochloride | 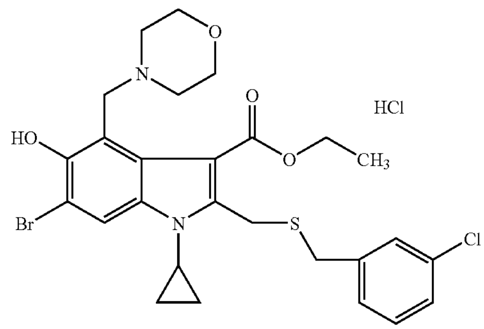 | (CDCl$_3$): 1.04 (m, 2 H), 1.18 (m, 2 H), 1.36 (t, 3 H), 3.14 (m, 1 H), 3.24 (m, 4 H), 3.88 (m, 2 H), 4.01 (m, 2 H), 4.29 (m, 6 H), 5.24 (d, 2 H), 7.18 (m, 3 H), 7.26 (s, 1 H), 7.90 (s, 1 H). |
| 28 | Ethyl 6-bromo-1-cyclopropyl-5-hydroxy-4-(morpholinomethyl)-2-[(5-methyl-4-imidazolylmethyl)thiomethyl]-1H-indole-3-carboxylate | 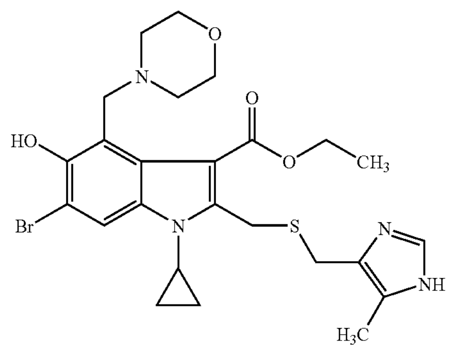 | (DMSO): 1.02 (m, 2 H), 1.10 (m, 2 H), 1.31 (t, 3 H), 2.08 (s, 3 H), 2.45 (m, 4 H), 3.16 (m, 1 H), 3.59 (m, 4 H), 3.69 (s, 2 H), 4.01 (s, 2 H), 4.25 (m, 4 H), 7.40 (s, 1 H), 7.68 (s, 1 H), 11.77 (brs, 1 H). |
| 29 | Ethyl 6-bromo-5-hydroxy-1-methyl-4-(morpholinomethyl)-2-[(1-adamantanyl)thiomethyl]-1H-indole-3-carboxylate hydrochloride | 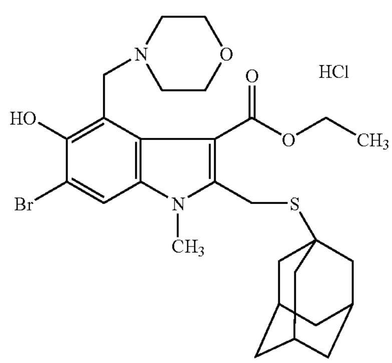 | (CDCl$_3$): 1.44 (t, 3 H), 1.73 (m, 6 H), 1.95 (m, 6 H), 2.09 (m, 3 H), 2.67 (m, 4 H), 3.72 (s, 3 H), 3.78 (m, 4 H), 4.20 (s, 2 H), 4.24 (s, 2 H), 4.40 (q, 2 H), 7.44 (s, 1 H). |
| 30 | Ethyl 6-bromo-1-cyclopropyl-5-hydroxy-4-(piperidinomethyl)-2-[(3,4-difluorophenyl)thiomethyl]-1H-indole-3-carboxylate hydrochloride | 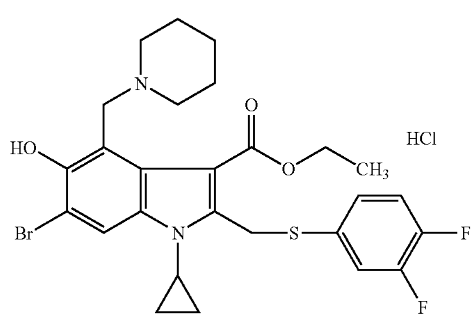 | (DMSO): 1.06 (m, 2 H), 1.23-1.28 (m, 5 H), 1.52 (m, 2 H), 1.69 (m, 4 H), 2.99 (m, 4 H), 3.19 (m, 1 H), 4.19 (q, 2 H), 4.64 (s, 2 H), 4.77 (s, 2 H,), 7.21 (m, 1 H), 7.37-7.53 (m, 2 H), 7.92 (s, 1 H). |

TABLE 1-continued

| Example No. | Chemical Name | Structure | $^1$H-NMR Data (300 Hz) d (ppm) |
|---|---|---|---|
| 31 | Ethyl 6-bromo-5-hydroxy-1-methyl-4-(piperidinomethyl)-2-[(3-chloro-4-fluorophenyl)thiomethyl]-1H-indole-3-carboxylate hydrochloride | 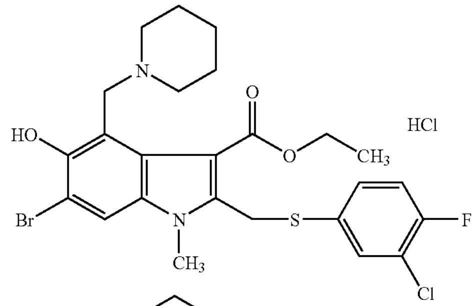 | (CDCl$_3$): 1.36 (t, 3 H), 1.77 (m, 2 H), 1.89 (m, 2 H), 2.28 (m, 2 H), 2.93 (m, 2 H), 3.33 (m, 2 H), 3.70 (s, 3 H), 4.21 (q, 2 H), 4.54 (s, 2 H), 5.15 (d, 2 H), 7.02 (m, 2 H), 7.38 (dd, 1 H), 7.68 (s, 1 H). |
| 32 | Ethyl 6-bromo-5-hydroxy-1-methyl-4-(piperidinomethyl)-2-[(benzo[d]imidazol-2-yl)thiomethyl]-1H-indole-3-carboxylate hydrochloride | 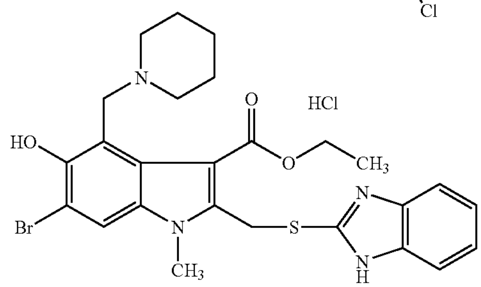 | (DMSO): 1.31 (t, 3 H), 1.47 (m, 2 H), 1.58 (m, 4 H), 2.61 (m, 4 H), 3.80 (s, 3 H), 4.24 (s, 2 H), 4.27 (q, 2 H), 5.03 (s, 2 H), 7.14 (m, 2 H), 7.37 (m, 1 H), 7.56 (ms, 1 H), 7.77 (s, 1 H), 12.64 (brs, 1 H). |

General Procedure 2 (Scheme B)

Step A: Preparation of Substituted Thioacetoacetic Ester (B-1)

0.11 mol of Q$_1$SH was dropped into a solution of 4.7 g (0.12 mol) potassium hydroxide in 80 mL of absolute ethanol at room temperature and stirred for 1 h, then 0.1 mol of chloroacetoacetic ester was added and the mixture was stirred at room temperature for 6 h. The solvent was evaporated in vacuo, extracted with diethyl ether, washed with 10% sodium carbonate solution, dried and evaporated to give 60-80% yield of arylthioacetoacetic ester.

Step B: Preparation of 3-alkylamino(amino)-4-substituted thiocrotonate (B-2)

A gas generation device was set up and 0.14 mol of ammonia, methylamine or ethylamine gas was conducted to a solution of 0.07 mol of compound B-1 in 150 mL of 1,2-dichloroethane (C$_3$-C$_4$ amine could be directly dropped into the solvent). Then the mixture was heated to 50-60° C. and reacted for 12-24 h. After washed with water, and dried, the solution was evaporated to give 65-85% yield of 3-alkylamino(amino)-4-substituted thiocrotonate (B-2).

Step C: Preparation of 1-alkyl-5-hydroxy-6-substituted (or hydrogen)-2-(substituted thiomethyl)-1H-indole-3-carboxylate (B-3)

A solution of 0.1 mol of compound B-2 in 100 mL of 1,2-dichloroethane was added dropwise to a solution of 0.11 mol of substituted 1,4-benzoquinone in 60 mL of 1,2-dichloroethane while keeping the mixture boiling and refluxing for 6-12 h. The solution was cooled and the precipitate was collected by filtration and dried to give 40-70% yield of 1-alkyl-5-hydroxy-6-substituted(hydrogen)-2-(substituted thiomethyl)-1H-indole-3-carboxylate (B-3).

Step D: Preparation of 1-alkyl-4-[(aliphatic amino) methyl]-5-hydroxy-6-substituted(hydrogen)-2-(substituted thiomethyl)-1H-indole-3-carboxylate (B-4)

Compound B-4 was synthesized from compound B-3, appropriate amine and 37% formalin solution following step H in general procedure 1.

Following the general procedure 2, the compounds of Examples 33-47 were synthesized respectively (Table 2).

TABLE 2

| Example No. | Chemical Name | Structure | $^1$H-NMR Data (300 Hz) d (ppm) |
|---|---|---|---|
| 33 | Ethyl 4-[(dimethylamino)methyl]-5-hydroxy-1-methyl-2-indole-3-carboxylate hydrochloride | 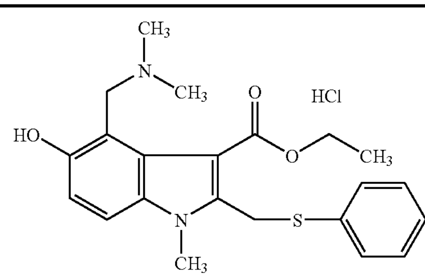 | (DMSO): 1.25 (t, 3 H), 2.76 (d, 6 H), 3.69 (s, 3 H), 4.20 (m, 2 H), 4.73 (s, 2 H), 4.75 (s, 2 H), 7.04 (d, 1 H), 7.29-7.41 (m, 5 H), 7.56 (d, 1 H), 8.69 (s, 1 H). |

TABLE 2-continued

| Example No. | Chemical Name | Structure | ¹H-NMR Data (300 Hz) d (ppm) |
|---|---|---|---|
| 34 | Ethyl 1-cyclopropyl-4-[(dimethylamino)methyl]-5-hydroxy-2-[(4-fluorophenyl)thiomethyl]-1H-indole-3-carboxylate | 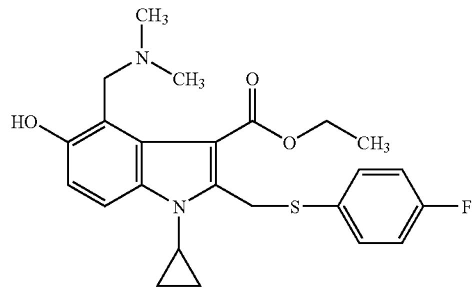 | (CDCl₃): 1.07 (m, 2 H), 1.16 (m, 2 H), 1.32 (t, 3 H), 2.34 (s, 6 H), 3.03 (m, 1 H), 4.04 (s, 2 H), 4.18 (q, 2 H), 4.62 (s, 2 H), 6.85 (d, 1 H), 6.89 (t, 2 H), 7.26 (t, 2 H), 7.39 (d, 2 H). |
| 35 | Ethyl 4-[(dimethylamino)methyl]-5-hydroxy-1-methyl-2-[(3,4-dimethoxyphenyl)thiomethyl]-1H-indole-3-carboxylate hydrochloride | 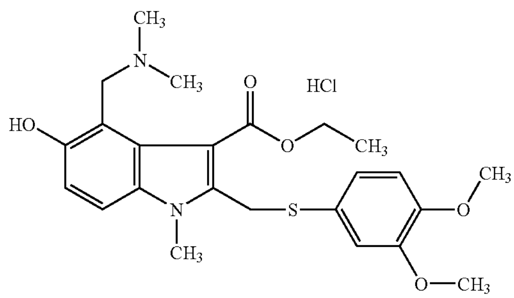 | (CDCl₃): 1.38 (t, 3 H), 2.84 (d, 6 H), 3.50 (s, 3 H), 3.56 (s, 3 H), 3.86 (s, 3 H), 4.21 (q, 2 H), 4.47 (s, 2 H), 5.09 (d, 2 H), 6.60 (d, 1 H), 6.72 (d, 2 H), 6.90 (dd, 1 H), 7.28 (d, 1 H), 7.36 (d, 1 H), 10.30 (brs, 1 H). |
| 36 | Ethyl 4-[(dimethylamino)methyl]-5-hydroxy-2-[(4-methylphenyl)thiomethyl]-1H-indole-3-carboxylate | 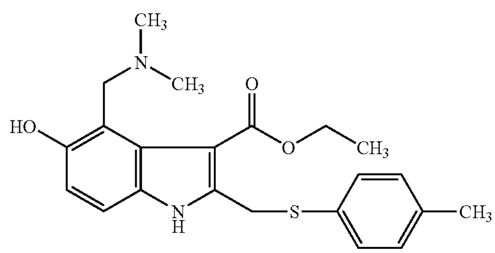 | (CDCl₃): 1.40 (t, 3 H), 2.29 (s, 3 H), 2.54 (s, 6 H), 4.32 (q, 2 H), 4.53 (s, 2 H), 4.61 (s, 2 H), 6.88 (d, 1 H), 7.06 (d, 2 H), 7.13 (d, 1 H), 7.17 (d, 2 H), 8.92 (brs, 1 H). |
| 37 | Ethyl 1-cyclopropyl-5-hydroxy-4-[(N-methylcyclopropylamino)methyl]-2-(phenylthiomethyl)-1H-indole-3-carboxylate oxalate | 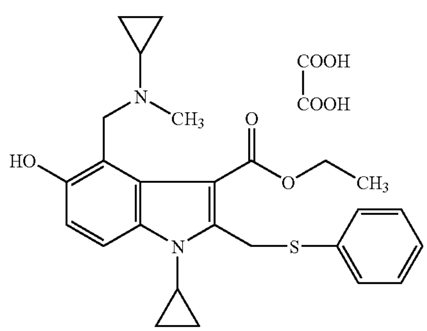 | (DMSO): 0.72 (m, 2 H), 0.85 (m, 2 H), 1.09 (m, 2 H), 1.23 (m, 2 H), 1.30 (t, 3 H), 2.61 (s, 3 H), 2.74 (m, 1 H), 3.12 (m, 1 H), 4.24 (q, 2 H), 4.77 (s, 2 H), 4.84 (d, 2 H), 7.00 (d, 2 H), 7.32-7.43 (m, 5 H), 7.65 (d, 1 H), 8.50 (br s, 2 H). |
| 38 | Ethyl 1-cyclopropyl-5-hydroxy-4-[(N-methylisopropylamino)methyl]-2-(phenylthiomethyl)-1H-indole-3-carboxylate oxalate | 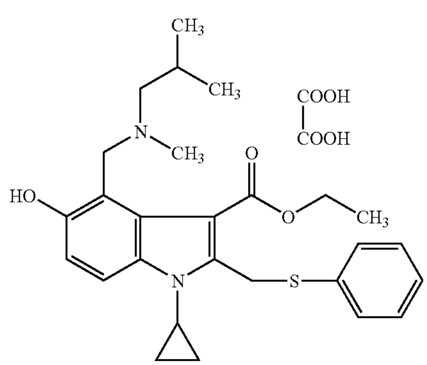 | (DMSO): 0.97 (s, 3 H), 0.99 (s, 3 H), 1.04 (m, 2 H), 1.22-1.27 (m, 5 H), 2.13 (m, 1 H), 2.63 (s, 3 H), 3.10 (m, 3 H), 4.20 (m, 2 H), 4.61 (m, 2 H), 4.81 (s, 2 H), 7.02 (d, 1 H), 7.31-7.41 (m, 5 H), 7.67 (d, 1 H), 10.08 (s, 1 H). |

TABLE 2-continued

| Example No. | Chemical Name | Structure | ¹H-NMR Data (300 Hz) d (ppm) |
|---|---|---|---|
| 39 | Ethyl 4-[(4-carboxypiperidino)methyl]-5-hydroxy-1-methyl-2-(phenylthiomethyl)-1H-indole-3-carboxylate hydrochloride | 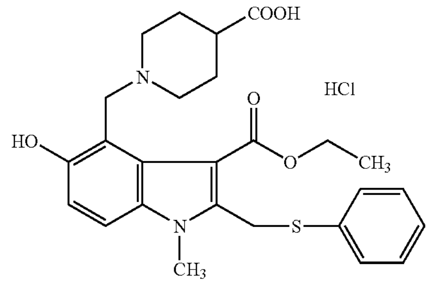 | (DMSO): 1.24 (t, 3 H), 1.77 (m, 2 H), 2.06 (m, 2 H), 3.15 (m, 3 H), 3.70 (s, 3 H), 4.19 (q, 2 H), 4.77 (m, 4 H), 7.02 (d, 1 H), 7.30-7.42 (m, 4 H), 7.56 (d, 1 H), 8.46 (br s, 1 H), 8.65 (br s, 1 H), 10.02 (d, 1 H), 12.46 (br s, 1 H). |
| 40 | Ethyl 5-hydroxy-1-methyl-4-(1-pyrrolidinylmethyl)-2-(phenylthiomethyl)-1H-indole-3-carboxylate hydrochloride | 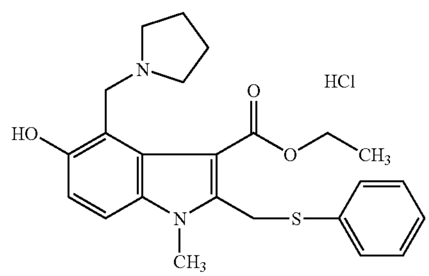 | (DMSO): 1.24 (t, 3 H), 1.89 (m, 2 H), 2.03 (s, 2 H), 3.25 (m, 2 H), 3.39 (m, 4 H), 3.69 (s, 3 H), 4.20 (m, 2 H), 4.76 (s, 2 H), 4.83 (d, 2 H), 7.04 (d, 1 H), 7.30-7.42 (m, 5 H), 7.54 (d, 1 H), 9.07 (s, 1 H). |
| 41 | Ethyl 1-cyclopropyl-5-hydroxy-4-(1-pyrrolidinylmethyl)-2-(phenylthiomethyl)-1H-indole-3-carboxylate | 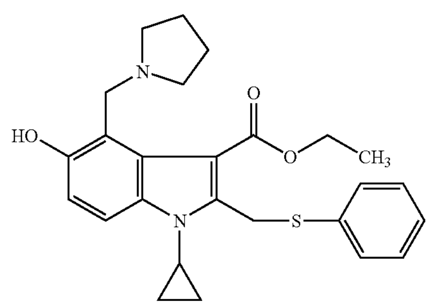 | (DMSO): 1.06 (m, 2 H), 1.20 (m, 2 H), 1.25 (t, 3 H), 1.89 (m, 2 H), 2.03 (m, 2 H), 3.08 (m, 1 H), 3.25 (m, 2 H), 3.39 (m, 2 H), 4.22 (q, 2 H), 4.79 (d, 2 H), 4.83 (s, 2 H), 7.07 (d, 1 H), 7.29~7.43 (m, 5 H), 7.65 (d, 1 H), 9.09 (br s, 1 H), 10.10 (s, 1 H). |
| 42 | Ethyl 5-hydroxy-4-(pyrrolidinylmethyl)-2-[(4-methylphenyl)thiomethyl]-1H-indole-3-carboxylate | 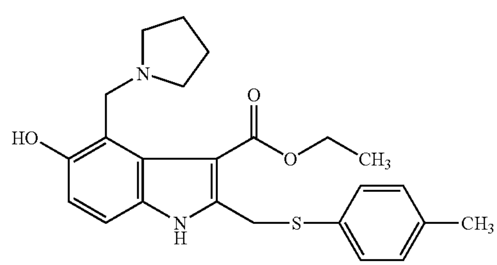 | (CDCl₃): 1.40 (s, 3 H), 1.77 (m, 4 H), 2.12 (s, 3 H), 2.30 (s, 3 H), 3.27 (m, 2 H), 3.54 (m, 2 H), 4.32 (q, 2 H), 4.54 (s, 2 H), 5.11 (s, 2 H), 7.09 (m, 3 H), 7.21 (m, 2 H), 10.19 (brs, 1 H). |
| 43 | Ethyl 5-hydroxy-1-methyl-4-(morpholinomethyl)-2-[(3-methoxyphenyl)thiomethyl]-1H-indole-3-carboxylate hydrochloride | 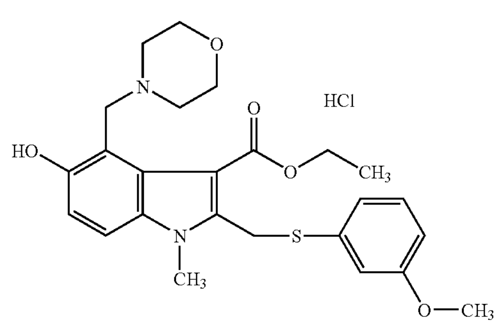 | (CDCl₃): 1.36 (t, 3 H), 3.22 (m, 4 H), 3.65 (s, 3 H), 3.92 (m, 2 H), 4.22 (m, 4 H), 4.58 (s, 2 H), 5.19 (s, 2 H), 6.74 (s, 1 H), 6.82 (d, 1 H), 6.92 (d, 1 H), 7.19 (t, 1 H), 7.32 (s, 2 H). |

TABLE 2-continued

| Example No. | Chemical Name | Structure | $^1$H-NMR Data (300 Hz) d (ppm) |
|---|---|---|---|
| 44 | Ethyl 1-cyclopropyl-5-hydroxy-4-(morpholinomethyl)-2-[(3,4-difluorophenyl)thiomethyl]-1H-indole-3-carboxylate hydrochloride | 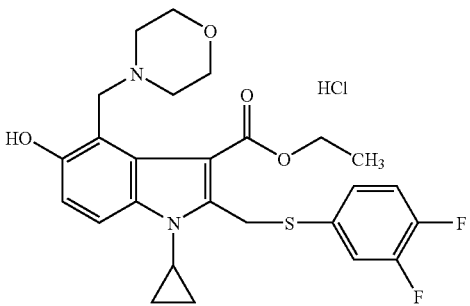 | (CDCl$_3$): 1.10 (m, 2 H), 1.27 (m, 2 H), 1.34 (t, 2 H), 3.09 (m, 1 H), 3.24 (m, 4 H), 3.94 (m, 2 H), 4.23 (m, 4 H), 4.73 (s, 2 H), 5.13 (s, 2 H), 7.02~7.12 (m, 3 H), 7.31 (d, 1 H), 7.64 (d, 1 H), 10.88 (brs, 1 H). |
| 45 | Ethyl 5-hydroxy-4-(morpholinomethyl)-2-[(4-methylphenyl)thiomethyl]-1H-indole-3-carboxylate | 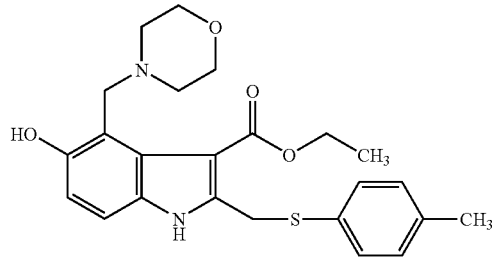 | (CDCl$_3$): 1.40 (t, 3 H), 2.29 (s, 3 H), 2.65 (m, 4 H), 3.76 (m, 4 H), 4.31 (s, 2 H), 4.34 (q, 2 H), 4.52 (s, 2 H), 6.79 (d, 1 H), 7.06 (d, 2 H), 7.11 (d, 1 H), 7.18 (d, 2 H), 8.76 (brs, 1 H). |
| 46 | Ethyl 1-cyclopropyl-5-hydroxy-4-(piperidinomethyl)-2-[(2-pyridyl)thiomethyl]-1H-indole-3-carboxylate hydrochloride | 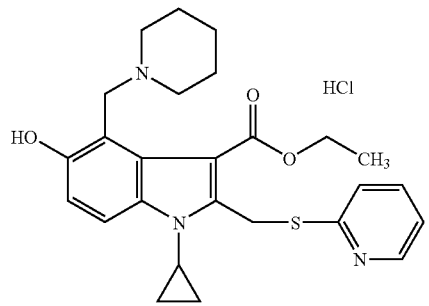 | $^1$(H$_2$O): 0.93 (m, 2 H), 1.13~1.18 (m, 5 H), 1.38~4.63 (m, 4 H), 1.77 (m, 2 H), 2.89 (m, 2 H), 3.07 (m, 1 H), 3.29 (m, 2 H), 4.16 (q, 2 H), 4.49 (s, 2 H), 4.92 (s, 2 H), 6.88 (d, 1 H), 7.40 (t, 1 H), 7.47 (d, 1 H), 7.63 (d, 1 H), 7.87 (t, 1 H), 8.39 (d, 1 H). |
| 47 | Ethyl 1-cyclopropyl-5-hydroxy-4-(piperidinomethyl)-2-[(3,4-dimethoxyphenyl)thiomethyl]-1H-indole-3-carboxylate hydrochloride | 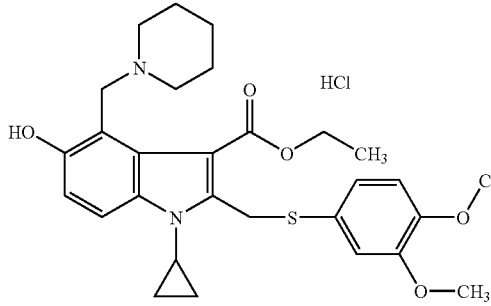 | (CDCl$_3$): 1.01 (m, 2 H), 1.21 (m, 2 H), 1.39 (t, 3 H), 1.59~2.18 (m, 4 H), 2.81 (m, 1 H), 3.02 (m, 2 H), 3.46 (m, 5 H), 3.86 (s, 3 H), 4.20 (s, 2 H), 4.63 (s, 2 H), 4.91 (s, 2 H), 6.46 (s, 1 H), 6.73 (d, 1 H), 6.94 (d, 1 H), 7.42 (s, 1 H), 7.57 (s, 1 H). 9.43 (brs, 1 H). |

General Procedure 3

Step A: Preparation of 1-alkyl-5-hydroxy-6-substituted (or hydrogen)-2-(substituted thiomethyl)-1H-indole-3-carboxylate (C-1)

Compound C-1 was obtained according to general procedure 1 and 2.

Step B: Preparation of 1-alkyl-5-hydroxy-6-substituted (or hydrogen)-2-(substituted sulfinylmethyl)-1H-indole-3-carboxylate (C-2)

To 50 mL of glacial acetic acid were added 0.01 mol of compound C-1 and 1.85 g (0.012 mol) sodium perborate tetrahydrate. The solution was stirred at 40-60° C. for 1-2 h. After TLC indicated the reaction was complete, the solvent was evaporated and 25 mL of water was added in one portion. The resultant mixture was adjusted to pH 10 with 10% solution of sodium hydroxide and extracted with methylene dichloride. The organic phase was washed with water, dried over anhydrous sodium sulfate, filtered and evaporated. Then, diethyl ether was poured into the solution and the precipitate was filtered and recrystallized from diethyl ester-acetone to give 60-80% yield of compound C-2.

Step C: Preparation of 1-alkyl-5-hydroxy-6-substituted (or hydrogen)-2-(substituted sulfonylmethyl)-1H-indole-3-carboxylate (C-3)

To 50 mL of glacial acetic acid were added 0.01 mol of compound C-1 and 3.85 g (0.025 mol) sodium perborate tetrahydrate. The solution was stirred at 40-60° C. for 24-36 h. After TLC indicated the reaction was complete, the solvent was evaporated and 25 mL of water was added in one portion. The resultant mixture was adjusted to pH 10 with 10% solution of sodium hydroxide and extracted with methylene dichloride. The organic phase was washed with a saturated sodium chloride solution and water, dried over anhydrous sodium sulfate, filtered and evaporated. Then, the precipitate was recrystallized from methanol to give 50-80% yield of compound C-3.

Step D: Preparation of 1-alkyl-5-hydroxy-6-substituted (or hydrogen)-4-(substituted aminomethyl)-2-(substituted sulfinylmethyl) (or (substituted sulfonylmethyl))-1H-indole-3-carboxylate (C-4 or C-5)

Compound C-4 or C-5 was synthesized from compound C-2 or C-3, appropriate aliphatic amine and 37% formalin solution following step H in general procedure 1.

Following the general procedure 3, the compound of Examples 48-87 were synthesized respectively (Table 3, 4).

TABLE 3

| Example No. | Chemical Name | Structure | $^1$H-NMR Data (300 Hz) d (ppm) |
|---|---|---|---|
| 48 | Ethyl 6-bromo-4-[(dimethylamino)methyl]-5-hydroxy-1-methyl-2-[(3-methylphenyl)sulfinylmethyl]-1H-indole-3-carboxylate | 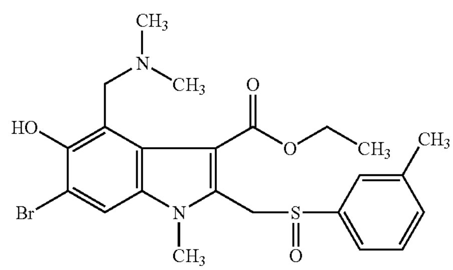 | (DMSO): 1.32 (t, 3 H), 2.28 (m, 9 H), 4.10 (d, 2 H), 4.19 (q, 2 H), 4.66 (d, 1 H), 4.74 (d, 1 H), 7.22 (m, 2 H), 7.44 (m, 2 H), 7.71 (s, 1 H). |
| 49 | Ethyl 6-bromo-1-cyclopropyl-4-[(dimethylamino)methyl]-5-hydroxy-2-[(4-hydroxyphenyl)sulfinylmethyl]-1H-indole-3-carboxylate hydrochloride | 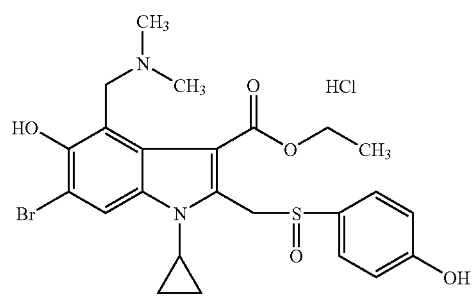 | (DMSO): 0.88 (m, 1 H), 1.07 (m, 1 H), 1.24 (m, 2 H), 1.39 (t, 3 H), 2.77 (s, 6 H), 4.32 (q, 2 H), 4.73 (d, 1 H), 4.87 (s, 2 H), 4.88 (d, 1 H), 6.89 (d, 2 H), 7.34 (d, 2 H), 7.91 (s, 1 H), 10.31. (brs, 1 H). |
| 50 | Ethyl 6-bromo-1-cyclopropyl-4-[(dimethylamino)methyl]-5-hydroxy-2-[(4-acetaminophenyl)sulfinylmethyl]-1H-indole-3-carboxylate | 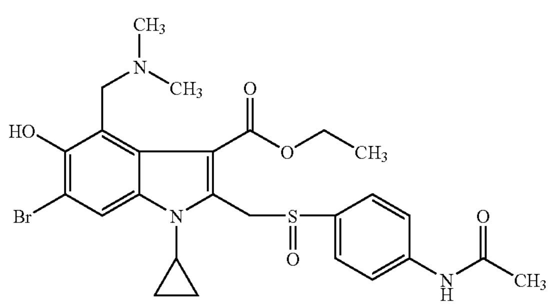 | (DMSO): 0.88 (m, 1 H), 1.06 (m, 1 H), 1.24 (m, 2 H), 1.38 (t, 3 H), 2.09 (s, 3 H), 2.19 (d, 6 H), 4.32 (q, 2 H), 4.79 (d, 1 H), 4.86 (s, 2 H), 4.92 (d, 1 H), 7.45 (d, 2 H), 4.75 (d, 2 H), 7.93 (s, 1 H), 8.88 (brs, 1 H), 9.49 (s, H), 10.36 (s, 1 H). |
| 51 | Ethyl 6-bromo-4-[(dimethylamino)methyl]-5-hydroxy-1-methyl-2-[(2-pyridyl)sulfinylmethyl]-1H-indole-3-carboxylate | 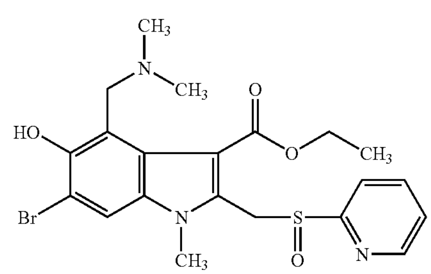 | (DMSO): 1.34 (t, 3 H), 2.29 (s, 6 H), 3.62 (s, 3 H), 4.03 (d, 1 H), 4.14 (d, 1 H), 4.20 (q, 2 H), 4.75 (d, 1 H), 4.98 (d, 1 H), 7.59 (m, 1 H), 7.74 (s, 1 H), 7.80 (d, 1 H), 8.01 (t, 1 H), 8.68 (d, 1 H). |

TABLE 3-continued

| Example No. | Chemical Name | Structure | $^1$H-NMR Data (300 Hz) d (ppm) |
|---|---|---|---|
| 52 | Ethyl 6-bromo-1-cyclopropyl-4-[(dimethylamino)methyl]-5-hydroxy-2-[(4-thiazolylmethyl)sulfinylmethyl]-1H-indole-3-carboxylate dihydrochloride | 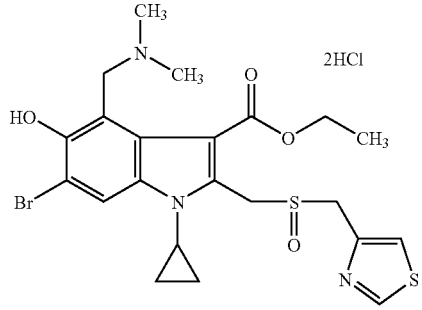 | (DMSO): 0.88 (m, 1 H), 1.26 (m, 5 H), 2.78 (d, 6 H), 3.22 (m, 1 H), 4.22 (q, 2 H), 4.51 (d, 1 H), 4.63 (d, 1 H), 4.80 (d, 1 H), 4.85 (m, 2 H), 4.90 (d, 1 H), 7.81 (d, 1 H), 7.80 (s, 1 H), 8.96 (brs, 1 H), 9.22 (d, 1 H), 9.51 (brs, 1 H). |
| 53 | Ethyl 6-bromo-4-[(dimethylamino)methyl]-5-hydroxy-1-methyl-2-[(2-phenoxyethyl)sulfinylmethyl]-1H-indole-3-carboxylate hydrochloride | 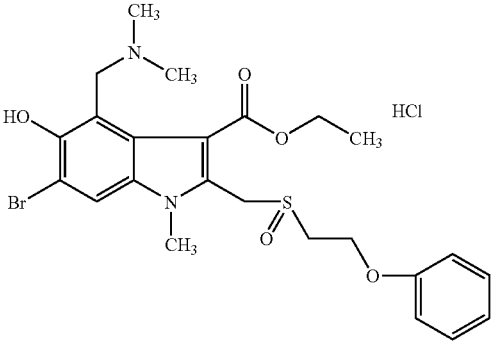 | (CDCl$_3$): 1.39 (t, 3 H), 2.84 (s, 6 H), 3.23 (m, 1 H), 3.37 (m, 1 H), 4.40 (q, 2 H), 4.47 (m, 1 H), 4.56 (m, 1 H), 4.65 (d, 1 H), 4.88 (d, 1 H), 5.13 (d, 1 H), 5.37 (d, 1 H), 6.94 (d, 2 H), 7.00 (t, 1 H), 7.32 (d, 2 H), 7.66 (s, 1 H). |
| 54 | Ethyl 4-[(dimethylamino)methyl]-5-hydroxy-1-methyl-2-[(2-furylmethyl)sulfonylmethyl)]-1H-indole-3-carboxylate hydrochloride | 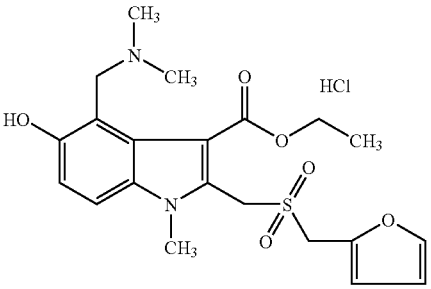 | (DMSO): 1.22 (t, 3 H), 2.78 (d, 6 H), 3.82 (s, 3 H), 4.18 (q, 2 H), 4.69 (d, 2 H), 4.82 (d, 2 H), 5.31 (s, 2 H), 6.57 (m, 1 H), 6.64 (t, 1 H), 7.13 (d, 1 H), 7.62 (d, 1 H), 7.81 (dd, 1 H), 10.19 (s, 1 H). |
| 55 | Ethyl 6-bromo-4-[(dimethylamino)methyl]-5-hydroxy-1-methyl-2-[(3-methoxyphenyl)sulfonylmethyl]-1H-indole-3-carboxylate | 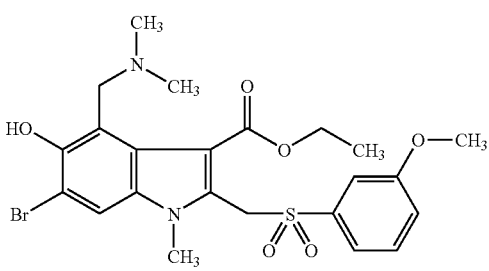 | (DMSO): 1.29 (t, 3 H), 2.27 (s, 3 H), 3.62-3.68 (m, 9 H), 4.05 (q, 2 H), 5.27 (s, 2 H), 7.04 (m, 1 H), 7.27 (m, 2 H), 7.52 (m, 1 H), 7.76 (s, 1 H). |
| 56 | Ethyl 6-bromo-1-cyclopropyl-4-[(dimethylamino)methyl]-5-hydroxy-2-[(4-thiazylmethyl)sulfoolylmethyl]-1H-indole-3-carboxylate | 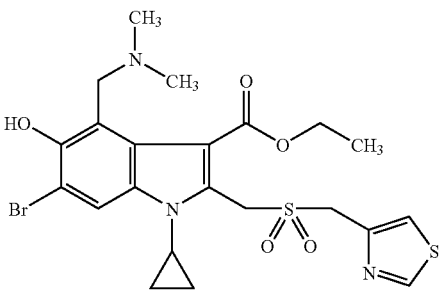 | (DMSO): 0.98 (m, 2 H), 1.14 (m, 2 H), 1.23 (t, 3 H), 2.27 (s, 6 H), 3.15 (m, 1 H), 4.01 (s, 2 H), 4.16 (q, 2 H), 4.95 (s, 2 H), 5.24 (s, 2 H), 7.73 (s, 1 H), 7.87 (s, 1 H), 9.23 (s, 1 H). |

TABLE 3-continued

| Example No. | Chemical Name | Structure | $^1$H-NMR Data (300 Hz) d (ppm) |
|---|---|---|---|
| 57 | Ethyl 6-bromo-5-hydroxy-1-methyl-4-(morpholinomethyl)-2-[(2-methylphenyl)sulfinylmethyl]-1H-indole-3-carboxylate | 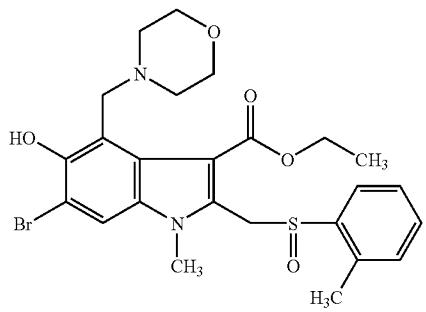 | (DMSO): 1.31 (t, 3 H), 2.13 (s, 3 H), 2.46 (m, 4 H), 3.60 (m, 7 H), 4.07 (d, 2 H), 4.16 (q, 2 H), 4.72 (d, 2 H), 7.25 (d, 1 H), 7.45 (m, 2 H), 7.66 (m, 1 H), 7.73 (s, 1 H). |
| 58 | Ethyl 6-bromo-5-hydroxy-1-methyl-4-(morpholinomethyl)-2-[(4-fluorophenyl)sulfinylmethyl]-1H-indole-3-carboxylate | 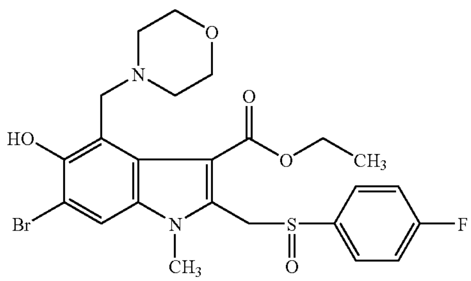 | (DMSO): 1.31 (t, 3 H), 2.49 (m, 4 H), 3.61 (m, 7 H), 4.05 (d, 1 H), 4.12 (d, 1 H), 4.17 (q, 2 H), 4.76 (s, 2 H), 7.38 (m, 2 H), 7.51 (m, 2 H), 7.74 (s, 1 H). |
| 59 | Ethyl 6-bromo-5-hydroxy-1-methyl-4-(morpholinomethyl)-2-[(3-chlorophenyl)sulfinylmethyl]-1H-indole-3-carboxylate | 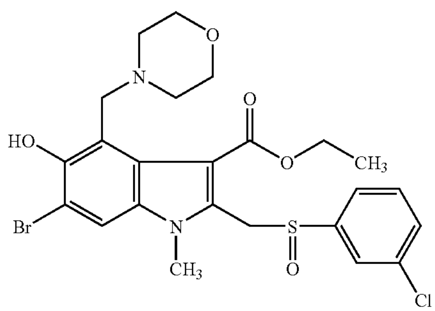 | (DMSO): 1.30 (t, 3 H), 2.49 (s, 4 H), 3.59 (s, 7 H), 4.04~4.19 (m, 4 H), 4.81 (s, 2 H), 7.38 (d, 1 H), 7.49 (d, 1 H), 7.55 (d, 1 H), 7.63 (d, 1 H), 7.74 (s, 1 H). |
| 60 | Ethyl 6-bromo-5-hydroxy-1-methyl-4-(morpholinomethyl)-2-[(3,4-dimethoxyphenyl)sulfinyl methyl]-1H-indole-3-carboxylate hydrochloride | 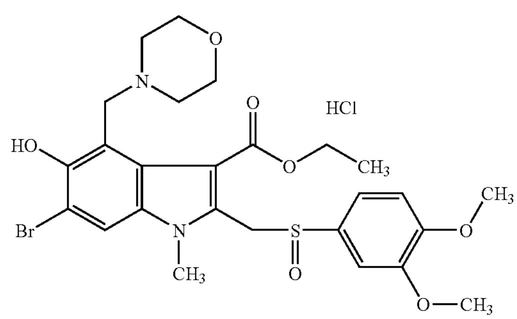 | (CDCl$_3$): 1.44 (t, 3 H), 2.66 (m, 4 H), 3.40 (s, 3 H), 3.71 (s, 3 H), 3.79 (m, 4 H), 3.92 (s, 3 H), 4.27 (d, 2 H), 4.32 (q, 2 H), 4.50 (d, 1 H), 4.71 (d, 1 H), 6.88 (s, 1 H), 6.90 (d, 1 H), 7.01 (d, H), 7.42 (s, 1 H). |
| 61 | Ethyl 1-cyclopropyl-5-hydroxy-4-(morpholinomethyl)-2-[(4-methoxyphenyl)sulfinylmethyl]-1H-indole-3-carboxylate hydrochloride | 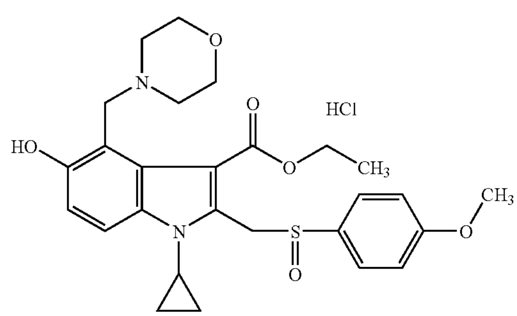 | (CDCl$_3$): 0.91 (m, 2 H), 1.18 (m, 2 H), 1.51 (t, 3 H), 2.22 (m, 1 H), 3.19 (m, 2 H), 3.31 (m, 2 H), 3.83 (s, 3 H), 3.93 (m, 2 H), 4.20 (m, 2 H), 4.42 (q, 2 H), 4.76 (d, 1 H), 5.02 (d, 1 H), 5.18 (m, 1 H), 5.30 (m, 1 H), 6.88 (d, 1 H), 7.24 (m, 3 HHH), 7.52 (d, 1 H), 11.04 (brs, 1 H). |

TABLE 3-continued

| Example No. | Chemical Name | Structure | $^1$H-NMR Data (300 Hz) d (ppm) |
|---|---|---|---|
| 62 | Ethyl 6-bromo-1-cyclopropyl-5-hydroxy-4-(morpholinomethyl)-2-[(2-methyl-3-furyl)sulfinylmethyl]-1H-indole-3-carboxylate | 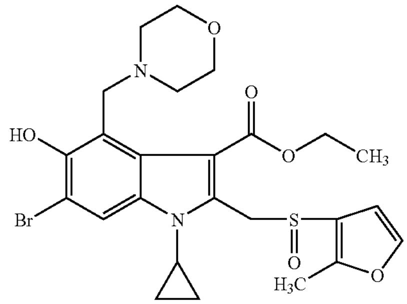 | (CDCl$_3$): 0.98 (m, 1 H), 1.08 (m, 1 H), 1.28 (m, 2 H), 1.44 (t, 3 H), 1.94 (s, 3 H), 2.64 (m, 4 H), 2.83 (m, 1 H), 3.78 (m, 4 H), 4.21 (dd, 2 H), 4.35 (m, 2 H), 4.82 (d, 1 H), 5.00 (d, 1 H), 6.70 (d, 1 H), 7.37 (d, 1 H), 7.69 (s, 1 H). |
| 63 | Ethyl 6-bromo-5-hydroxy-1-methyl-4-(morpholinomethyl)-2-[(1-adamantanyl)sulfinyl]-1H-indole-3-carboxylate | 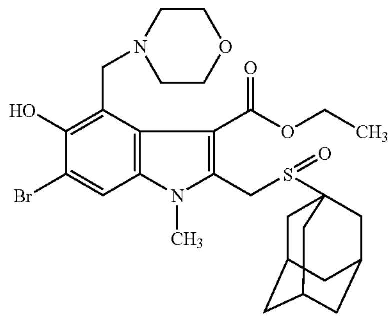 | (DMSO): 1.37 (t, 3 H), 1.80 (m, 6 H), 2.02 (m, 6 H), 2.23 (s, 3 H), 3.35 (m, 4 H), 3.76 (m, 2 H), 3.84 (s, 3 H), 3.98 (m, 2 H), 4.35 (q, 2 H), 4.58 (q, 2 H), 4.95 (dd, 2 H), 8.13 (s, 1 H). |
| 64 | Ethyl 6-bromo-5-hydroxy-1-methyl-4-(morpholinomethyl)-2-[(4-fluorobenzyl)sulfinylmethyl]-1H-indole-3-carboxylate hydrochloride | 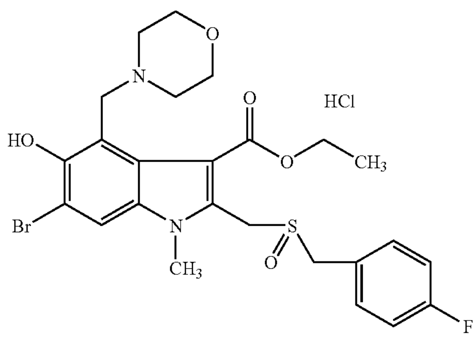 | (DMSO): 1.17 (t, 3 H), 3.28 (m, 2 H), 3.52 (m, 2 H), 3.73 (m, 2 H), 3.79 (s, 3 H), 3.93 (m, 2 H), 4.14 (q, 2 H), 4.31 (d, 1 H), 4.50 (d, 1 H), 4.70 (s, 2 H), 4.94 (d, 1 H), 5.01 (d, 1 H), 7.28 (t, 2 H), 7.48 (dd, 2 H), 8.07 (s, 1 H), 9.42 (br s, 2 H). |
| 65 | Ethyl 6-bromo-5-hydroxy-1-methyl-4-(morpholinomethyl)-2-[(3-trifluoromethylphenyl)sulfonylmethyl]-1H-indole-3-carboxylate hydrochloride | 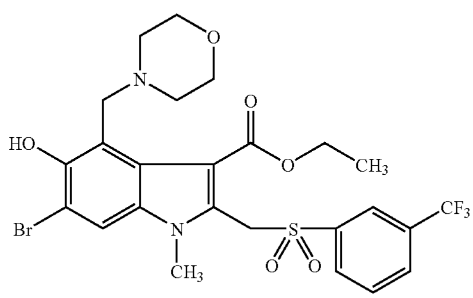 | (CDCl$_3$): 1.32 (t, 3 H), 3.16 (m, 2 H), 3.25 (m, 2 H), 3.83 (s, 3 H), 3.89 (m, 2 H), 4.03 (q, 2 H), 4.29 (m, 2 H), 5.18 (s, 4 H), 7.66 (t, 1 H), 7.76 (s, 1 H), 7.82 (t, 1 H), 7.93 (s, 1 H), 7.95 (s, 1 H). |
| 66 | Ethyl 6-bromo-5-hydroxy-1-methyl-4-(morpholinomethyl)-2-[(4-fluorobenzyl)sulfonylmethyl]-1H-indole-3-carboxylate hydrochloride | 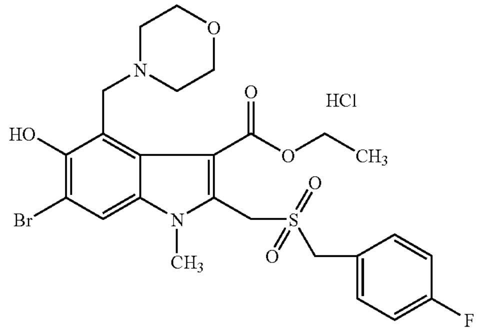 | (CDCl$_3$): 1.42 (t, 3 H), 3.21 (m, 2 H), 3.37 (m, 2 H), 3.78 (s, 3 H), 3.88 (m, 2 H), 4.30~4.44 (m, 4 H), 4.48 (s, 2 H), 5.05 (s, 2 H), 5.26 (d, 2 H), 7.08 (t, 2 H), 7.42 (dd, 2 H), 7.69 (s, 1 H), 11.56 (brs, 1 H). |

TABLE 3-continued

| Example No. | Chemical Name | Structure | $^1$H-NMR Data (300 Hz) d (ppm) |
|---|---|---|---|
| 67 | Ethyl 6-bromo-1-cyclopropyl-5-hydroxy-4-[(4-methyl-1-piperazinyl)methyl]-2-[(3,4-difluorophenyl)sulfinylmethyl]-1H-indole-3-carboxylate dihydrochloride | 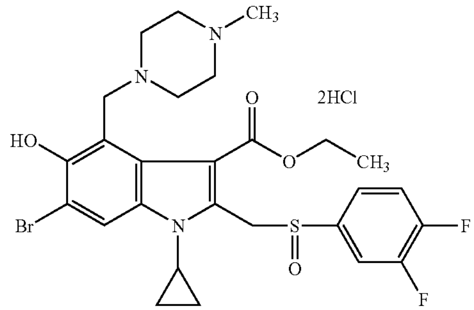 | (DMSO): 1.06 (m, 2 H), 1.26-1.28 (m, 5 H), 2.79 (m, 3 H), 3.17 (s, 2 H), 3.56-3.93 (m, 9 H), 4.22 (m, 2 H), 4.79 (s, 2 H), 7.22 (m, 1 H), 7.41 (m, 1 H), 7.51 (m, 1 H), 7.95 (s, 1 H), 9.87 (s, 1 H), 11.95 (s, 1 H). |
| 68 | Ethyl 6-bromo-1-cyclopropyl-5-hydroxy-4-[(4-methyl-1-piperazinyl)methyl]-2-[(3,4-difluorophenyl)sulfonylmethyl]-1H-indole-3-carboxylate | 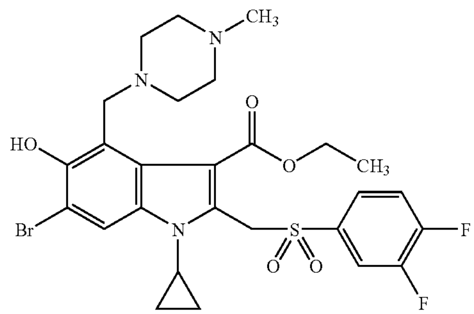 | (CDCl$_3$): 0.86 (m, 2 H), 0.99 (m, 2 H), 1.31 (t, 3 H), 2.36 (s, 3 H), 2.68 (br s, 8 H), 3.41 (m, 1 H), 4.03-4.09 (m, 4 H), 5.23 (s, 2 H), 7.24 (m, 1 H), 7.38-7.46 (m, 2 H), 7.79 (s, 1 H). |
| 69 | Ethyl 6-bromo-1-cyclopropyl-5-hydroxy-4-(1-pyrrolidinylmethyl)-2-[(3-trifluoromethylphenyl)sulfinylmethyl]-1H-indole-3-carboxylate hydrochloride | 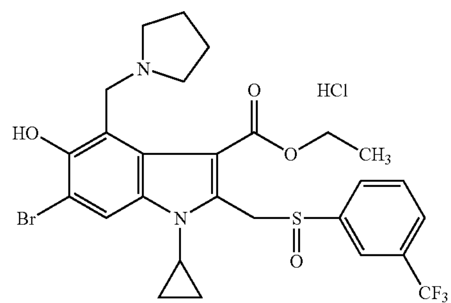 | (CDCl$_3$): 0.92 (m, 1 H), 1.01 (m, 1 H), 1.21 (m, 2 H), 1.48 (t, 3 H), 2.10 (m, 2 H), 2.20 (m, 2 H), 3.16 (m, 2 H), 3.49 (m, 1 H), 3.58 (m, 2 H), 4.38 (q, 2 H), 4.84 (d, 1 H), 5.06 (d, 1 H), 5.26 (d, 2 H), 7.48 (d, 1 H), 7.56 (t, 1 H), 7.73 (s, 1 H), 7.78 (d, 1 H), 7.82 (s, 1 H). |
| 70 | Ethyl 6-bromo-5-hydroxy-1-methyl-4-(1-pyrrolidinylmethyl)-2-[(2-methyl-3-furyl)sulfinylmethyl]-1H-indole-3-carboxylate | 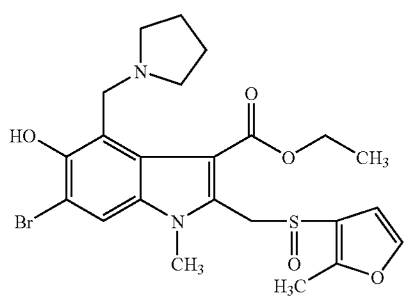 | (CDCl$_3$): 1.40 (t, 3 H), 1.88 (m, 4 H), 2.01 (s, 3 H), 2.73 (m, 4 H), 3.61 (s, 3 H), 4.31 (q, 2 H), 4.37 (dd, 2 H), 4.64 (d, 1 H), 4.77 (d, 1 H), 6.66 (d, 1 H), 7.37 (d, 1 H), 7.44 (s, 1 H). |
| 71 | Ethyl 6-bromo-5-hydroxy-1-methyl-4-(1-pyrrolidinylmethyl)-2-[(2-furylmethyl)sulfinylmethyl]-1H-indole-3-carboxylate | 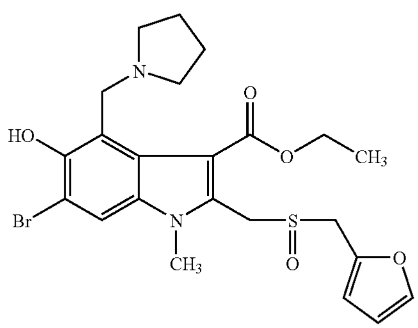 | (CDCl$_3$): 1.38 (t, 3 H), 1.89 (m, 4 H), 2.75 (m, 4 H), 3.72 (s, 3 H), 4.15 (d, 1 H), 4.24-4.37 (m, 5 H), 4.47 (d, 1 H), 4.73 (d, 1 H), 6.45 (d, 1 H), 6.49 (d, 1 H), 7.48 (s, 2 H). |

TABLE 3-continued

| Example No. | Chemical Name | Structure | $^1$H-NMR Data (300 Hz) d (ppm) |
|---|---|---|---|
| 72 | Ethyl 5-hydroxy-1-methyl-4-(1-pyrrolidinylmethyl)-2-[(3-methoxyphenyl)sulfonylmethyl]-1H-indole-3-carboxylate hydrochloride | 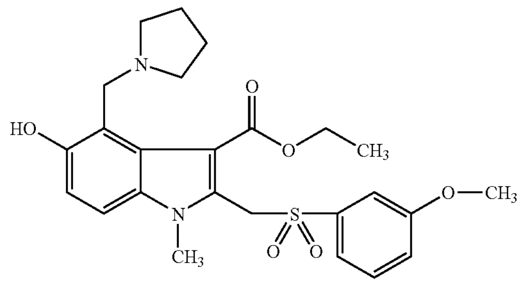 | (DMSO): 1.31 (t, 3 H), 1.90 (m, 2 H), 2.03 (m, 2 H), 3.25 (m, 2 H), 3.45 (m, 2 H), 3.66 (s, 3 H), 3.68 (s, 3 H), 4.15 (q, 2 H), 4.80 (d, 2 H), 5.39 (s, 2 H), 7.09~7.13 (m, 2 H), 7.31~7.36 (m, 2 H), 7.56 (t, 2 H), 9.15 (br.s, 1 H), 10.18 (s, 1 H). |
| 73 | Ethyl 5-hydroxy-1-methyl-4-(1-pyrrolidinylmethyl)-2-[(4-methylphenyl)sulfonylmethyl]-1H-indole-3-carboxylate | 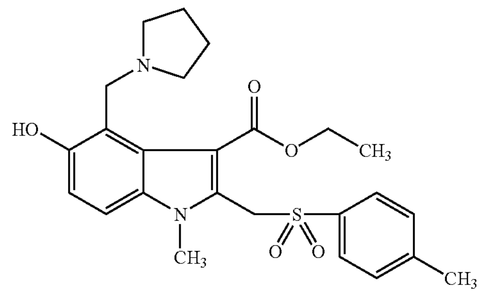 | (CDCl$_3$): 1.29 (t, 3 H), 1.88 (s, 4 H), 2.44 (s, 3 H), 2.71 (s, 4 H), 3.78 (s, 3 H), 4.00 (q, 2 H), 4.27 (s, 2 H), 5.09 (s, 2 H), 6.96 (d, 1 H), 7.19 (d, 1 H), 7.25 (d, 2 H), 7.54 (d, 2 H). |
| 74 | Ethyl 6-bromo-1-cyclopropyl-5-hydroxy-4-(piperidinomethyl)-2-[(2-furrylmethyl)sulfinylmethyl]-1H-indole-3-carboxylate | 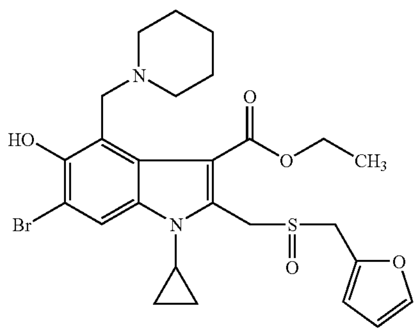 | (CDCl$_3$): 0.91 (m, 1 H), 1.18 (m, 4 H), 1.37 (t, 3 H), 1.68 (m, 5 H), 2.00~2.50 (brs, 4 H), 3.20 (m, 1 H), 4.20 (dd, 2 H), 4.33 (q, 2 H), 4.58 (d, 1 H), 4.68 (d, 1 H), 6.44 (d, 1 H), 6.48 (d, 1 H), 7.48 (s, 1 H), 7.73 (s, 1 H). |
| 75 | Ethyl 6-bromo-5-hydroxy-1-methyl-4-(piperidinomethyl)-2-[(3-fluorobenzyl)sulfinylmethyl]-1H-indole-3-carboxylate | 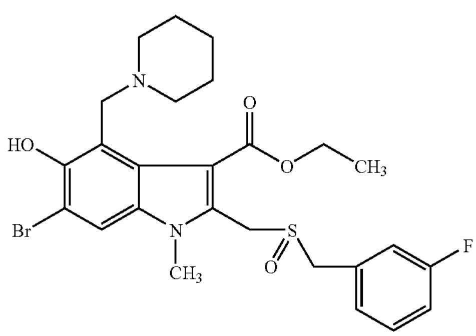 | (CDCl$_3$): 1.29 (t, 3 H), 1.37 (m, 1 H), 1.78 (m, 3 H), 2.21 (m, 2 H), 2.95 (m, 2 H), 3.36 (m, 2 H), 3.72 (s, 3 H), 4.13 (d, 1 H), 4.15~4.35 (m, 3 H), 4.32 (d, 1 H), 4.74 (d, 1 H), 5.21 (s, 2 H), 7.08~7.20 (m, 3 H), 7.40 (dd, 1 H), 7.62 (s, 1 H), 10.26 (brs, 1 H). |
| 76 | Ethyl 1-cyclopropyl-5-hydroxy-4-(piperidinomethyl)-2-[(3,4-dimethoxyphenyl)sulfinyl methyl]-1H-indole-3-carboxylate hydrochloride | 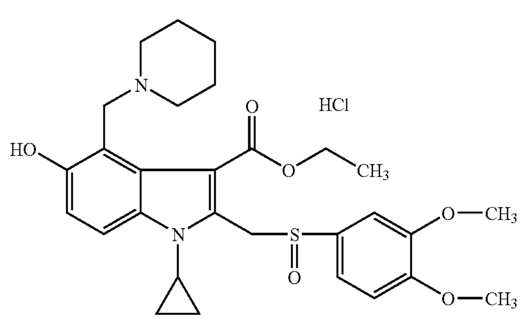 | (CDCl$_3$): 0.88 (m, 2 H), 1.13 (m, 2 H), 1.50~1.55 (m, 5 H), 1.87 (m, 2 H), 2.07 (m, 2 H), 2.77 (m, 1 H), 3.34 (m, 2 H), 3.49 (s, 3 H), 3.90 (s, 3 H), 4.41 (q, 2 H), 4.76 (d, 1 H), 5.01 (m, 1 H), 5.06 (m, 2 H), 6.66 (s, 1 H), 6.82 (s, 2 H), 7.36 (d, 1 H), 7.50 (d, 1 H), 9.78 (brs, 1 H). |

TABLE 3-continued

| Example No. | Chemical Name | Structure | $^1$H-NMR Data (300 Hz) d (ppm) |
|---|---|---|---|
| 77 | Ethyl 5-hydroxy-1-methyl-4-(piperidinomethyl)-2-[(3-furylmethyl)sulfinylmethyl]-1H-indole-3-carboxylate hydrochloride | 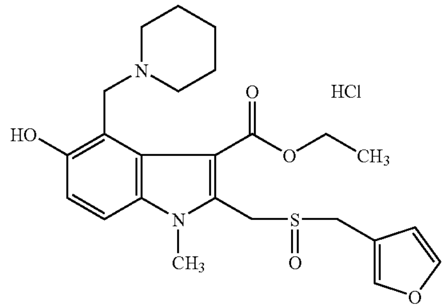 | (DMSO): 1.25 (t, 3 H), 1.45 (m, 1 H), 1.63~1.79 (m, 5 H), 3.06 (m, 2 H), 3.36 (m, 2 H), 3.80 (s, 3 H), 4.19 (q, 2 H), 4.42 (d, 1 H), 4.59 (d, 1 H), 4.69~4.86 (m, 4 H), 6.55 (m, 1 H), 7.10 (d, 1 H), 7.59 (d, 1 H), 7.77 (d, 1 H), 8.48 (br s, 1 H), 10.13 (d, 1 H). |
| 78 | Ethyl 6-bromo-1-cyclopropyl-5-hydroxy-4-(piperidinomethyl)-2-[(3,4-methoxyphenyl)sulfonylmethyl]-1H-indole-3-carboxylate | 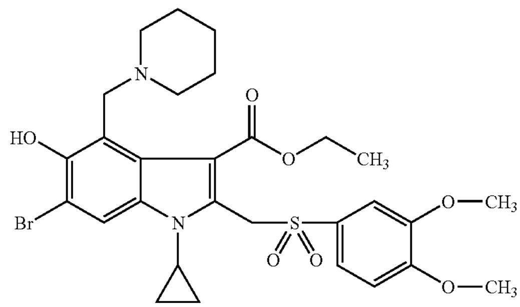 | (CDCl$_3$): 0.94 (m, 2 H), 1.27 (m, 2 H), 1.32 (t, 3 H), 1.67 (m, 6 H), 2.25~2.45 (brs, 4 H), 3.15 (m, 1 H), 3.56 (s, 3 H), 3.90 (d 1 H), 3.93 (s, 3 H), 4.00~4.07 (m, 3 H), 5.20 (s, 2 H), 6.78 (s, 1 H), 6.87 (d, 1 H), 7.29 (m, 1 H), 7.72 (s, 1 H). |

TABLE 4

| Example No. | Chemical Name | Structure | MS m/z |
|---|---|---|---|
| 79 | Ethyl 6-bromo-1-cyclopropyl-4-[(dimethylamino)methyl]-5-hydroxy-2-[(4-trifluoromethylphenyl)sulfinylmethyl]-1H-indole-3-carboxylate | 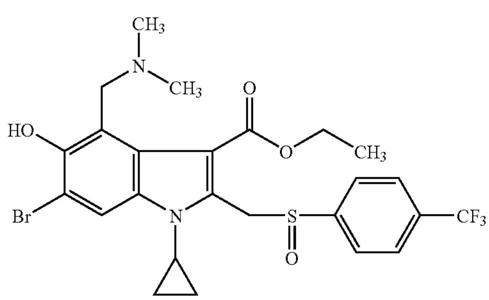 | 588.8, 586.8 [M + H] |
| 80 | Ethyl 6-bromo-4-[(dimethylamino)methyl]-5-hydroxy-1-methyl-2-[(4-fluorobenzyl)sulfinylmethyl]-1H-indole-3-carboxylate | 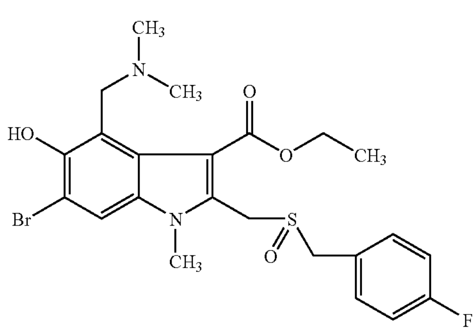 | 527.2, 525.3 [M + H] |

TABLE 4-continued

| Example No. | Chemical Name | Structure | MS m/z |
|---|---|---|---|
| 81 | Ethyl 6-bromo-4-[(dimethylamino)methyl]-5-hydroxy-1-methyl-2-[(3-fluorobenzyl)sulfinylmethyl]-1H-indole-3-carboxylate | 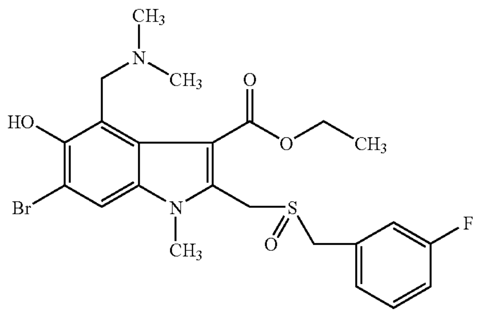 | 527.0, 525.0 [M + H] |
| 82 | Ethyl 6-bromo-5-hydroxy-1-methyl-4-(1-pyrrolidinylmethyl)-2-[(4-trifluoromethylphenyl)sulfonylmethyl]-1H-indole-3-carboxylate | 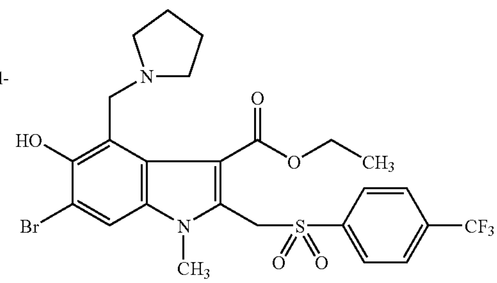 | 605.0, 603.0 [M + H] |
| 83 | Ethyl 6-bromo-1-cyclopropyl-5-hydroxy-4-(1-pyrrolidinylmethyl)-2-[(3-trifluoromethylphenyl)sulfonylmethyl]-1H-indole-3-carboxylate | 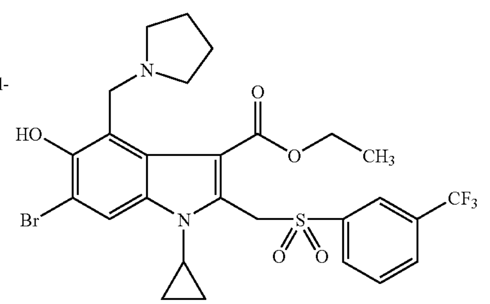 | 631.0, 629.0 [M + H] |
| 84 | Ethyl 6-bromo-5-hydroxy-1-methyl-4-(1-pyrrolidinylmethyl)-2-[(4-fluorobenzyl)sulfonylmethyl]-1H-indole-3-carboxylate | 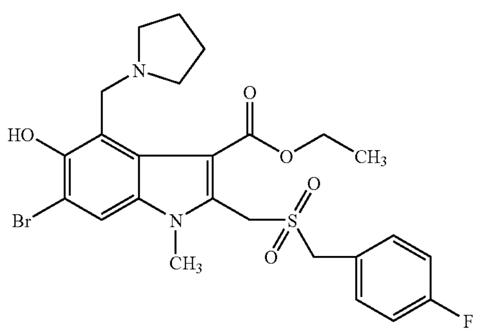 | 569.1, 567.1 [M + H] |
| 85 | Ethyl 1-cyclopropyl-5-hydroxy-4-(1-pyrrolidinylmethyl)-2-[(2-furylmethyl)]sulfonylmethyl]-1H-indole-3-carboxylate | 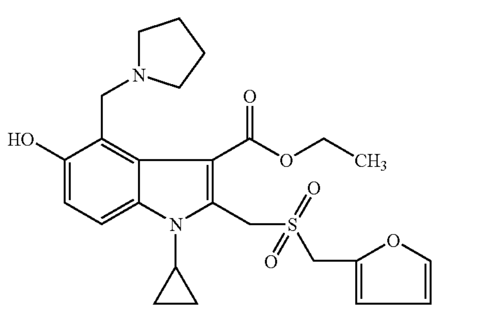 | 487.2 [M + H] |

TABLE 4-continued

| Example No. | Chemical Name | Structure | MS m/z |
|---|---|---|---|
| 86 | Ethyl 6-bromo-5-hydroxy-1-methyl-4-(piperidinomethyl)-2-[(4-fluorobenzyl)sulfinylmethyl]-1H-indole-3-carboxylate | 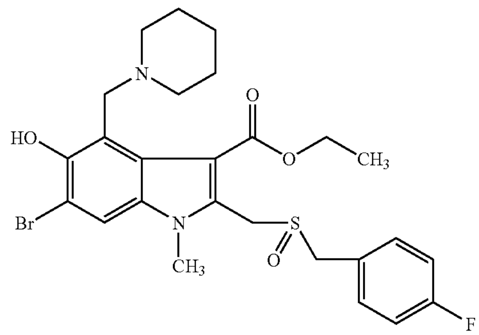 | 567.1, 565.1 [M + H] |
| 87 | Ethyl 6-bromo-5-hydroxy-1-methyl-4-(morpholinomethyl)-2-[(3-fluorobenzyl)sulfinylmethyl]-1H-indole-3-carboxylate | 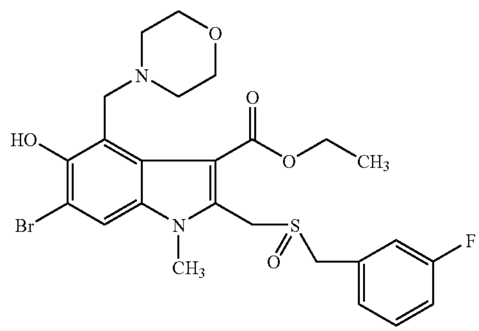 | 569.3, 567.3 [M + H] |

General Procedure 4 for the Preparation (Scheme D)

Step A: The Preparation of Compound D-1

Compound D-1 was obtained according to general procedure 1, 2 or 3.

Step B: The Preparation of Compound D-2

To a solution of 0.02 mol of compound D-1 in 80 mL of ethanol/water (1:1, V/V) was added 0.05 mol of $HNR_3R_4$ (guanidine, arylamines, or arylheterocylces containing nitrogen) or $HS(CH_2)_mR_8$. After being stirred at 80° C. for 6-8 h, the solvent was evaporated in vacuo, extracted with methylene dichloride. The organic phase was dried, and evaporated. The residue was recrystallized from appropriate solvent, or chromatographed over silica gel to give 50-80% yield of compound D-2.

Following the general procedure 4, the compounds of Examples 88-194 were synthesized respectively (Table 5, 6).

TABLE 5

| Example No. | Chemical Name | Structure | $^1$H-NMR Data (300 Hz) d (ppm) |
|---|---|---|---|
| 88 | Ethyl 6-bromo-5-hydroxy-4-[(1-imidazolyl)methyl]-1-methyl-2-[(2,4-dimethylphenyl)thiomethyl]-1H-indole-3-carboxylate | 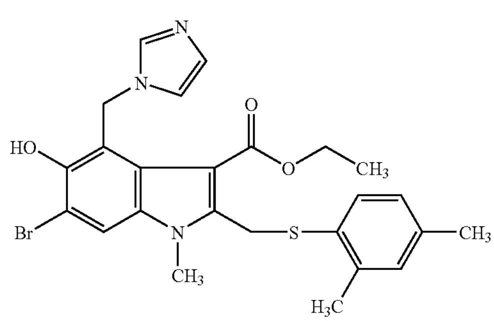 | (CDCl$_3$): 1.27 (t, 3 H), 2.23 (s, 3 H), 2.31 (s, 3 H), 3.56 (s, 3 H), 4.15 (q, 2 H), 4.41 (s, 2 H), 5.98 (s, 2 H), 6.90 (d, 1 H), 7.03 (s, 1 H), 7.08 (s, 1 H), 7.13 (s, 1 H), 7.18 (s, 1 H), 7.51 (s, 1 H), 7.99 (br s, 1 H). |

TABLE 5-continued

| Example No. | Chemical Name | Structure | ¹H-NMR Data (300 Hz) d (ppm) |
|---|---|---|---|
| 89 | Ethyl 6-bromo-5-hydroxy-4-[(1-imidazolyl)methyl]-1-methyl-2-[(4-nitrophenyl)thiomethyl]-1H-indole-3-carboxylate | 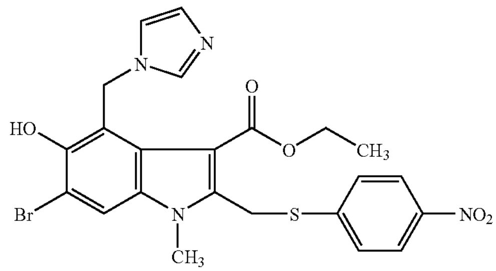 | (CDCl₃): 1.25 (t, 3 H), 3.75 (s, 3 H), 4.28 (q, 2 H), 4.75 (s, 2 H), 6.01 (s, 2 H), 7.09 (s, 1 H), 7.18 (s, 1 H), 7.43 (d, 2 H), 7.58 (s, 1 H), 7.98 (s, 1 H), 8.18 (d, 2 H). |
| 90 | Ethyl 6-bromo-5-hydroxy-4-[(1-imidazolyl)methyl]-1-cyclopropyl-2-[(4-thiazolylmethyl)thiomethyl]-1H-indole-3-carboxylate | 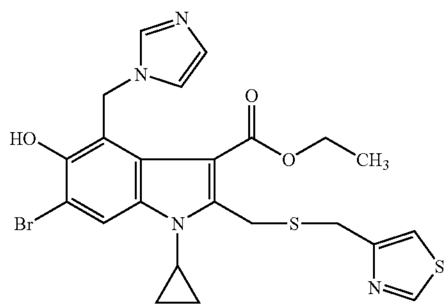 | (CDCl₃): 1.02 (m, 2 H), 1.18 (m, 2 H), 1.31 (t, 3 H), 3.20 (m, 1 H), 3.91 (s, 2 H), 4.31 (q, 2 H), 4.39 (s, 2 H), 5.83 (s, 2 H), 6.92 (s, 1 H), 6.95 (s, 1 H), 7.00 (d, 1 H), 7.52 (s, 1 H), 7.71 (s, 1 H), 8.69 (d, 1 H). |
| 91 | Ethyl 6-bromo-1-cyclopropyl-5-hydroxy-4-[(1-imidazolyl)methyl]-2-(benzylthiomethyl)-1H-indole-3-carboxylate | 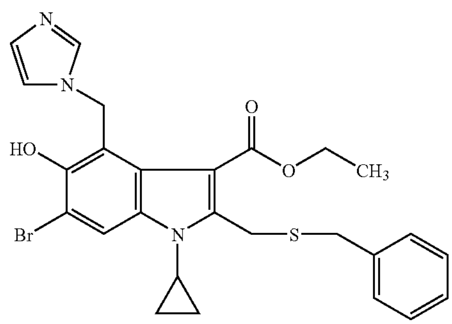 | (CDCl₃): 1.00 (m, 2 H), 1.07 (m, 2 H), 1.28 (t, 3 H), 3.09 (m, 1 H), 3.75 (s, 2 H), 4.24 (dd, 2 H), 4.27 (s, 2 H), 5.91 (s, 2 H), 7.00 (s, 1 H), 7.13 (d, 1 H), 7.21~7.28 (m, 5 H), 7.75 (s, 1 H), 7.86 (s, 1 H). |
| 92 | Ethyl 6-bromo-5-hydroxy-4-[(1-imidazolyl)methyl]-1-methyl-2-[(4-fluorobenzyl)thiomethyl]-1H-indole-3-carboxylate | 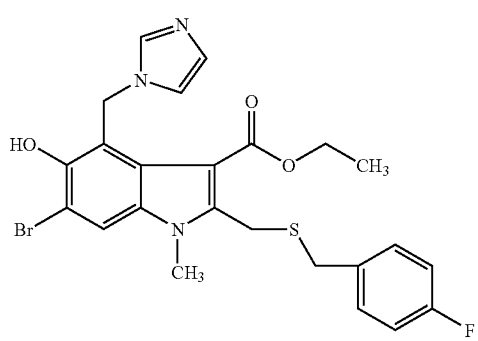 | (DMSO): 1.15 (t, 3 H), 3.68 (s, 3 H), 3.80 (s, 2 H), 4.16 (q, 2 H), 4.21 (s, 2 H), 5.75 (s, 2 H), 6.75 (s, 1 H), 6.86 (s, 1 H), 7.07 (t, 2 H), 7.29 (dd, 2 H), 7.39 (s, 1 H), 7.84 (s, 1 H), 9.07 (brs, 1 H). |
| 93 | Ethyl 6-bromo-1-cyclopropyl-5-hydroxy-4-[(1-imidazolyl)methyl]-2-[(3-chlorobenzyl)thiomethyl]-1H-indole-3-carboxylate | 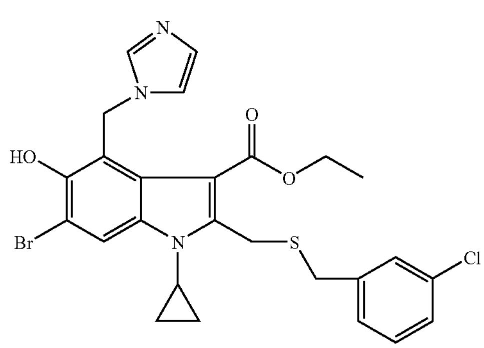 | (CDCl₃): 1.01 (m, 2 H), 1.14 (m, 2 H), 1.27 (t, 3 H), 3.14 (m, 1 H), 3.69 (s, 2 H), 4.25 (m, 4 H), 5.82 (s, 2 H), 6.92 (s, 1 H), 6.94 (s, 1 H), 7.11 (m, 3 H), 7.26 (s, 1 H), 7.53 (s, 1 H), 7.71 (s, 1 H). |

TABLE 5-continued

| Example No. | Chemical Name | Structure | $^1$H-NMR Data (300 Hz) d (ppm) |
|---|---|---|---|
| 94 | Ethyl 6-bromo-5-hydroxy-4-[(1-imidazolyl)methyl]-1-methyl-2-[(benzo[d]imidazol-2-yl)thiomethyl]-1H-indole-3-carboxylate hydrochloride | 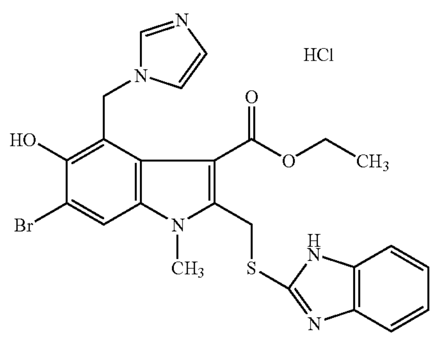 | (DMSO): 1.08 (t, 3 H), 3.99 (s, 3 H), 4.02 (q, 2 H), 5.18 (s, 2 H), 5.86 (s, 2 H), 7.17 (s, 1 H), 7.37 (m, 2 H), 7.46 (s, 1 H), 7.51 (s, 1 H), 7.64 (m, 2 H), 8.06 (s, 1 H), 8.88 (s, 1 H). |
| 95 | Ethyl 6-bromo-5-hydroxy-1-methyl-4-[(2-methyl-1-imidazolyl)methyl]-2-[(3-methoxy)phenylthiomethyl]-1H-indole-3-carboxylate | 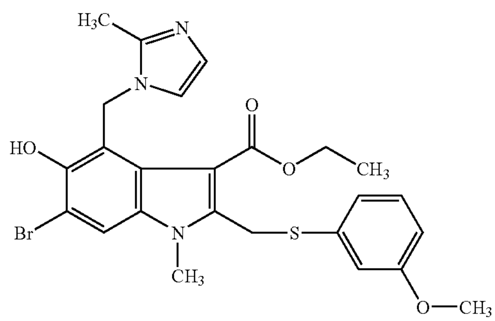 | (DMSO): 1.30 (t, 3 H), 2.34 (s, 3 H), 3.28 (s, 3 H), 3.69 (s, 3 H), 3.72 (s, 3 H), 4.19 (q, 2 H), 4.81 (s, 2 H), 6.82 (m, 2 H), 6.87 (s, 1 H), 6.92 (m, 1 H), 7.21 (m, 1 H), 7.56 (s, 1 H), 7.75 (s, 1 H), 9.85 (br s, 1 H). |
| 96 | Ethyl 6-bromo-5-hydroxy-1-methyl-4-[(2-methyl-1-imidazolyl)methyl]-2-[(3-trifluoromethylphenyl)thiomethyl]-1H-indole-3-carboxylate | 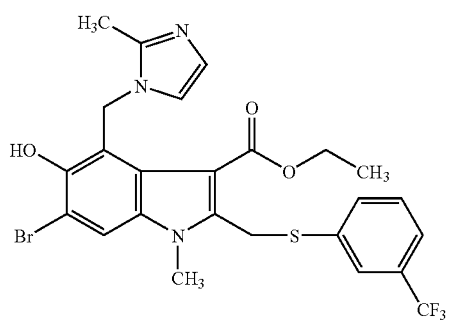 | (DMSO): 1.03 (t, 3 H), 2.31 (s, 3 H), 3.77 (s, 3 H), 3.97 (q, 2 H), 4.75 (s, 2 H), 5.51 (s, 2 H), 6.25 (s, 1 H), 6.51 (s, 1 H), 7.51 (t, 1 H), 7.61 (m, 3 H), 7.90 (s, 1 H). |
| 97 | Ethyl 6-bromo-1-cyclopropyl-5-hydroxy-4-[(2-methyl-1-imidazolyl)methyl]-2-[(4-thiazolylmethyl)thiomethyl]-1H-indole-3-carboxylate | 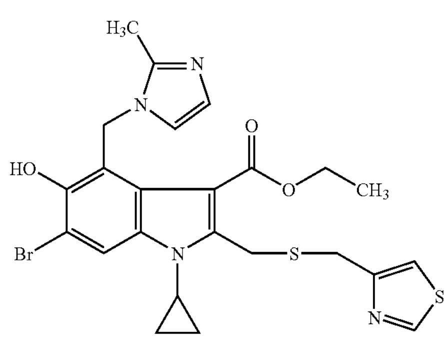 | (DMSO): 1.06 (m, 2 H), 1.13 (t, 5 H), 2.34 (s, 3 H), 3.21 (m, 1 H), 3.93 (s, 2 H), 4.09 (q, 2 H), 4.35 (s, 2 H), 5.50 (s, 2 H), 6.34 (d, 1 H), 6.56 (s, 1 H), 7.48 (d, 1 H), 7.82 (s, 1 H), 9.04 (s, 1 H). |

TABLE 5-continued

| Example No. | Chemical Name | Structure | $^1$H-NMR Data (300 Hz) d (ppm) |
|---|---|---|---|
| 98 | Ethyl 6-bromo-5-hydroxy-1-methyl-4-[(2-methyl-1-imidazolyl)methyl]-2-[(2-methylphenyl)thiomethyl]-1H-indole-3-carboxylate | 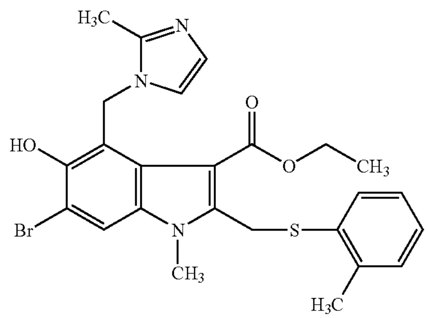 | (CDCl$_3$): 1.16 (t, 3 H), 2.27 (s, 3 H), 2.46 (s, 3 H), 3.63 (s, 3 H), 4.06 (q, 2 H), 4.79 (s, 2 H), 5.62 (s, 2 H), 6.49 (s, 1 H), 6.61 (s, 1 H), 7.12 (m, 2 H), 7.18 (m, 2 H), 7.51 (s, 1 H). |
| 99 | Ethyl 6-bromo-1-cyclopropyl-5-hydroxy-4-[(2-methyl-1-imidazolyl)methyl]-2-[(3,4-difluorophenyl)thiomethyl]-1H-indole-3-carboxylate | 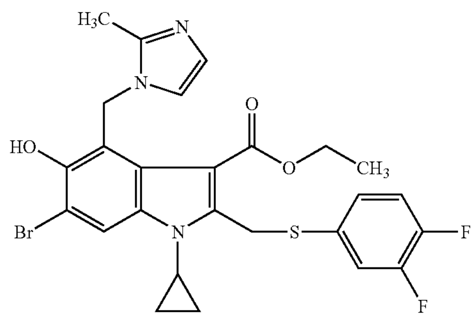 | (CDCl$_3$): 1.12 (m, 2 H), 1.17 (t, 3 H), 1.29 (m, 2 H), 2.44 (s, 3 H), 3.13 (m, 1 H), 4.09 (q, 2 H), 4.66 (s, 2 H), 5.55 (s, 2 H), 6.43 (d, 1 H), 6.60 (d, 1 H), 6.99~7.05 (m, 2 H), 7.13~7.17 (m, 1 H), 7.80 (s, 1 H). |
| 100 | Ethyl 6-bromo-5-hydroxy-1-methyl-4-[(2-methyl-1-imidazolyl)methyl]-2-[(4-fluorobenzyl)thiomethyl]-1H-indole-3-carboxylate | 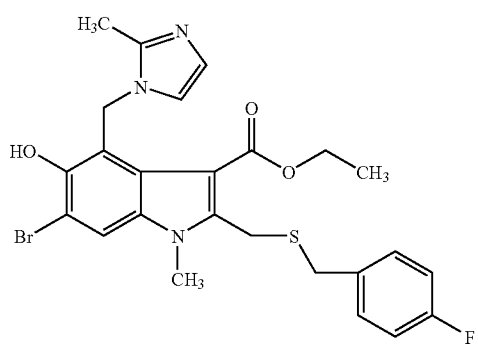 | (DMSO): 1.07 (t, 3 H), 2.33 (s, 3 H), 3.70 (s, 3 H), 3.79 (s, 2 H), 4.05 (q, 2 H), 4.21 (s, 2 H), 5.53 (s, 2 H), 6.31 (d, 1 H), 6.51 (d, 1 H), 7.10 (t, 2 H), 7.31 (dd, 2 H), 7.86 (s, 1 H). |
| 101 | Ethyl 6-bromo-5-hydroxy-1-methyl-4-[(2-methyl-1-imidazolyl)methyl]-2-[(phenoxyethyl)thiomethyl]-1H-indole-3-carboxylate | 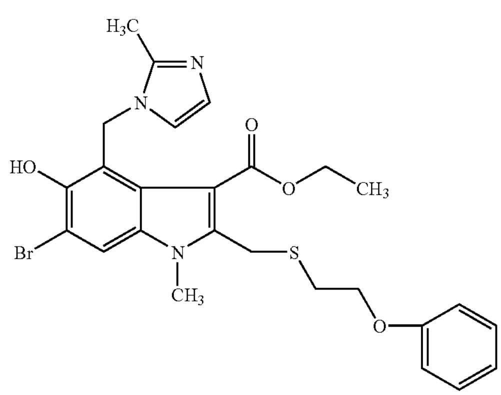 | (DMSO): 1.12 (t, 3 H), 2.33 (s, 3 H), 2.89 (t, 2 H), 3.79 (s, 3 H), 4.02 (t, 2 H), 4.11 (q, 2 H), 4.35 (s, 2 H), 5.52 (s, 2 H), 6.30 (s, 1 H), 6.50 (s, 1 H), 6.85 (d, 2 H), 6.92 (t, 1 H), 7.25 (t, 2 H), 7.89 (s, 1 H), 8.90 (brs, 1 H). |

TABLE 5-continued

| Example No. | Chemical Name | Structure | $^1$H-NMR Data (300 Hz) d (ppm) |
|---|---|---|---|
| 102 | Ethyl 6-bromo-4-(guanidinylmethyl)-5-hydroxy-1-methyl-2-(phenylthiomethyl)-1H-indole-3-carboxylate | 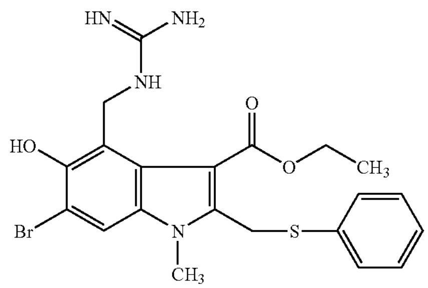 | (CDCl$_3$): 1.16 (t, 3 H), 2.72 (s, 2 H), 3.33 (s, 3 H), 4.03 (m, 2 H), 4.34 (s, 2 H), 4.62 (s, 2 H), 6.34 (s, 2 H), 7.12-7.35 (m, 7 H). |
| 103 | Ethyl 1-cyclopropyl-4-(guanidinylmethyl)-5-hydroxy-2-[(3-methoxyphenyl)thiomethyl]-1H-indole-3-carboxylate hydrochloride | 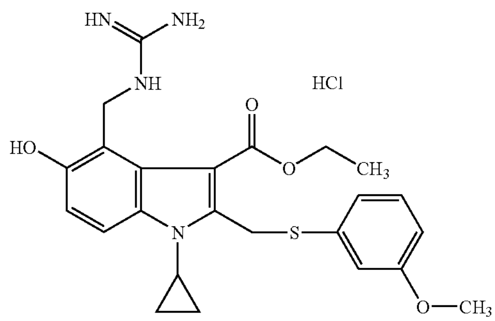 | (DMSO): 1.03 (m, 2 H), 1.19 (m, 2 H), 1.24 (t, 3 H), 2.09 (s, 3 H), 3.14 (m, 1 H), 3.69 (s, 3 H), 4.19 (q, 2 H), 4.63 (d, 2 H), 4.78 (s, 2 H), 6.87 (m, 3 H), 6.85 (d, 1 H), 7.01 (d, 1 H), 7.24 (m, 2 H), 7.52 (d, 1 H), 9.89 (s, 1 H). |
| 104 | Ethyl 6-bromo-4-(guanidinylmethyl)-5-hydroxy-1-methyl-2-(benzylthiomethyl)-1H-indole-3-carboxylate | 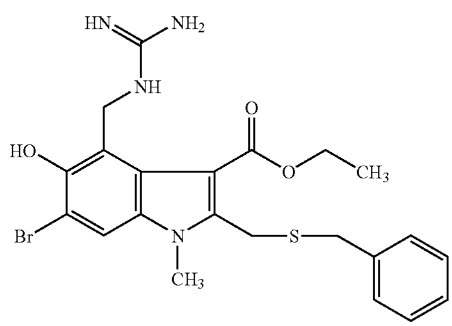 | (DMSO): 1.18 (t, 3 H), 3.54 (s, 3 H), 3.81 (s, 2 H), 4.14 (m, 4 H), 4.51 (s, 2 H), 6.71 (brs, 3 H), 7.26 (m, 5 H), 7.45 (s, 1 H). |
| 105 | Ethyl 6-bromo-1-cyclopropyl-4-(guanidinylmethyl)-5-hydroxy-2-[(4-trifluoromethoxyphenyl)thiomethyl]-1H-indole-3-carboxylate | 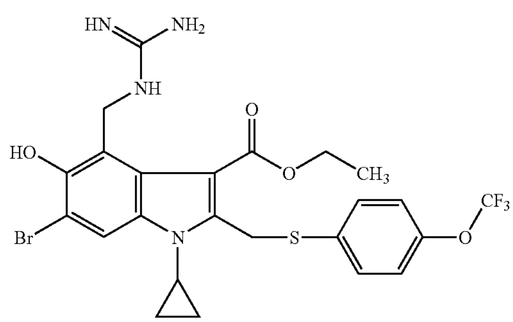 | (DMSO): 0.99 (m, 2 H), 1.14 (m, 2 H), 1.21 (t, 3 H), 2.98 (m, 1 H), 4.19 (q, 2 H), 4.51 (d, 2 H), 7.76 (s, 2 H), 6.59 (s, 2 H), 6.94 (s, 1 H), 7.35 (d, 1 H), 7.51 (d, 1 H), 7.55 (s, 1 H). |
| 106 | Ethyl 6-bromo-1-cyclopropyl-5-hydroxy-4-[(1H-1,2,4-triazol-1-yl)methyl]-2-[(2-methoxyphenyl)thiomethyl]-1H-indole-3-carboxylate | 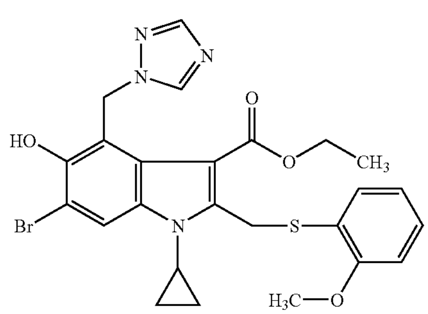 | (CDCl$_3$): 1.06 (m, 2 H), 1.18 (m, 2 H), 1.32 (t, 3 H), 2.93 (m, 1 H), 3.67 (s, 3 H), 4.20 (q, 2 H), 4.66 (s, 2 H), 6.04 (s, 2 H), 6.79 (m, 1 H), 6.84 (m, 1 H), 7.24 (m, 1 H), 7.31 (m, 1 H), 7.81 (s, 1 H), 7.97 (s, 1 H), 8.61 (s, 1 H), 9.23 (br s, 1 H). |

TABLE 5-continued

| Example No. | Chemical Name | Structure | $^1$H-NMR Data (300 Hz) d (ppm) |
|---|---|---|---|
| 107 | Ethyl 6-bromo-5-hydroxy-1-methyl-4-[(1H-1,2,4-triazol-1-yl)methyl]-2-[(4-methylphenyl)thiomethyl]-1H-indole-3-carboxylate | 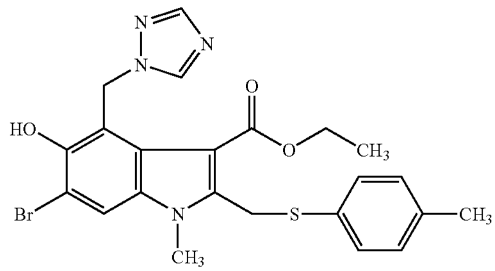 | (CDCl$_3$): 1.36 (t, 3 H), 2.36 (s, 3 H), 3.53 (s, 3 H), 4.25 (q, 2 H), 4.51 (s, 2 H), 6.11 (s, 2 H), 7.06 (d, 2 H), 7.19 (d, 2 H), 7.54 (s, 1 H), 7.98 (s, 1 H), 8.65 (s, 1 H), 9.56 (br s, 1 H). |
| 108 | Ethyl 6-bromo-1-cyclopropyl-5-hydroxy-4-[(1H-1,2,4-triazol-1-yl)methyl]-2-[(2-pyridyl)thiomethyl]-1H-indole-3-carboxylate | 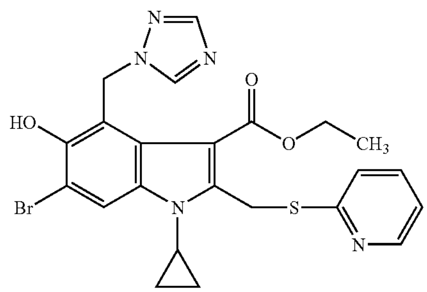 | (CDCl$_3$): 1.11 (m, 2 H), 1.26 (m, 2 H), 1.37 (t, 3 H), 3.20 (m, 1 H), 4.40 (q, 2 H), 5.12 (s, 2 H), 6.07 (s, 2 H), 7.04 (m, 1 H), 7.15 (m, 1 H), 7.50 (m, 1 H), 7.83 (s, 1 H), 7.95 (s, 1 H), 8.45 (m, 1 H), 8.65 (s, 1 H), 9.48 (brs, 1 H). |
| 109 | Ethyl 5-hydroxy-4-[(1H-1,2,4-triazol-1-yl)methyl]-2-[(4-methylphenyl)thiomethyl]-1H-indole-3-carboxylate | 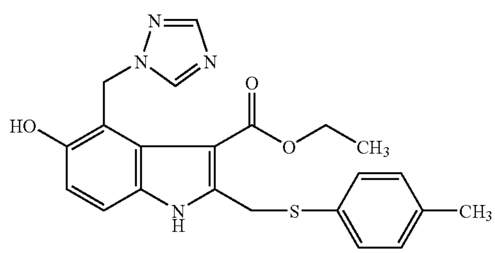 | (CDCl$_3$): 1.42 (t, 3 H), 2.28 (s, 3 H), 4.38 (q, 2 H), 4.55 (s, 2 H), 6.17 (s, 2 H), 7.00 (d, 1 H), 7.04 (d, 2 H), 7.14 (d, 2 H), 7.21 (d, 1 H), 7.94 (s, 1 H), 8.73 (s, 1 H), 9.16 (brs, 1 H). |
| 110 | Ethyl 1-cyclopropyl-5-hydroxy-4-[(1H-1,2,4-triazol-1-yl)methyl]-2-(phenylthiomethyl)-1H-indole-3-carboxylate | 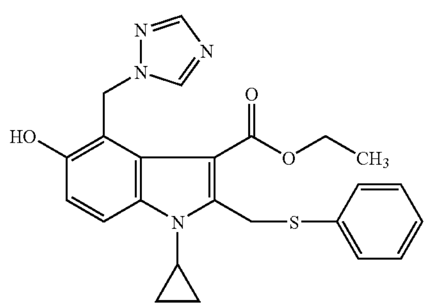 | (CDCl$_3$): 1.05 (m, 2 H), 1.16 (m, 2 H), 1.35 (t, 3 H), 2.92 (m, 1 H), 4.25 (q, 4 H), 4.75 (s, 2 H), 6.03 (s, 2 H), 7.04 (d, 1 H), 7.32 (m, 5 H), 7.52 (d, 1 H), 7.96 (s, 1 H), 8.71 (s, 1 H), 9.45 (br s, 1 H). |
| 111 | Ethyl 6-bromo-5-hydroxy-1-methyl-4-[(1H-tetrazol-1-yl)methyl]-2-[(4-methoxyphenyl)thiomethyl]-1H-indole-3-carboxylate | 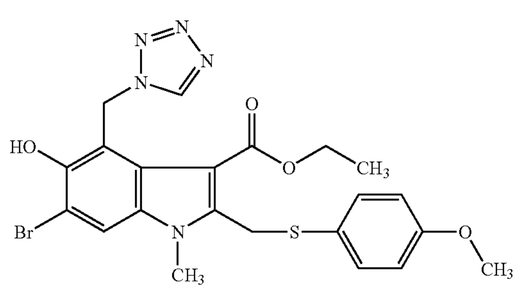 | (CDCl$_3$): dppm: 1.24 (t, 3 H), 3.57 (s, 3 H), 3.80 (s, 3 H), 4.10 (q, 2 H), 4.44 (s, 2 H), 6.07 (br s, 1 H), 6.32 (s, 2 H), 6.75 (d, 2 H), 7.16 (d, 2 H), 7.54 (s, 1 H), 8.61 (s, 1 H). |

TABLE 5-continued

| Example No. | Chemical Name | Structure | ¹H-NMR Data (300 Hz) d (ppm) |
|---|---|---|---|
| 112 | Ethyl 6-bromo-1-cyclopropyl-5-hydroxy-4-[(1H-tetrazol-1-yl)methyl]-2-[(4-methylphenyl)thiomethyl]-1H-indole-3-carboxylate | 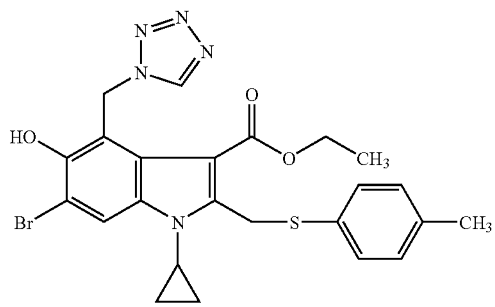 | (CDCl$_3$): 1.09 (m, 2 H), 1.24 (m, 2 H), 1.26 (t, 3 H), 2.35 (s, 3 H), 4.15 (q, 2 H), 4.68 (s, 2 H), 6.30 (s, 2 H), 7.06 (d, 2 H), 7.18 (d, 2 H), 7.83 (s, 2 H), 8.61 (s, 1 H). |
| 113 | Ethyl 6-bromo-5-hydroxy-1-methyl-4-[(1H-tetrazol-1-yl)methyl]-2-[(4-fluorophenyl)thiomethyl]-1H-indole-3-carboxylate | 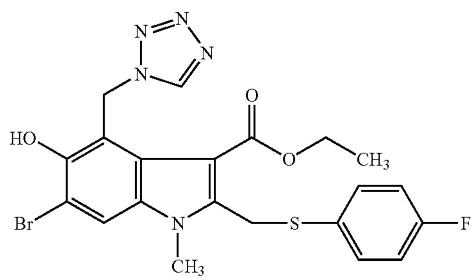 | (CDCl$_3$): 1.25 (t, 3 H), 3.61 (s, 3 H), 4.15 (q, 2 H), 4.50 (s, 2 H), 6.34 (s, 2 H), 6.96 (t, 2 H), 7.24 (d, 2 H), 7.56 (s, 1 H), 8.63 (s, 1 H). |
| 114 | Ethyl 1-cyclopropyl-5-hydroxy-4-[(1H-tetrazol-1-yl)methyl]-2-(phenylthiomethyl)-1H-indole-3-carboxylate | 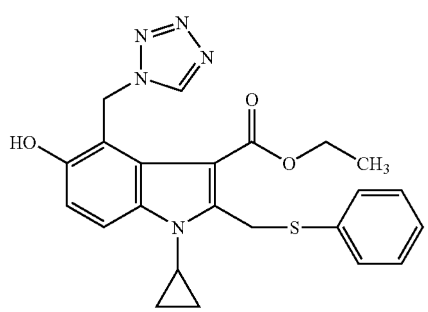 | (CDCl$_3$): 1.08 (m, 2 H), 1.19 (m, 2 H), 1.29 (t, 3 H), 2.97 (m, 1 H), 4.20 (q, 2 H), 4.75 (s, 2 H), 6.25 (s, 2 H), 6.99 (d, 1 H), 7.28 (m, 5 H), 7.55 (d, 1 H), 8.97 (s, 1 H). |
| 115 | Ethyl 6-bromo-5-hydroxy-4-[(4,5-dicyano-1-imidazolyl)methyl]-1-methyl-2-[(3-methoxyphenyl)thiomethyl]-1H-indole-3-carboxylate | 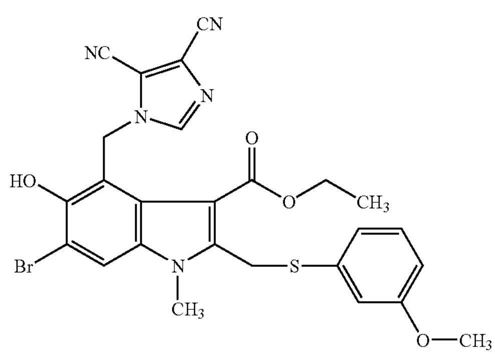 | (CDCl$_3$): 1.27 (t, 3 H), 3.67 (s, 3 H), 3.71 (s, 3 H), 4.13 (q, 2 H), 4.57 (s, 2 H), 5.94 (s, 2 H), 6.78 (s, 1 H), 6.87 (m, 2 H), 7.19 (m, 1 H), 7.57 (s, 1 H), 7.60 (s, 1 H). |
| 116 | Ethyl 6-bromo-5-hydroxy-4-[(1-imidazolyl)methyl]-1-methyl-2-(phenylsulfinylmethyl)-1H-indole-3-carboxylate | 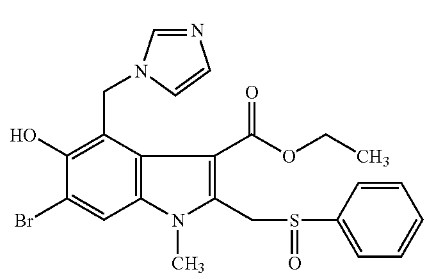 | (DMSO): 1.23 (t, 3 H), 2.50 (s, 3 H), 4.15 (q, 2 H), 4.79 (s, 2 H), 5.79 (s, 2 H), 6.74 (s, 1 H), 6.86 (s, 1 H), 7.30-7.57 (m, 5 H), 7.79 (s, 1 H). |

TABLE 5-continued

| Example No. | Chemical Name | Structure | $^1$H-NMR Data (300 Hz) d (ppm) |
|---|---|---|---|
| 117 | Ethyl 6-bromo-1-cyclopropyl-5-hydroxy-4-[(1-imidazoly)methyl]-2-[(4-fluorophenyl)sulfinyl-methyl]-1H-indole-3-carboxylate | 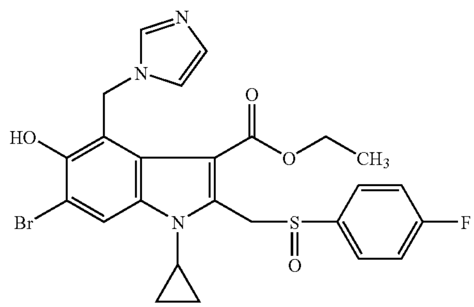 | (DMSO): 1.00 (m, 1 H), 1.00 (m, 1 H), 1.20 (m, 2 H), 1.36 (t, 3 H), 2.47 (m, 1 H), 3.32 (q, 2 H), 4.73 (d, 1 H), 4.94 (d, 1 H), 5.88 (d, 1 H), 5.94 (d, 1 H), 6.95 (s, 2 H), 7.12 (t, 2 H), 7.38~7.42 (m, 2 H), 7.55 (s, 1 h), 7.71 (s, 1 H). |
| 118 | Ethyl 6-bromo-5-hydroxy-4-[(1-imidazolyl)methyl]-1-methyl-2-[(3-methoxyphenyl)sulfinyl-methyl]-1H-indole-3-carboxylate | 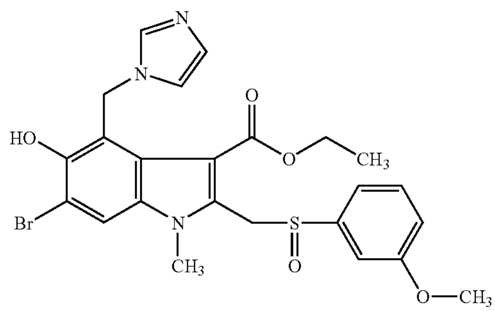 | (DMSO): 1.22 (t, 3 H), 3.51 (s, 3 H), 3.62 (s, 3 H), 4.13 (q, 2 H), 4.81 (s, 2 H), 5.78 (s, 2 H), 6.76 (s, 1 H), 6.85 (s, 1 H), 6.92 (s, 1 H), 7.01 (d, 1 H), 7.10 (d, 1 H), 7.42 (m, 2 H), 7.87 (s, 1 H). |
| 119 | Ethyl 6-bromo-1-cyclopropyl-5-hydroxy-4-[(1-imidazolyl)methyl]-2-[(3,4-difluorophenyl)sulfinyl-methyl]-1H-indole-3-carboxylate | 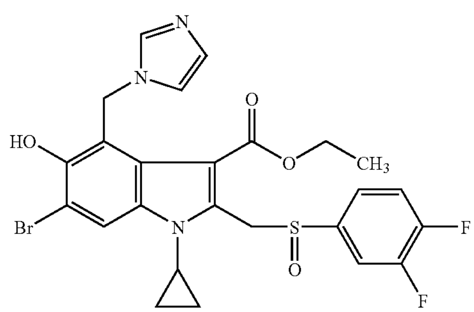 | (DMSO): 0.95 (m, 1 H), 1.04 (m, 1 H), 1.16 (m, 2 H), 1.23 (t, 3 H), 2.77 (m, 1 H), 4.15 (q, 2 H), 4.83 (s, 2 H), 5.74 (s, 2 H), 6.69 (s, 1 H), 6.87 (s, 1 H), 7.26 (m, 1 H), 7.39 (s, 1 H), 7.54~7.69 (m, 2 H), 7.72 (s, 1 H). |
| 120 | Ethyl 6-bromo-1-cyclopropyl-5-hydroxy-4-[(1-imidazolyl)methyl]-2-[(2-pyridyl)sulfinylmeth-yl]-1H-indole-3-carboxylate | 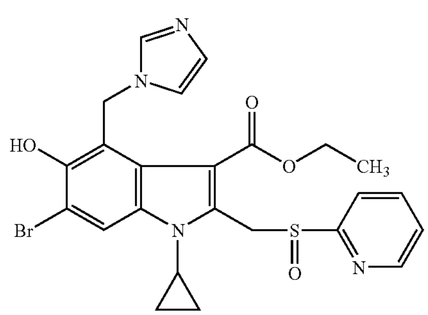 | (CDCl$_3$): 0.97 (m, 1 H), 1.13 (m, 1 H) 1.28 (m, 2 H), 1.36 (t, 3 H), 3.06 (m, 1 H), 4.29 (q, 2 H), 4.90 (d, 1 H), k5.16 (d, 1 H), 5.89 (dd, 2 H), 6.92 (s, 1 H), 6.96 (s, 1 H), 7.42 (m, 1 H), 7.53 (s, 1 H), 7.79 (m, 2 H), 7.88 (t, 1 H), 8.60 (d, 1 H). |
| 121 | Ethyl 6-bromo-5-hydroxy-4-[(1-imidazolyl)methyl]-1-methyl-2-[(3,4-difluorophenyl)sulfinyl-methyl]-1H-indole-3-carboxylate | 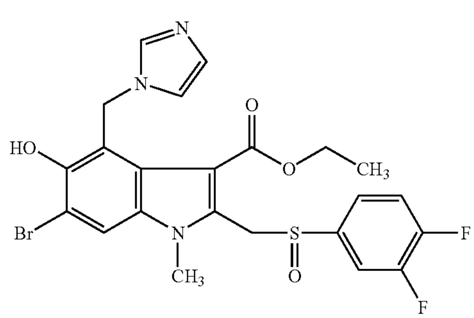 | (DMSO): 1.19 (t, 3 H), 3.58 (s, 3 H), 4.08 (q, 2 H), 4.82 (d, 1 H), 4.87 (d, 1 H), 5.72 (s, 2 H), 6.70 (s, 1 H), 6.84 (s, 1 H), 7.24 (s, 1 H), 7.38 (s, 1 H), 7.53~7.64 (m, 2 H), 7.72 (s, 1 H). |

TABLE 5-continued

| Example No. | Chemical Name | Structure | $^1$H-NMR Data (300 Hz) d (ppm) |
| --- | --- | --- | --- |
| 122 | Ethyl 6-bromo-5-hydroxy-4-[(1-imidazolyl)methyl]-1-methyl-2-[(4-fluorophenyl)sulfinyl-methyl]-1H-indole-3-carboxylate | 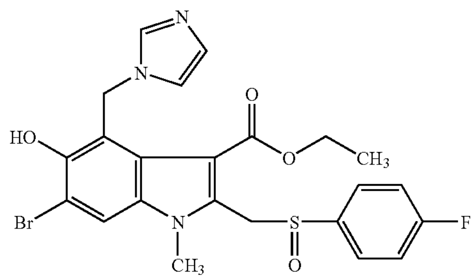 | (DMSO): 1.20 (t, 3 H), 3.58 (s, 3 H), 4.11 (q, 2 H), 4.83 (s, 2 H), 5.75 (s, 2 H), 6.75 (s, 1 H), 6.81 (s, 1 H), 7.33~7.39 (m, 3 H), 7.46~7.51 (dd, 2 H), 7.88 (s, 1 H). |
| 123 | Ethyl 6-bromo-5-hydroxy-4-[(1-imidazolyl)methyl]-1-methyl-2-[(2,4-dimethylphenyl)-sulfinylmethyl]-1H-indole-3-carboxylate | 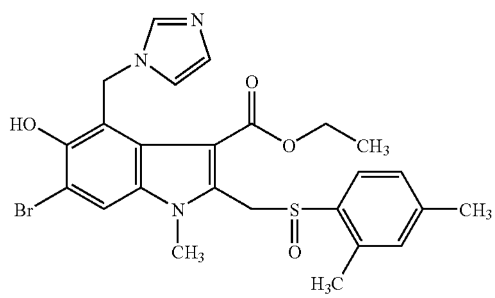 | (DMSO): 1.19 (t, 3 H), 1.99 (s, 3 H), 2.39 (s, 3 H), 3.39 (s, 3 H), 4.09 (q, 2 H), 4.74 (s, 2 H), 5.71 (s, 2 H), 6.71 (s, 1 H), 6.85 (s, 1 H), 7.04 (s, 1 H), 7.22 (d, 1 H), 7.37 (s, 1 H), 7.51 (d, 1 H), 7.69 (s, 1 H). |
| 124 | Ethyl 6-bromo-5-hydroxy-4-[(1-imidazolyl)methyl]-1-methyl-2-[(4-nitrophenyl)sulfinyl-methyl]-1H-indole-3-carboxylate | 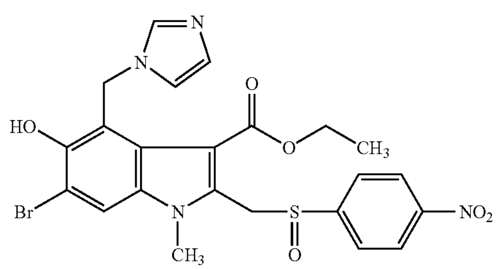 | (DMSO): 1.17 (t, 3 H), 3.62 (s, 3 H), 4.07 (q, 2 H), 4.90 (d, 1 H), 4.99 (d, 1 H), 5.68 (s, 2 H), 6.72 (s, 1 H), 6.79 (s, 1 H), 7.36 (s, 1 H), 7.71 (d, 2 H), 7.83 (s, 1 H), 8.34 (d, 2 H). |
| 125 | Ethyl 6-bromo-5-hydroxy-4-[(1-imidazolyl)methyl]-1-methyl-2-[(2-fluorophenyl)sulfinyl-methyl]-1H-indole-3-carboxylate | 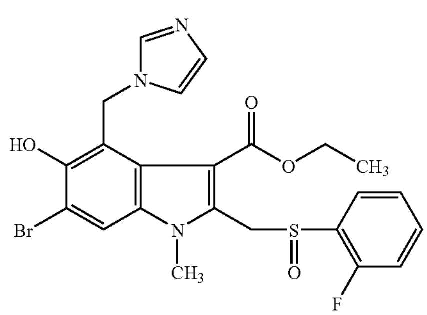 | (DMSO): 1.16 (t, 3 H), 3.74 (s, 3 H), 4.05 (q, 2 H), 4.94 (d, 1 H), 5.09 (d, 1 H), 5.86 (s, 2 H), 7.32~7.44 (m, 2 H), 7.52 (m, 1 H), 7.65 (m, 2 H), 6.04 (s, 1 H), 8.79 (s, 1 H), 9.36 (s, 1 H), 14.55 (br s, 1 H). |
| 126 | Ethyl 6-bromo-1-cyclopropyl-5-hydroxy-4-[(1-imidazolyl)methyl]-2-(benzylsulfinylmethyl)-1H-indole-3-carboxylate | 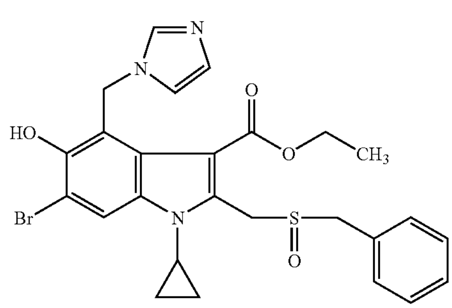 | (DMSO): 0.82 (m, 1 H), 1.03 (m, 3 H), 1.17 (t, 3 H), 3.05 (m, 1 H), 4.10 (q, 2 H), 4.16 (d, 1 H), 4.34 (d, 1 H), 4.58 (dd, 2 H), 5.74 (s, 2 H), 6.67 (s, 1 H), 6.92 (s, 1 H), 7.41 (m, 6 H), 7.67 (s, 1 H). |

TABLE 5-continued

| Example No. | Chemical Name | Structure | ¹H-NMR Data (300 Hz) d (ppm) |
|---|---|---|---|
| 127 | Ethyl 6-bromo-1-cyclopropyl-5-hydroxy-4-[(1-imidazolyl)methyl]-2-[(2-fluorobenzyl)sulfinylmethyl]-1H-indole-3-carboxylate | 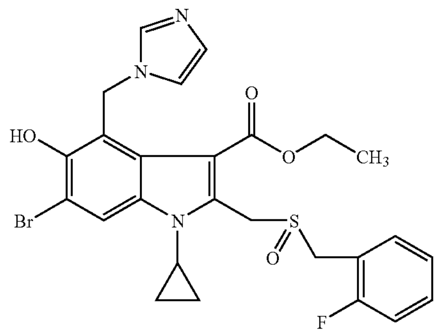 | (CDCl$_3$): 0.84 (m, 1 H), 1.14 (m, 3 H), 1.24 (t, 3 H), 3.20 (m, 1 H), 4.12~4.26 (m, 4 H), 4.62 (dd, 2 H), 5.87 (dd, 2 H), 6.92 (d, 2 H), 7.16 (m, 1 H), 7.21 (d, 1 H), 7.40 (m, 2 H), 7.53 (s, 1 H), 7.77 (s, 1 H). |
| 128 | Ethyl 6-bromo-1-cyclopropyl-5-hydroxy-4-[(1-imidazolyl)methyl]-2-[(4-thiazolylmethyl)-sulfinylmethyl]-1H-indole-3-carboxylate dihydrochloride | 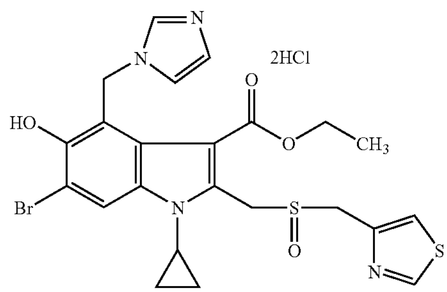 | (CDCl$_3$): 0.90 (m, 1 H), 1.17 (m, 3 H), 1.28 (t, 3 H), 3.24 (m, 1 H), 4.28 (q, 2 H), 4.36 (dd, 2 H), 4.62 (d, 1 H), 4.86 (d, 1 H), 5.87 (dd, 2 H), 6.64 (d, 2 H), 7.44 (s, 1 H), 7.53 (s, 1 H), 7.77 (s, 1 H), 8.84 (s, 1 H). |
| 129 | Ethyl 6-bromo-5-hydroxy-4-[(1-imidazolyl)methyl]-1-methyl-2-[(2-furylmethyl)sulfinylmethyl]-1H-indole-3-carboxylate | 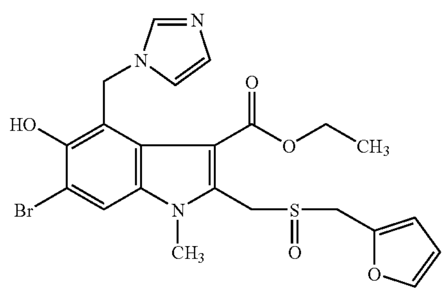 | (CDCl$_3$): 1.14 (t, 3 H), 3.79 (s, 3 H), 4.14 (q, 2 H), 4.36 (d, 1 H), 4.56 (d, 1 H), 4.72 (s, 2 H), 5.90 (s, 2 H), 6.53 (s, 2 H), 7.26 (s, 2 H), 7.75 (s, 1 H), 7.99 (s, 1 H), 8.30 (s, 2 H). |
| 130 | Ethyl 6-bromo-1-cyclopropyl-5-hydroxy-4-[(1-imidazolyl)methyl]-2-[(2-furylmethyl)sulfinylmethyl]-1H-indole-3-carboxylate | 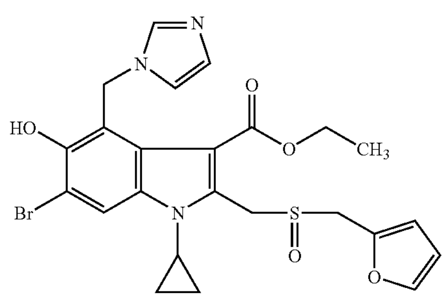 | (CDCl$_3$): 0.91 (m, 1 H), 1.21~1.29 (m, 5 H), 3.26 (m, 1 H), 4.16~4.31 (m, 4 H), 4.64 (d, 1 H), 4.75 (d, 1 H), 5.85 (d, 1 H), 5.94 (d, 1 H), 6.46 (t, 1 H), 6.50 (d, 1 H), 6.94 (s, 1 H), 6.97 (s, 1 H), 7.50 (d, 1 H), 7.57 (s, 1 H), 7.81 (s, 1 H). |
| 131 | Ethyl 6-bromo-5-hydroxy-1-methyl-4-[(2-methyl-1-imidazolyl)methyl]-2-(phenylsulfinylmethyl)-1H-indole-3-carboxylate | 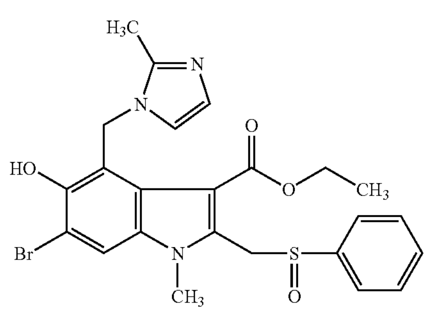 | (DMSO): 1.14 (t, 3 H), 2.33 (s, 3 H), 3.53 (s, 3 H), 4.05 (q, 2 H), 4.80 (s, 2 H), 5.56 (s, 2 H), 6.29 (s, 1 H), 6.53 (s, 1 H), 7.44-7.64 (m, 5 H), 7.87 (s, 1 H), 9.13 (br s, 1 H). |

TABLE 5-continued

| Example No. | Chemical Name | Structure | $^1$H-NMR Data (300 Hz) d (ppm) |
|---|---|---|---|
| 132 | Ethyl 6-bromo-1-cyclopropyl-5-hydroxy-4-[(2-methyl-1-imidazolyl)methyl]-2-[(2-fluorophenyl)sulfinyl-methyl]-1H-indole-3-carboxylate | 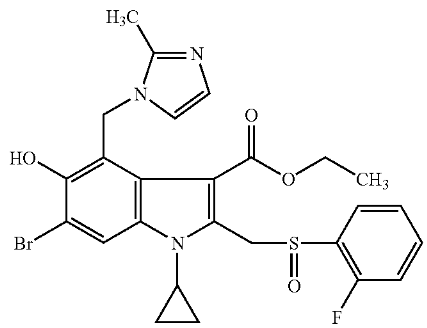 | (CDCl$_3$): 1.06 (m, 1 H), 1.16 (m, 1 H), 1.26 (t, 3 H), 1.30 (m, 2 H), 2.48 (s, 3 H), 3.09 (m, 1 H), 4.18 (q, 2 H), 4.98 (d, 1 H), 5.07 (d, 1 H), 5.65 (d, 2 H), 6.48 (d, 1 H), 6.58 (s, 1 H), 7.11 (t, 1 H), 7.36 (t, 1 H), 7.54 (m, 1 H), 7.72 (m, 1 H), 7.82 (s, 1 H). |
| 133 | Ethyl 6-bromo-5-hydroxy-1-methyl-4-[(2-methyl-1-imidazolyl)methyl]-2-[(3,4-difluorophenyl)sulfinyl-methyl]-1H-indole-3-carboxylate hydrochloride | 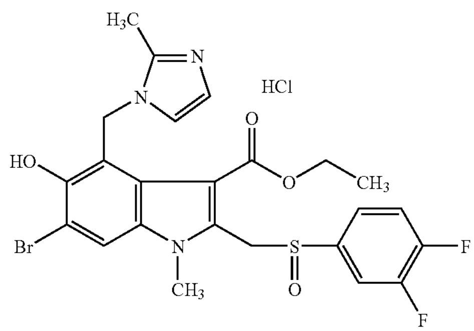 | (DMSO): 1.09 (t, 3 H), 2.32 (s, 3 H), 3.79 (s, 3 H), 3.98 (q, 2 H), 4.86 (d, 1 H), 4.92 (d, 1 H), 5.49 (s, 2 H), 6.24 (s, 1 H), 6.52 (s, 1 H), 7.26 (s, 1 H), 7.50~7.61 (m, 2 H), 7.90 (s, 1 H). |
| 134 | Ethyl 6-bromo-5-hydroxy-1-methyl-4-[(2-methyl-1-imidazolyl)methyl]-2-[(3-methylphenyl)sulfinyl-methyl]-1H-indole-3-carboxylate | 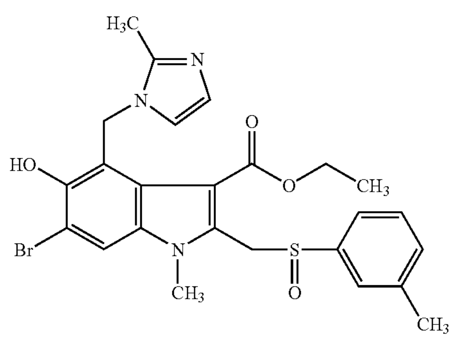 | (DMSO): 1.15 (t, 2 H), 2.25 (s, 3 H), 2.33 (s, 3 H), 3.49 (s, 3 H), 4.05 (q, 2 H), 4.72 (d, 1 H), 4.79 (d, 1 H), 5.56 (s, 2 H), 6.31 (s, 1 H), 6.51 (s, 1 H), 7.21~7.25 (m, 2 H), 7.37~7.39 (m, 2 H), 7.80 (s, 1 H). |
| 135 | Ethyl 6-bromo-5-hydroxy-1-methyl-4-[(2-methyl-1-imidazolyl)methyl]-2-[(2-methoxyphenyl)sulfinyl-methyl]-1H-indole-3-carboxylate hydrochloride | 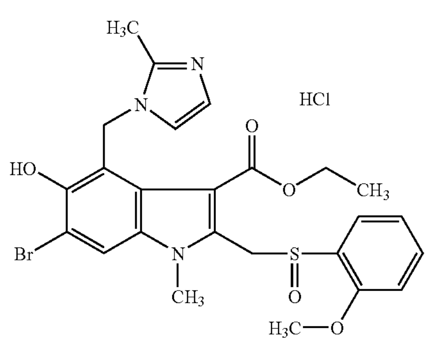 | (DMSO): 1.17 (t, 3 H), 2.68 (s, 3 H), 3.67 (s, 3 H), 3.69 (s, 3 H), 4.02 (q, 2 H), 4.81 (d, 1 H), 4.98 (d, 1 H), 5.69 (s, 2 H), 6.82 (d, 1 H), 7.09~7.15 (m, 2 H), 7.39 (dd, 1 H), 7.45 (d, 1 H), 7.52 (m, 1 H), 9.25 (s, 1 H), 14.17 (br s, 1 H). |

TABLE 5-continued

| Example No. | Chemical Name | Structure | $^1$H-NMR Data (300 Hz) d (ppm) |
|---|---|---|---|
| 136 | Ethyl 6-bromo-5-hydroxy-1-methyl-4-[(2-methyl-1-imidazolyl)methyl]-2-[(3-chloro-4-fluorophenyl)sulfinylmethyl]-1H-indole-3-carboxylate | 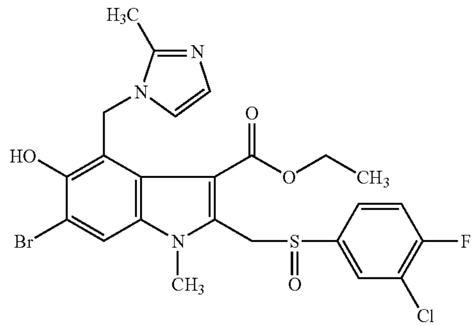 | (CDCl$_3$): 1.21 (t, 3 H), 2.55 (s, 3 H), 3.69 (s, 3 H), 4.19 (q, 2 H), 4.62 (d, 1 H), 4.75 (d, 1 H), 5.66 (s, 2 H), 6.52 (s, 1 H), 6.71 (s, 1 H), 7.28 (m, 1 H), 7.37 (s, 1 H), 7.58 (s, 1 H), 7.63 (d, 1 H). |
| 137 | Ethyl 6-bromo-1-cyclopropyl-5-hydroxy-4-[(2-methyl-1-imidazolyl)methyl]-2-[(2,6-dichlorophenyl)-sulfinylmethyl]-1H-indole-3-carboxylate | 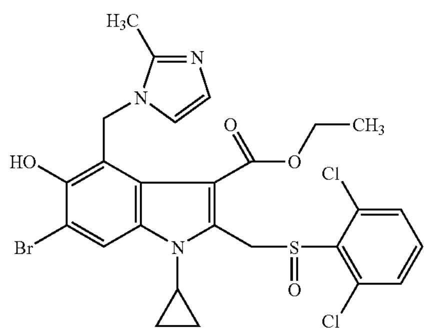 | (CDCl$_3$): 1.09 (m, 1 H), 1.16 (m, 1 H), 1.22 (t, 3 H), 1.39 (m, 2 H), 2.43 (s, 3 H), 3.13 (m, 1 H), 4.13 (q, 2 H), 5.21 (d, 1 H), 5.56 (s, 2 H), 5.62 (d, 1 H), 6.40 (d, 1 H), 6.59 (d, 1 H), 7.30~7.35 (m, 3 H), 7.80 (s, 1 H). |
| 138 | Ethyl 6-bromo-1-cyclopropyl-5-hydroxy-4-[(2-methyl-1-imidazolyl)methyl]-2-[(4-fluorophenyl)sulfinylmethyl]-1H-indole-3-carboxylate | 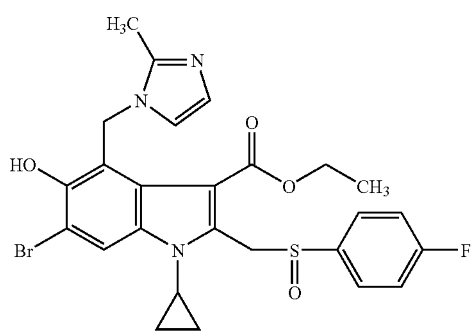 | (DMSO): 0.99 (m, 2 H), 1.20 (m, 2 H), 1.34 (t, 3 H), 2.30 (s, 3 H), 2.82 (m, 1 H), 4.22 (q, 2 H), 4.91 (s, 2 H), 5.54 (s, 2 H), 7.38-7.43 (m, 3 H), 7.54-7.60 (m, 3 H), 7.71 (s, 1 H), 9.98 (br s, 1 H). |
| 139 | Ethyl 6-bromo-5-hydroxy-1-methyl-4-[(2-methyl-1-imidazolyl)methyl]-2-[(phenoxyethyl)sulfinylmethyl]-1H-indole-3-carboxylate | 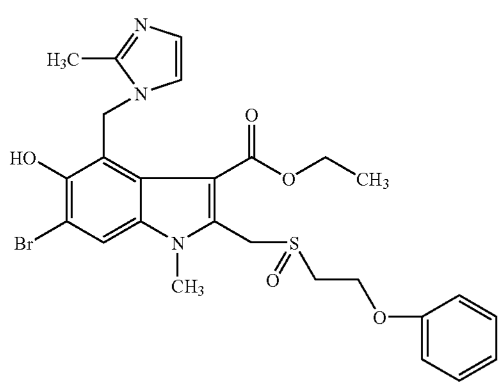 | (DMSO): 1.13 (t, 3 H), 2.33 (s, 3 H), 3.31 (m, 2 H), 3.82 (s, 3 H), 4.11 (q, 2 H), 4.34 (m, 2 H), 4.45 (m, 2 H), 4.76 (dd, 2 H), 5.61 (dd, 2 H), 6.38 (s, 1 H), 6.58 (s, 1 H), 6.98 (m, 3 H), 7.31 (t, 2 H), 7.95 (s, 1 H). |

TABLE 5-continued

| Example No. | Chemical Name | Structure | $^1$H-NMR Data (300 Hz) d (ppm) |
|---|---|---|---|
| 140 | Ethyl 6-bromo-1-cyclopropyl-5-hydroxy-4-[(2-methyl-1-imidazolyl)methyl]-2-[(2-furylmethyl)sulfinylmethyl]-1H-indole-3-carboxylate | 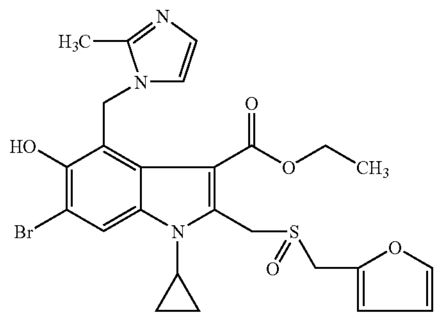 | (CDCl$_3$): 0.92 (m, 1 H), 1.15~1.24 (m, 6 H), 2.44 (s, 3 H), 3.26 (m, 1 H), 4.15~4.28 (m, 4 H), 4.62 (d, 1 H), 4.75 (d, 1 H), 5.61 (s, 2 H), 6.46 (m, 4 H), 7.48 (d, 1 H), 7.83 (s, 1 H). |
| 141 | Ethyl 6-bromo-1-cyclopropyl-5-hydroxy-4-[(2-methyl-1-imidazolyl)methyl]-2-[(2-methyl-3-furyl)sulfinylmethyl]-1H-indole-3-carboxylate | 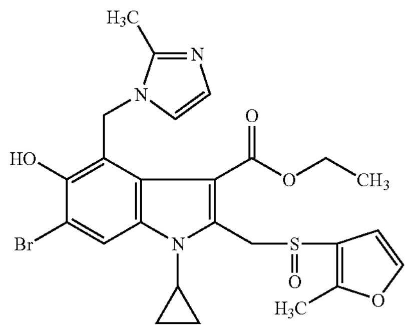 | (CDCl$_3$): 1.04 (m, 1 H), 1.21 (m, 1 H), 1.29 (t, 3 H), 1.34 (m, 2 H), 1.84 (s, 3 H), 2.44 (s, 3 H), 2.91 (m, 1 H), 4.24 (m, 2 H), 4.88 (d, 1 H), 5.04 (d, 1 H), 5.63 (dd, 2 H), 6.42 (s, 1 H), 6.48 (s, 1 H), 6.71 (d, 1 H), 7.39 (d, 1 H), 7.80 (s, 1 H). |
| 142 | Ethyl 5-hydroxy-1-methyl-4-[(2-methyl-1-imidazolyl)methyl]-2-[(4-methylphenyl)sulfinylmethyl]-1H-indole-3-carboxylate | 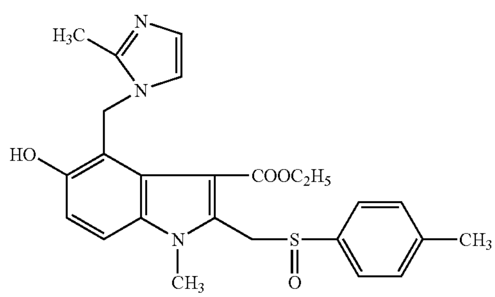 | (DMSO): 1.12 (t, 3 H), 2.32 (s, 3 H), 2.35 (s, 3 H), 3.53 (s, 3 H), 4.05 (q, 2 H), 4.71 (d, 1 H), 4.76 (d, 1 H), 5.47 (s, 2 H), 6.33 (s, 1 H), 6.49 (s, 1 H), 6.97 (d, 1 H), 7.29~7.38 (m, 5 H). |
| 143 | Ethyl 5-hydroxy-1-methyl-4-[(2-methyl-1-imidazolyl)methyl]-2-[(2-furylmethyl)sulfinylmethyl]-1H-indole-3-carboxylate | 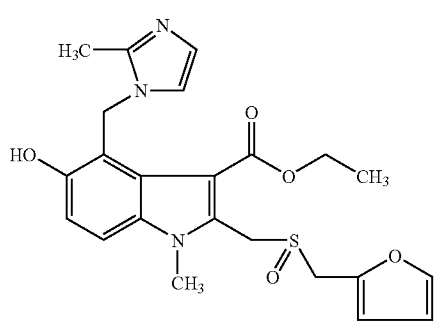 | (DMSO): 1.12 (t, 3 H), 2.64 (s, 3 H), 3.79 (s, 3 H), 4.08 (q, 2 H), 4.36 (d, 1 H), 4.54 (d, 1 H), 4.72 (s, 2 H), 5.65 (s, 2 H), 6.53 (s, 2 H), 6.82 (s, 1 H), 7.01 (d, 1 H), 7.25 (s, 1 H), 7.55 (d, 1 H), 7.75 (s, 1 H), 9.85 (s, 1 H). |
| 144 | Ethyl 6-bromo-5-hydroxy-1-methyl-4-[(1H-1,2,4-triazol-1-yl)methyl]-2-[(4-trifluorophenyl)sulfinylmethyl]-1H-indole-3-carboxylate | 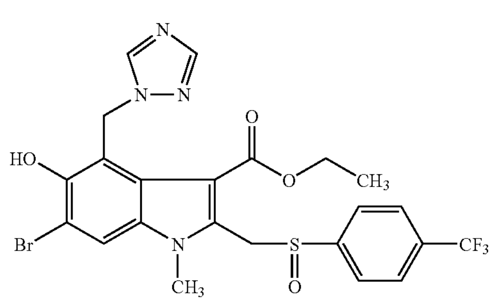 | (CDCl$_3$): 1.41 (t, 3 H), 3.53 (s, 3 H), 4.33 (q, 2 H), 4.71 (s, 2 H), 6.15 (s, 2 H), 7.58~7.63 (m, 4 H), 7.75 (s, 2 H), 8.07 (s, 1 H), 8.64 (br s, 1 H). |

TABLE 5-continued

| Example No. | Chemical Name | Structure | $^1$H-NMR Data (300 Hz) d (ppm) |
|---|---|---|---|
| 145 | Ethyl 6-bromo-5-hydroxy-1-methyl-4-[(1H-1,2,4-triazol-1-yl)methyl]-2-[(4-fluorophenyl)sulfinyl-methyl]-1H-indole-3-carboxylate | 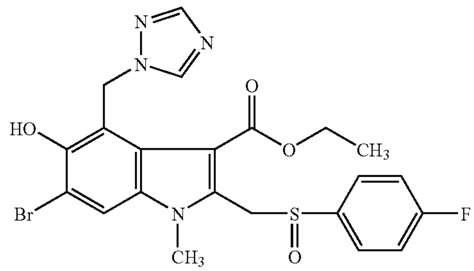 | (DMSO): 1.15 (t, 3 H), 3.52 (s, 3 H), 4.04 (q, 2 H), 4.81 (s, 2 H), 5.99 (dd, 2 H), 7.35 (m, 2 H), 7.48 (m, 2 H), 7.83 (s, 1 H), 7.89 (s, 1 H), 8.08 (s, 1 H), 9.17 (br s, 1 H). |
| 146 | Ethyl 6-bromo-5-hydroxy-1-methyl-4-[(1H-1,2,4-triazol-1-yl)methyl]-2-(phenylsulfinylmethyl)-1H-indole-3-carboxylate | 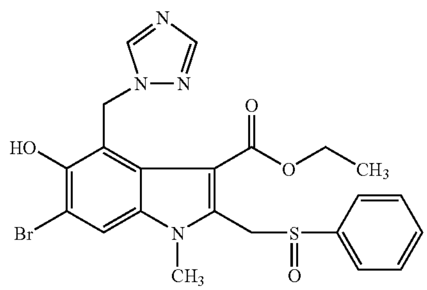 | (DMSO): 1.18 (t, 3 H), 3.49 (s, 3 H), 4.09 (q, 2 H), 4.77 (s, 2 H), 5.97 (dd, 2 H), 7.46~7.57 (m, 5 H), 7.81 (s, 2 H), 8.07 (s, 1 H). |
| 147 | Ethyl 6-bromo-5-hydroxy-1-methyl-4-[(1H-1,2,4-triazol-1-yl)methyl]-2-[(4-trifluoromethoxy-phenyl)sulfinylmethyl]-1H-indole-3-carboxylate | 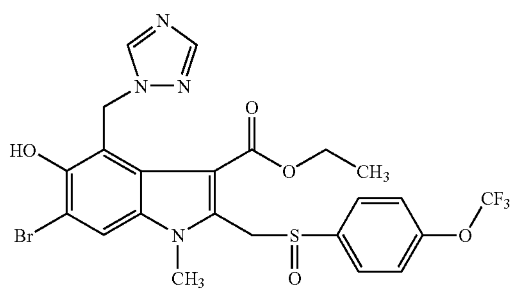 | (CDCl$_3$): 1.43 (t, 3 H), 3.43 (s, 3 H), 4.36 (q, 2 H), 4.60 (d, 1 H), 4.77 (d, 1 H), 6.09 (s, 2 H), 7.30 (d, 2 H), 7.47 (d, 2 H), 7.96 (s, 1 H), 8.53 (s, 1 H), 9.47 (brs, 1 H). |
| 148 | Ethyl 6-bromo-5-hydroxy-1-methyl-4-[(1H-1,2,4-triazol-1-yl)methyl]-2-[(3-methylphenyl)sulfinyl-methyl]-1H-indole-3-carboxylate | 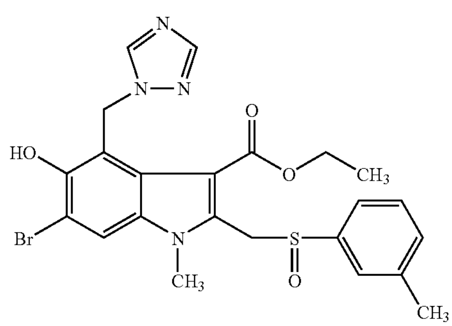 | (DMSO): 1.11 (t, 3 H), 2.28 (s, 3 H), 3.33 (s, 3 H), 3.99 (q, 2 H), 4.58 (d, 1 H), 4.68 (d, 1 H), 5.75 (d, 2 H), 7.21 (s, 1 H,) 7.26 (d, 2 H), 7.38 (m, 2 H), 7.44 (s, 1 H), 7.76 (s, 1 H), 7.83 (s, 1 H). |
| 149 | Ethyl 6-bromo-5-hydroxy-1-methyl-4-[(1H-1,2,4-triazol-1-yl)methyl]-2-[(4-fluorobenzyl)sulfinyl-methyl]-1H-indole-3-carboxylate | 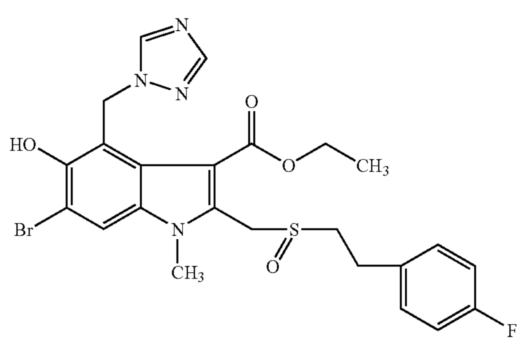 | (DMSO): 1.08 (t, 3 H), 3.72 (s, 3 H), 4.06 (q, 2 H), 4.18 (d, 1 H), 4.38 (d, 1 H), 4.55 (d, 1 H), 4.64 (d, 1 H), 5.94 (d, 1 H), 6.01 (d, 1 H), 7.24 (t, 2 H), 7.41 (dd, 2 H), 7.80 (s, 1 H), 7.85 (s, 1 H), 8.12 (s, 1 H). |

TABLE 5-continued

| Example No. | Chemical Name | Structure | $^1$H-NMR Data (300 Hz) d (ppm) |
|---|---|---|---|
| 150 | Ethyl 6-bromo-1-cyclopropyl-5-hydroxy-4-[(1H-1,2,4-triazol-1-yl)methyl]-2-[2-furylmethyl)sulfinyl-methyl]-1H-indole-3-carboxylate | 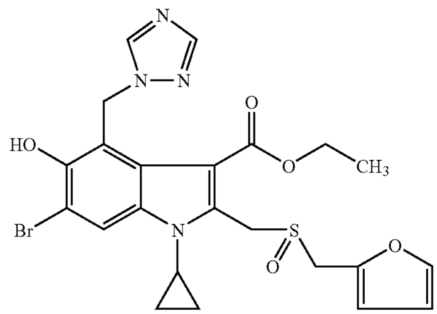 | (CDCl$_3$): 0.91 (m, 1 H), 1.25 (m, 3 H), 1.34 (t, 3 H), 3.27 (m, 1 H), 4.22 (dd, 2 H), 4.33 (dd, 2 H), 4.73 (dd, 2 H), 6.03 (d, 1 H), 6.17 (d, 1 H), 6.47 (t, 1 H), 6.51 (d, 1 H), 7.50 (d, 1 H), 7.88 (s, 1 H), 7.96 (s, 1 H), 8.57 (s, 1 H), 9.39 (brs, 1 H). |
| 151 | Ethyl 6-bromo-4-(guanidinylmethyl)-5-hydroxy-1-methyl-2-[(2-methoxyphenyl)-sulfinyl-methyl]-1H-indole-3-carboxylate hydrochloride | 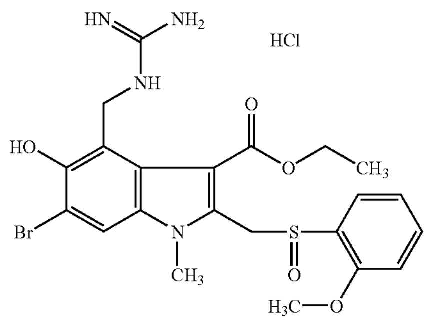 | (DMSO): 1.29 (t, 3 H), 3.61 (s, 3 H), 3.73 (s, 3 H), 4.41 (q, 2 H), 4.70 (d, 1 H), 4.75 (s, 2 H), 4.94 (d, 1 H), 6.65 (br s, 1 H), 7.12~7.19 (m, 2 H), 7.25 (s, 1 H), 7.46 (d, 1 H), 7.55 (m, 1 H), 7.89 (s, 1 H), 9.18 (brs, 1 H). |
| 152 | Ethyl 6-bromo-4-(guanidinylmethyl)-5-hydroxy-1-methyl-2-[(4-methylphenyl)sulfinyl-methyl]-1H-indole-3-carboxylate hydrochloride | 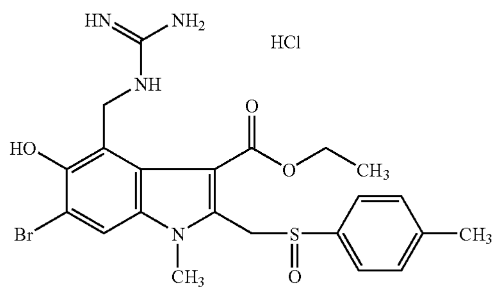 | (DMSO): 1.31 (t, 3 H), 2.39 (s, 3 H), 3.54 (s, 3 H), 4.23 (q, 2 H), 4.76 (s, 4 H), 6.74 (br s, 1 H), 7.31 (s, 1 H), 7.38 (d, 2 H), 7.43 (d, 2 H), 7.90 (s, 1 H), 9.22 (s, 1 H). |
| 153 | Ethyl 6-bromo-4-(guanidinylmethyl)-5-hydroxy-1-methyl-2-[(4-fluorophenyl)sulfinyl-methyl]-1H-indole-3-carboxylate | 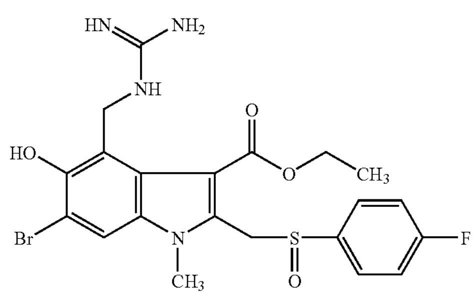 | (DMSO): 1.36 (t, 3 H), 3.62 (s, 3 H), 4.26 (q, 2 H), 4.59 (s, 2 H), 4.67 (d, 1 H), 4.78 (d, 1 H), 6.68 (br s, 2 H), 6.92 (s, 1 H), 7.01 (m, 2 H), 7.10 (d, 2 H), 7.43 (d, 1 H), 7.47 (s, 1 H). |
| 154 | Ethyl 6-bromo-1-cyclopropyl-4-(guanidinylmethyl)-5-hydroxy-2-[(4-fluorophenyl)sulfinyl-methyl]-1H-indole-3-carboxylate | 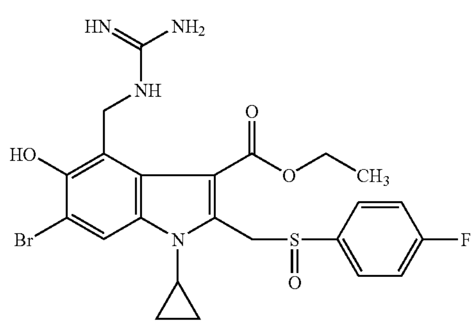 | (DMSO): 0.78 (m, 1 H), 0.96 (m, 1 H), 1.10 (m, 2 H), 1.37 (t, 3 H), 2.29 (m, 1 H), 4.31 (q, 2 H), 4.56 (s, 2 H), 4.70 (d, 1 H), 4.85 (d, 1 H), 6.99 (s, 1 H), 7.16 (s, 2 H), 7.41 (m, 3 H), 7.49-7.54 (m, 3 H), 12.5 (br s, 1 H). |

TABLE 5-continued

| Example No. | Chemical Name | Structure | $^1$H-NMR Data (300 Hz) d (ppm) |
|---|---|---|---|
| 155 | Ethyl 6-bromo-4-(guanidinylmethyl)-5-hydroxy-1-methyl-2-[(1-adamantanyl)sulfinyl-methyl]-1H-indole-3-carboxylate | 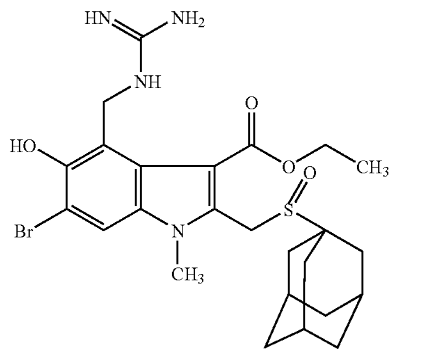 | (DMSO): 1.32 (t, 3 H), 1.76 (m, 6 H), 1.98 (m, 6 H), 2.18 (m, 3 H), 3.63 (s, 3 H), 4.28 (q, 2 H), 4.43 (d, 2 H), 4.61 (dd, 2 H), 6.65 (s, 2 H), 6.98 (brs, 1 H), 7.55 (s, 1 H). |
| 156 | Ethyl 6-bromo-1-cyclopropyl-4-[(2-aminoethylthio)meth-yl]-5-hydroxy-2-[(4-fluorophenyl)sulfinyl-methyl]-1H-indole-3-carboxylate | 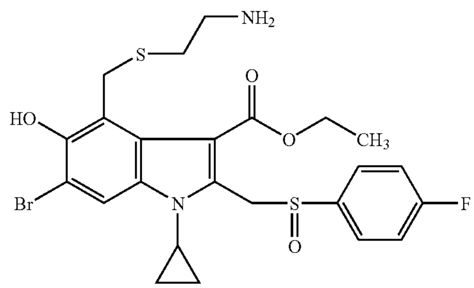 | (DMSO): 0.97 (m, 1 H), 1.05 (m, 1 H), 1.23 (m, 2 H), 1.32 (t, 3 H), 2.72 (m, 1 H), 2.99 (t, 2 H), 3.10 (t, 2 H), 4.20 (q, 2 H), 4.44 (s, 2 H), 4.76 (d, 1 H), 4.82 (d, 1 H), 7.40 (m, 2 H), 7.54 (m, 2 H), 7.70 (s, 1 H). |
| 157 | Ethyl 6-bromo-4-[(2-aminoethylthio)meth-yl]-5-hydroxy-1-methyl-2-[(4-fluorophenyl)sulfinyl-methyl]-1H-indole-3-carboxylate | 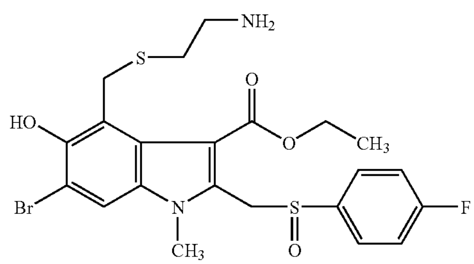 | (DMSO): 1.29 (t, 3 H), 2.45 (s, 3 H), 2.98 (t, 2 H), 3.11 (t, 2 H), 4.14 (q, 2 H), 4.44 (s, 2 H), 4.80 (d, 2 H), 7.29 (m, 2 H), 7.52 (m, 2 H), 8.18 (br s, 1 H). |
| 158 | Ethyl 6-bromo-4-[(2-aminoethylthio)meth-yl]-5-hydroxy-1-methyl-2-[(2-pyridylphenyl)sulfinyl-methyl]-1H-indole-3-carboxylate | 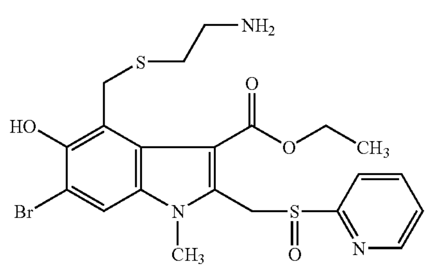 | (DMSO): 1.33 (t, 3 H), 2.45 (s, 3 H), 2.99 (t, 2 H), 3.10 (t, 2 H), 4.17 (q, 2 H), 4.46 (s, 2 H), 4.77 (d, 1 H), 5.03 (d, 1 H), 7.61 (m, 1 H), 7.76 (m, 2 H), 8.18 (m, 1 H), 8.69 (s, 1 H). |
| 159 | Ethyl 6-bromo-5-hydroxy-4-[(1-imidazolyl)methyl]-1-methyl-2-(phenylsulfonylmeth-yl)-1H-indole-3-carboxylate | 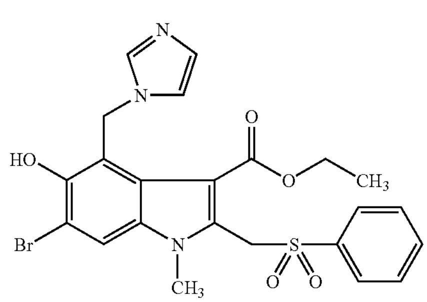 | (DMSO): 1.16 (t, 3 H), 3.55 (s, 3 H), 3.98 (q, 2 H), 5.26 (s, 2 H), 5.70 (s, 2 H), 6.68 (s, 1 H), 7.35 (s, 1 H), 7.56-7.67 (m, 5 H), 7.76 (s, 1 H). |

TABLE 5-continued

| Example No. | Chemical Name | Structure | $^1$H-NMR Data (300 Hz) d (ppm) |
|---|---|---|---|
| 160 | Ethyl 6-bromo-1-cyclopropyl-5-hydroxy-4-[(1-imidazolyl)methyl]-2-[(3,4-difluorophenyl)sulfonyl-methyl]-1H-indole-3-carboxylate | 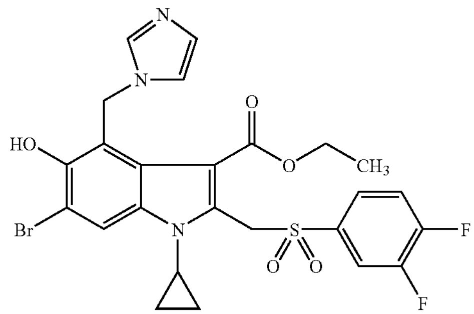 | (CDCl$_3$): 1.02 (m, 2 H), 1.22 (t, 3 H), 1.39 (m, 2 H), 3.40 (m, 1 H), 4.02 (q, 4 H), 5.27 (s, 2 H), 5.80 (s, 2 H), 6.87 (s, 1 H), 6.95 (s, 1 H), 7.29 (m, 2 H), 7.50 (m, 2 H), 7.87 (s, 1 H). |
| 161 | Ethyl 6-bromo-1-cyclopropyl-5-hydroxy-4-[(1-imidazolyl)methyl]-2-[(4-thiazolylmethyl)sulfonyl-methyl]-1H-indole-3-carboxylate | 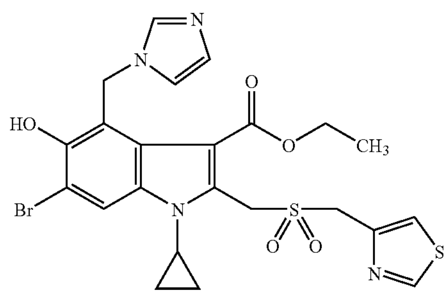 | (DMSO): 1.02 (m, 2 H), 1.17 (m, 5 H), 3.17 (m, 1 H), 4.13 (q, 2 H), 4.98 (s, 2 H), 5.29 (s, 2 H), 5.76 (s, 2 H), 6.75 (s, 1 H), 6.83 (s, 1 H), 7.36 (s, 1 H), 7.88 (s, 2 H), 9.24 (d, 1 H). |
| 162 | Ethyl 6-bromo-1-cyclopropyl-5-hydroxy-4-[(1-imidazolyl)methyl]-2-[(2-furylmethyl)sulfonyl-methyl]-1H-indole-3-carboxylate | 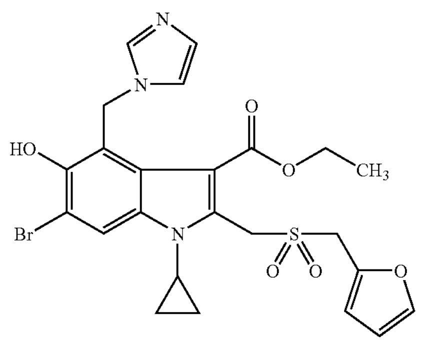 | (DMSO): 1.03 (m, 2 H), 1.18 (m, 5 H), 3.12 (m, 1 H), 4.14 (q, 2 H), 4.93 (s, 2 H), 5.17 (s, 2 H), 5.78 (s, 2 H), 6.57 (s, d, 1 H), 6.64 (d, 1 H), 7.01 (s, 1 H), 7.03 (s, 1 H), 7.36 (s, 1 H), 7.92 (s, 1 H), 8.39 (s, 1 H). |
| 163 | Ethyl 6-bromo-5-hydroxy-4-[(1-imidazolyl)methyl]-1-methyl-2-[(4-fluorobenzyl)sulfonyl-methyl]-1H-indole-3-carboxylate | 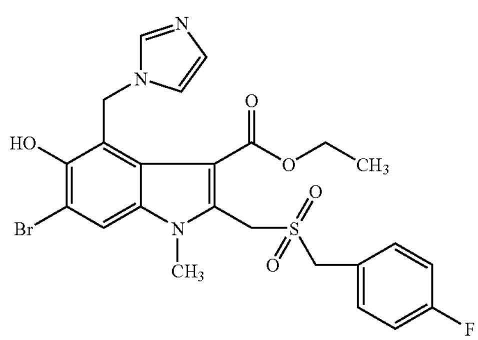 | (DMSO): 1.02 (t, 3 H), 3.78 (s, 3 H), 4.04 (q, 2 H), 4.72 (s, 2 H), 5.10 (s, 2 H), 5.76 (s, 2 H), 6.81 (s, 1 H), 6.87 (s, 1 H), 7.28 (t, 2 H), 7.50 (dd, 2 H), 7.54 (s, 1 H), 7.96 (s, 1 H), 9.18 (brs, 1 H). |
| 164 | Ethyl 5-hydroxy-4-[(1-imidazolyl)methyl]-1-methyl-2-[(4-methylphenyl)sulfonyl-methyl]-1H-indole-3-carboxylate | 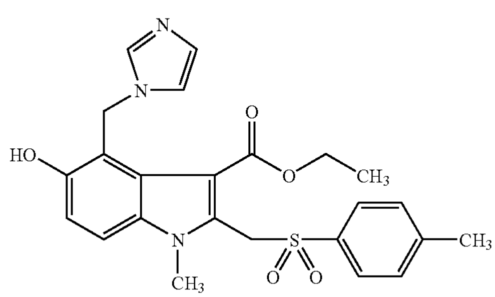 | (CDCl$_3$): 0.94 (m, 2 H), 1.19-1.27 (m, 5 H), 2.40 (s, 3 H), 3.16 (m, 1 H), 3.99 (q, 2 H), 5.27 (s, 2 H), 5.79 (s, 2 H), 6.92-7.06 (m, 3 H), 7.21 (d, 2 H), 7.43-7.46 (m, 3 H), 7.64 (s, 1 H). |

TABLE 5-continued

| Example No. | Chemical Name | Structure | $^1$H-NMR Data (300 Hz) d (ppm) |
|---|---|---|---|
| 165 | Ethyl 6-bromo-1-cyclopropyl-5-hydroxy-4-[(2-methyl-1-imidazolyl)methyl]-2-[(2-fluorobenzyl)sulfonylmethyl]-1H-indole-3-carboxylate | 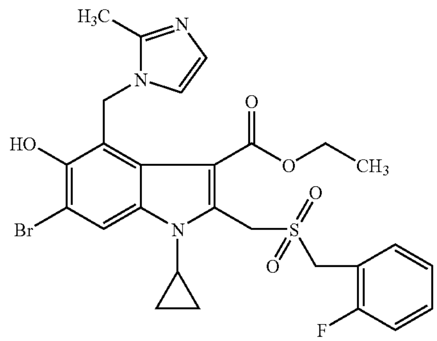 | (DMSO): 1.01~1.06 (m, 5 H), 1.15 (m, 2 H), 2.31 (s, 3 H), 3.21 (m, 1 H), 3.97 (q, 2 H), 4.79 (s, 2 H), 5.14 (s, 2 H), 5.53 (s, 2 H), 6.31 (s, 1 H), 6.53 (s, 1 H), 7.28 (d, 1 H), 7.33 (d, 1 H), 7.48 (m, 1 H), 7.59 (t, 1 H), 7.91 (s, 1 H), 9.22 (brs, 1 H). |
| 166 | Ethyl 6-bromo-5-hydroxy-1-methyl-4-[(2-methyl-1-imidazolyl)methyl]-2-(phenylsulfonylmethyl)-1H-indole-3-carboxylate | 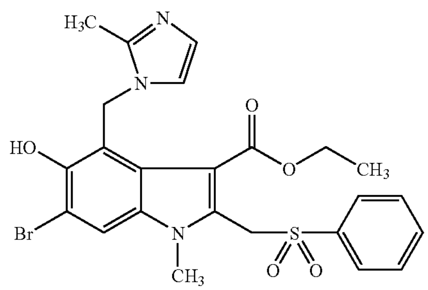 | (DMSO): 1.13 (t, 3 H), 2.65 (s, 3 H), 3.74 (s, 3 H), 3.96 (q, 2 H), 5.36 (s, 2 H), 5.65 (s, 2 H), 6.78 (d, 1 H), 7.41 (d, 1 H), 7.57~7.74 (m, 4 H), 7.78 (t, 1 H), 8.05 (s, 1 H), 6.32 (s, 1 H), 14.17 (brs, 1 H). |
| 167 | Ethyl 6-bromo-1-cyclopropyl-5-hydroxy-4-[(2-methyl-1-imidazolyl)methyl]-2-[(3-trifluoromethylphenyl)-sulfonylmethyl]-1H-indole-3-carboxylate | 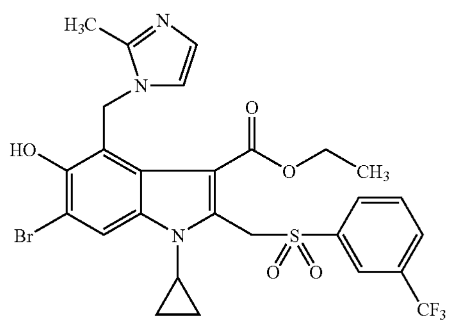 | (CDCl$_3$): 1.09 (m, 5 H), 1.40 (m, 2 H), 2.39 (s, 3 H), 3.40 (m, 1 H), 3.84 (q, 2 H), 5.32 (s, 2 H), 5.50 (s, 2 H), 6.33 (d, 1 H), 6.44 (d, 1 H), 7.58 (t, 1 H), 7.76 (d, 1 H), 7.88 (d, 1 H), 7.89 (s, 1 H), 7.93 (s, 1 H). |
| 168 | Ethyl 6-bromo-5-hydroxy-1-methyl-4-[(2-methyl-1-imidazolyl)methyl]-2-(benzylsulfonylmethyl)-1H-indole-3-carboxylate | 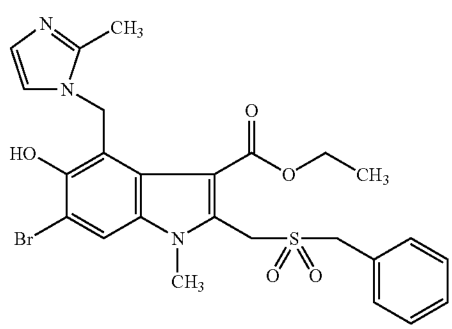 | (DMSO): 0.95 (t, 3 H), 2.67 (s, 3 H), 3.83 (s, 3 H), 3.95 (q, 2 H), 4.73 (s, 2 H), 5.16 (s, 2 H), 5.68 (s, 2 H), 6.88 (s, 1 H), 7.39 (s, 1 H), 7.40~7.47 (m, 6 H), 8.07 (s, 1 H), 9.32 (s, 1 H), 14.09 (br s, 1 H). |
| 169 | Ethyl 5-hydroxy-1-cyclopropyl-4-[(1H-1,2,4-triazol-1-yl)methyl]-2-[(4-fluorophenyl)sulfonylmethyl]-1H-indole-3-carboxylate | 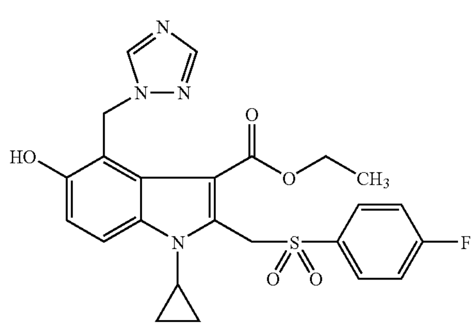 | (CDCl$_3$): 0.97 (m, 2 H), 1.34 (t, 3 H), 1.61 (m, 2 H), 3.15 (m, 1 H), 4.08 (q, 2 H), 5.30 (s, 2 H), 5.94 (s, 2 H), 7.06-7.15 (m, 3 H), 7.53-7.60 (m, 3 H), 7.97 (s, 1 H), 8.62 (s, 1 H), 9.54 (br s, 1 H). |

TABLE 5-continued

| Example No. | Chemical Name | Structure | $^1$H-NMR Data (300 Hz) d (ppm) |
|---|---|---|---|
| 170 | Ethyl 6-bromo-5-hydroxy-1-methyl-4-[(1H-1,2,4-triazol-1-yl)methyl]-2-[(4-trifluoromethylphenyl)-sulfonylmethyl]-1H-indole-3-carboxylate | 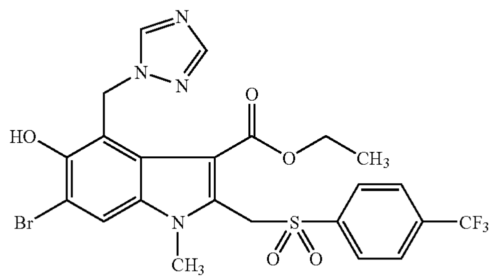 | (CDCl$_3$): 1.24 (t, 3 H), 3.82 (s, 3 H), 4.15 (q, 2 H), 5.14 (s, 2 H), 5.97 (s, 2 H), 7.67 (s, 1 H), 7.75 (s, 4 H), 7.96 (s, 1 H), 8.45 (s, 1 H), 9.08 (br s, 1 H). |
| 171 | Ethyl 6-bromo-5-hydroxy-1-methyl-4-[(1H-1,2,4-triazol-1-yl)methyl]-2-[(4-fluorobenzyl)sulfonyl-methyl]-1H-indole-3-carboxylate | 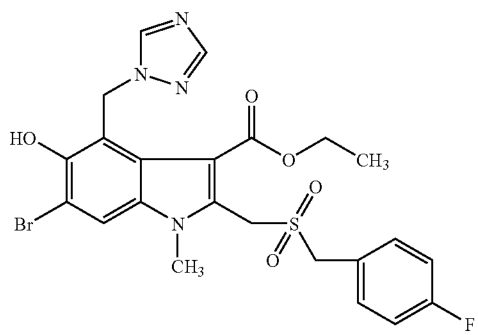 | (DMSO): 1.00 (t, 3 H), 3.78 (s, 3 H), 4.00 (q, 2 H), 4.70 (s, 2 H), 5.09 (s, 2 H), 5.95 (s, 2 H), 7.27 (t, 2 H), 7.50 (dd, 2 H), 7.79 (s, 1 H), 7.95 (s, 1 H), 8.14 (s, 1 H), 9.19 (brs, 1 H). |
| 172 | Ethyl 6-bromo-1-cyclopropyl-4-(guanidinylmethyl)-5-hydroxy-2-[(4-fluorophenyl)sulfonyl-methyl]-1H-indole-3-carboxylate | 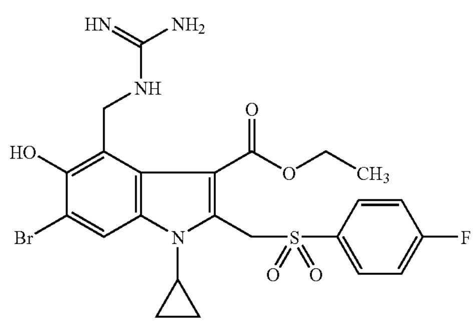 | (CDCl$_3$): 0.98 (m, 2 H), 1.30 (m, 5 H), 3.11 (m, 1 H), 4.16 (fq, 2 H), 4.84 (s, 2 H), 5.28 (brs, 1 H), 7.21 (m, 4 H), 7.49 (s, 1 H), 7.60 (d, 2 H), 7.78 (s, 1 H). |
| 173 | Ethyl 6-bromo-4-(guanidinylmethyl)-5-hydroxy-1-methyl-2-(benzylsulfonylmethyl)-1H-indole-3-carboxylate | 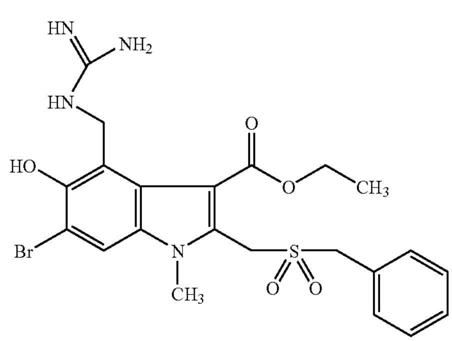 | (DMSO): 1.04 (t, 3 H), 3.67 (s, 3 H), 4.04 (q, 2 H), 4.51 (dd, 2 H), 4.84 (s, 2 H), 5.10 (s, 2 H), 6.62 (s, 2 H), 7.03 (s, 1 H), 7.41~7.48 (m, 6 H), 7.57 (s, 1 H). |

TABLE 5-continued

| Example No. | Chemical Name | Structure | ¹H-NMR Data (300 Hz) d (ppm) |
|---|---|---|---|
| 174 | Ethyl 1-cyclopropyl-4-(guanidinylmethyl)-5-hydroxy-2-[(4-methoxyphenyl)sulfonylmethyl]-1H-indole-3-carboxylate | 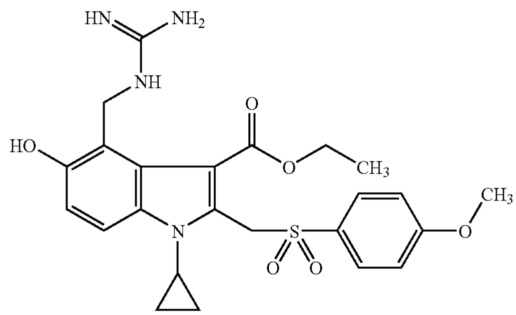 | (CDCl$_3$): 0.91 (m, 2 H), 1.22 (m, 2 H), 1.38 (t, 3 H), 2.84 (m, 1 H), 3.87 (s, 3 H), 4.14 (q, 2 H), 4.60 (s, 2 H), 5.22 (s, 2 H), 6.89 (m, 3 H), 7.41 (m, 3 H). |

TABLE 6

| Example No. | Chemical Name | Structure | MS m/z |
|---|---|---|---|
| 175 | Ethyl 6-bromo-5-hydroxy-4-[(1-imidazolyl)methyl]-1-methyl-2-[(3-fluorophenyl)thiomethyl]-1H-indole-3-carboxylate | 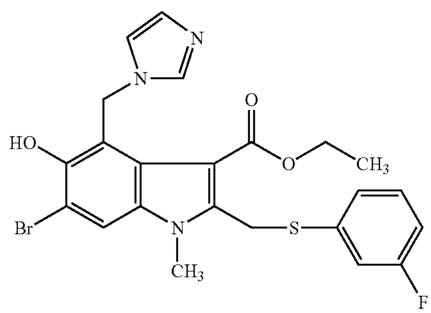 | 519.8, 517.7 [M + H] |
| 176 | Ethyl 6-bromo-5-hydroxy-4-[(1-imidazolyl)methyl]-1-methyl-2-(benzylthiomethyl)-1H-indole-3-carboxylate | 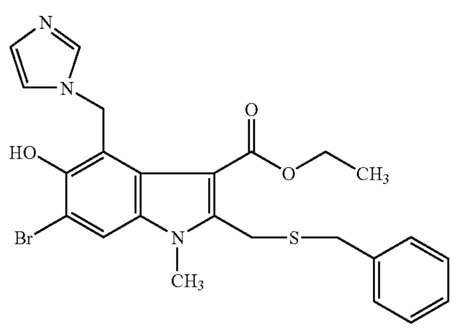 | 515.1, 513.1 [M + H] |
| 177 | Ethyl 6-bromo-5-hydroxy-4-[(1-imidazolyl)methyl]-1-methyl-2-[(4-trifluoromethylphenyl)sulfinylmethyl]-1H-indole-3-carboxylate | 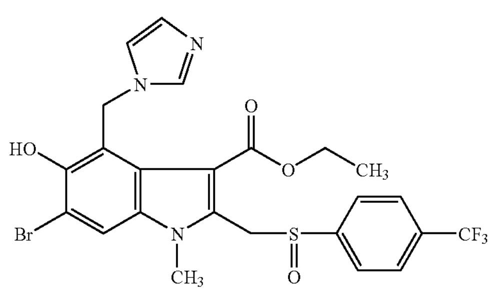 | 586.0, 583.9 [M + H] |

TABLE 6-continued

| Example No. | Chemical Name | Structure | MS m/z |
|---|---|---|---|
| 178 | Ethyl 6-bromo-1-cyclopropyl-5-hydroxy-4-[(2-methyl-1-imidazolyl)methyl]-2-(benzylsulfonylmethyl)-1H-indole-3-carboxylate | 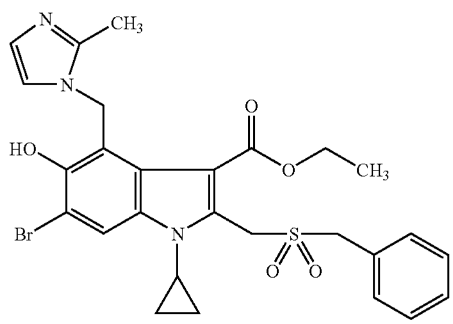 | 588.0, 586.2 [M + H] |
| 179 | Ethyl 6-bromo-5-hydroxy-1-methyl-4-[(2-methyl-1-imidazolyl)methyl]-2-[(1-adamantanyl)sulfonylmethyl]-1H-indole-3-carboxylate | 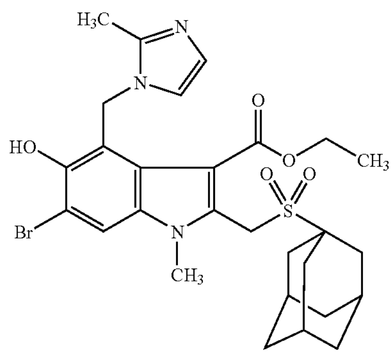 | 606.3, 604.2 [M + H] |
| 180 | Ethyl 6-bromo-5-hydroxy-1-methyl-4-[(2-methyl-1-imidazolyl)methyl]-2-[(4-trifluoromethylphenyl)sulfonylmethyl]-1H-indole-3-carboxylate | 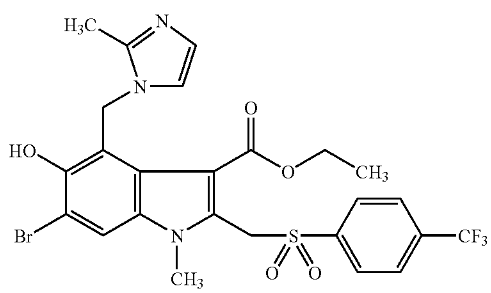 | 615.7, 613.7 [M + H] |
| 181 | Ethyl 6-bromo-5-hydroxy-1-methyl-4-[(2-methyl-1-imidazolyl)methyl]-2-[(benzo[d]imidazol-2-yl)thiomethyl]-1H-indole-3-carboxylate hydrochloride | 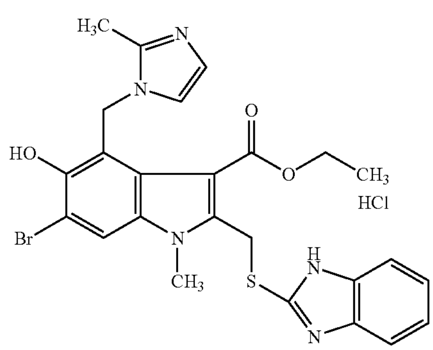 | 556.4, 554.4 [M + H] |

TABLE 6-continued

| Example No. | Chemical Name | Structure | MS m/z |
|---|---|---|---|
| 182 | Ethyl 6-bromo-1-cyclopropyl-5-hydroxy-4-[(2-methyl-1-imidazolyl)methyl]-2-[(4-thiazolylmethyl)sulfinylmethyl]-1H-indole-3-carboxylate dihydrochloride | 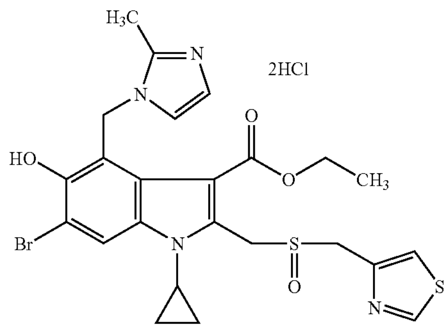 | 579.1, 577.1 [M + H] |
| 183 | Ethyl 6-bromo-1-cyclopropyl-5-hydroxy-4-[(2-methyl-1-imidazolyl)methyl]-2-[(2-fluorobenzyl)sulfinylmethyl]-1H-indole-3-carboxylate | 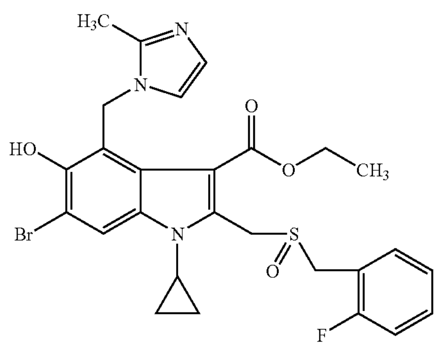 | 590.2, 588.3 [M + H] |
| 184 | Ethyl 6-bromo-5-hydroxy-1-methyl-4-[(2-methyl-1-imidazolyl)methyl]-2-[(4-fluorobenzyl)sulfinylmethyl]-1H-indole-3-carboxylate | 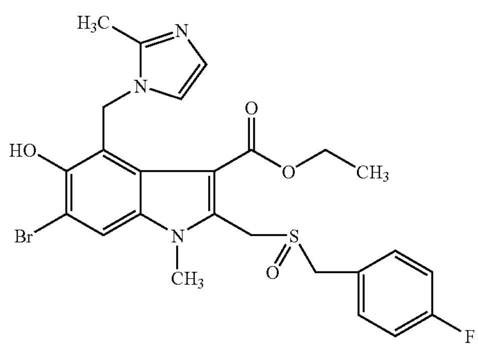 | 564.3, 562.3 [M + H] |
| 185 | Ethyl 6-bromo-5-hydroxy-1-methyl-4-[(2-methyl-1-imidazolyl)methyl]-2-[(4-fluorobenzyl)sulfonylmethyl]-1H-indole-3-carboxylate | 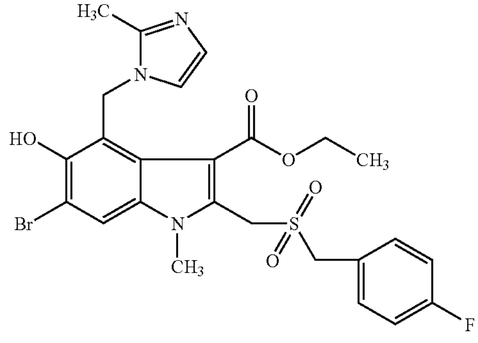 | 580.4, 578.4 [M + H] |

TABLE 6-continued

| Example No. | Chemical Name | Structure | MS m/z |
|---|---|---|---|
| 186 | Ethyl 6-bromo-1-cyclopropyl-5-hydroxy-4-[(1H-1,2,4-triazol-1-yl)methyl]-2-[(2-fluorobenzyl)thiomethyl]-1H-indole-3-carboxylate | 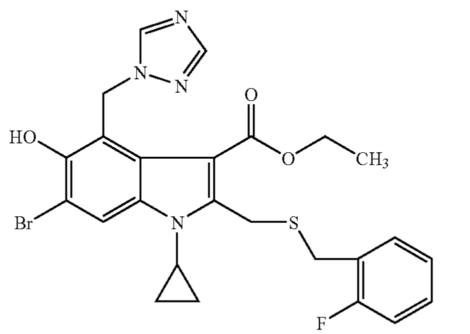 | 583.1, 581.1 [M + H] |
| 187 | Ethyl 6-bromo-5-hydroxy-1-methyl-4-[(1H-1,2,4-triazol-1-yl)methyl]-2-[(4-fluorobenzyl)thiomethyl]-1H-indole-3-carboxylate | 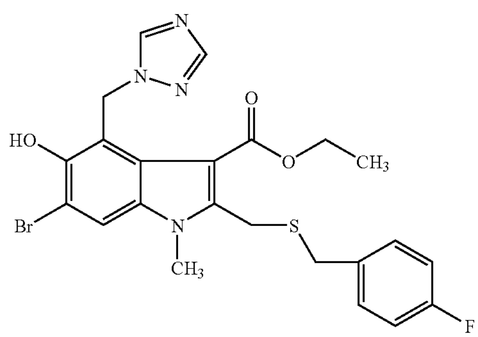 | 535.5, 533.4 [M + H] |
| 188 | Ethyl 6-bromo-1-cyclopropyl-4-(guanidinylmethyl)-5-hydroxy-2-(benzylthiomethyl)-1H-indole-3-carboxylate | 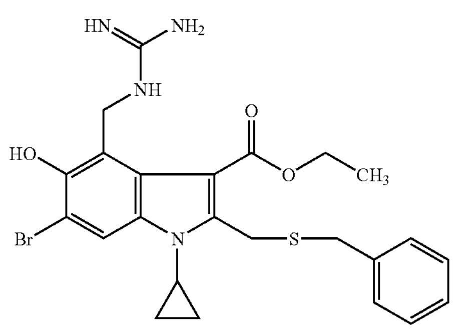 | 533.2, 531.1 [M + H] |
| 189 | Ethyl 6-bromo-4-(guanidinylmethyl)-5-hydroxy-1-methyl-2-[(benzo[d]imidazol-2-yl)thiomethyl]-1H-indole-3-NL carboxylate | 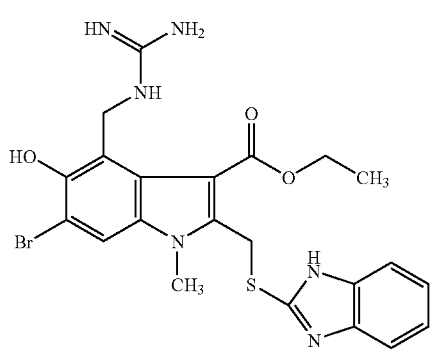 | 533.7, 531.7 [M + H] |

TABLE 6-continued

| Example No. | Chemical Name | Structure | MS m/z |
|---|---|---|---|
| 190 | Ethyl 6-bromo-1-cyclopropyl-5-hydroxy-4-[(1-imidazolyl)methyl]-2-[(5-methyl-4-imidazolylmethyl)thiomethyl]-1H-indole-3-carboxylate | 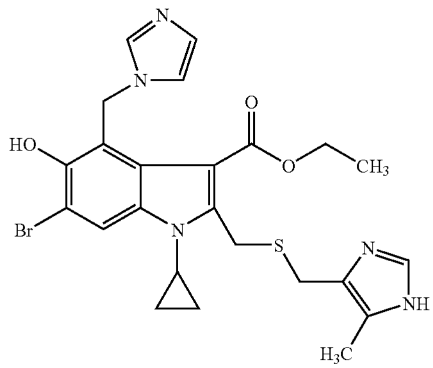 | 546.4, 544.4 [M + H] |
| 191 | Ethyl 6-bromo-1-cyclopropyl-5-hydroxy-4-[(2-methyl-1-imidazolyl)methyl]-2-[(5-methyl-4-imidazolylmethyl)thiomethyl]-1H-indole-3-carboxylate | 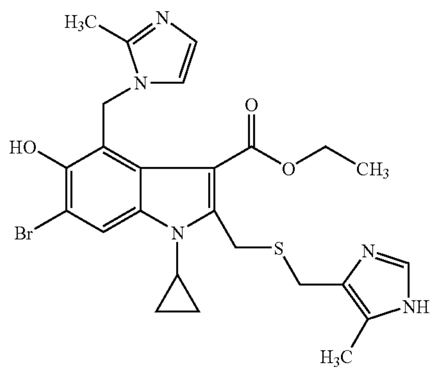 | 558.2, 560.2 [M + H] |
| 192 | Ethyl 6-bromo-5-hydroxy-1-methyl-4-[(1-imidazolyl)methyl]-2-(phenylethylthiomethyl)-1H-indole-3-carboxylate | 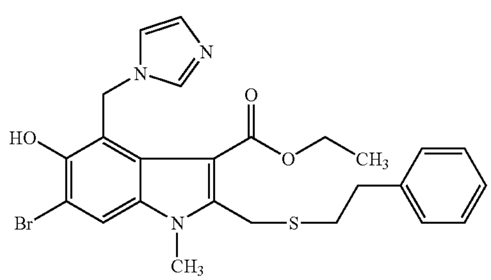 | 530.4, 528.4 [M + H] |
| 193 | Ethyl 6-bromo-5-hydroxy-4-[(1-imidazolyl)methyl]-1-methyl-2-(phenylethylsulfinylmethyl)-1H-indole-3-carboxylate | 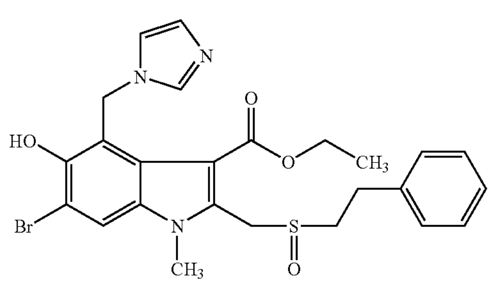 | 546.3, 544.3 [M + H] |

TABLE 6-continued

| Example No. | Chemical Name | Structure | MS m/z |
|---|---|---|---|
| 194 | Ethyl 6-bromo-1-cyclopropyl-5-hydroxy-4-[(1-imidazolyl)methyl]-2-(phenylethylthiomethyl)-1H-indole-3-carboxylate | 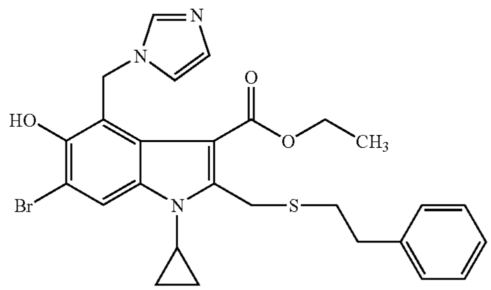 | 556.1, 554.1 [M + H] |

The compounds of Examples 195-205 were synthesized following the appropriate method in general procedures 1-4, respectively. (Table 7)

TABLE 7

| Example No. | Chemical Name | Structure | MS m/z |
|---|---|---|---|
| 195 | Ethyl 6-bromo-1-cyclopropyl-5-hydroxy-4-(piperidinomethyl)-2-(phenylpropylthiomethyl)-1H-indole-3-carboxylate | 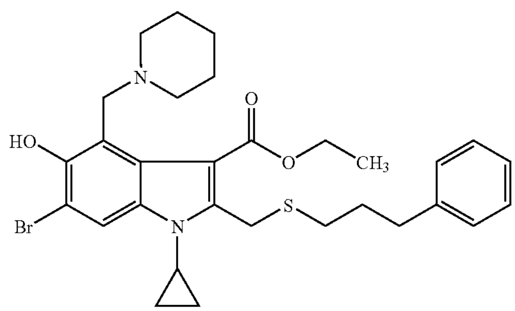 | 587.2, 585.2 [M + H] |
| 196 | Ethyl 6-bromo-1-cyclopropyl-5-hydroxy-4-(morpholinomethyl)-2-(phenylpropylthiomethyl)-1H-indole-3-carboxylate | 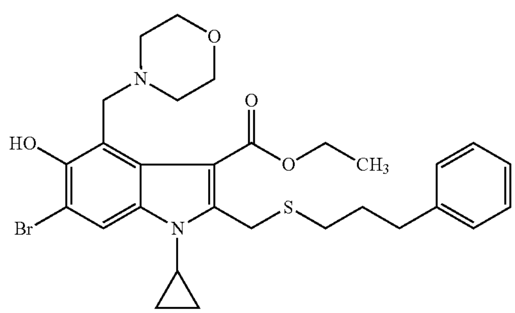 | 589.2, 587.2 [M + H] |
| 197 | Ethyl 6-bromo-1-cyclopropyl-5-hydroxy-4-[(4-methyl-1-piperazinyl)methyl]-2-(phenylpropylthiomethyl)-1H-indole-3-carboxylate | 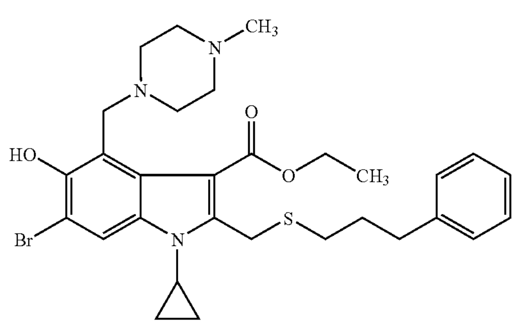 | 602.5, 600.5 [M + H] |

TABLE 7-continued

| Example No. | Chemical Name | Structure | MS m/z |
|---|---|---|---|
| 198 | Ethyl 6-bromo-1-cyclopropyl-4-[(dimethylamino)methyl]-5-hydroxy-2-(phenylethylthiomethyl)-1H-indole-3-carboxylate hydrochloride | 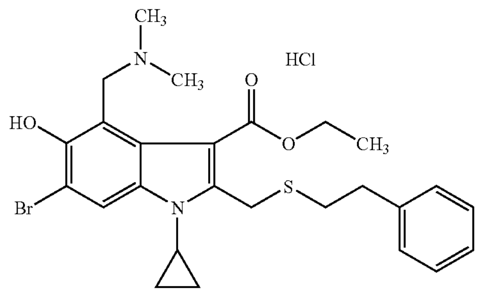 | 533.1, 531.1 [M + H] |
| 199 | Ethyl 6-bromo-1-cyclopropyl-5-hydroxy-4-(1-pyrrolidinylmethyl)-2-(phenylethylthiomethyl)-1H-indole-3-carboxylate hydrochloride | 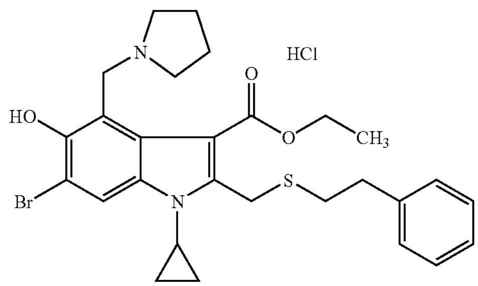 | 559.7, 557.7, [M + H] |
| 200 | Ethyl 6-bromo-1-cyclopropyl-5-hydroxy-4-(morpholinomethyl)-2-(phenylethylthiomethyl)-1H-indole-3-carboxylate | 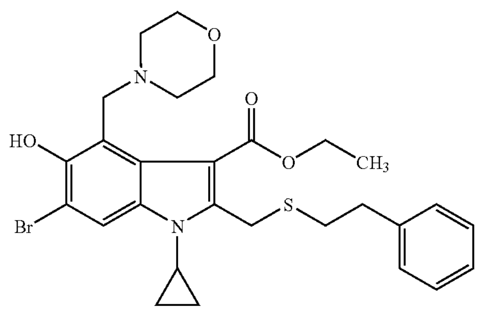 | 575.2, 573.3 [M + H] |
| 201 | Ethyl 6-bromo-5-hydroxy-1-methyl-4-(morpholinomethyl)-2-(phenylethylthiomethyl)-1H-indole-3-carboxylate | 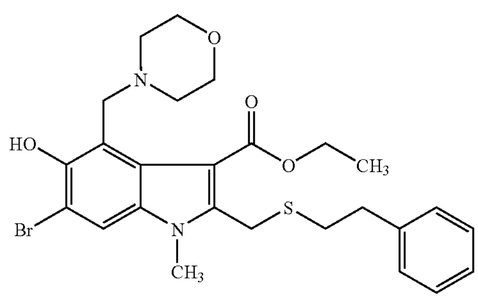 | 533.1, 531.1 [M + H] |
| 202 | Ethyl 6-bromo-1-cyclopropyl-4-[(dimethylamino)methyl]-5-hydroxy-2-(phenylethylsulfinylmethyl)-1H-indole-3-carboxylate | 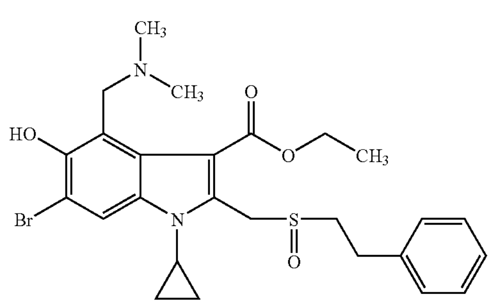 | 549.1, 547.1 [M + H] |

TABLE 7-continued

| Example No. | Chemical Name | Structure | MS m/z |
|---|---|---|---|
| 203 | Ethyl 6-bromo-4-[(dimethylamino)methyl]-5-hydroxy-1-methyl-2-(phenylethylsulfonylmethyl)-1H-indole-3-carboxylate | 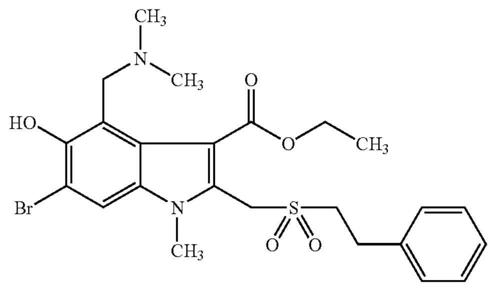 | 539.3, 537.3 [M + H] |
| 204 | Ethyl 6-bromo-5-hydroxy-1-methyl-4-(1-pyrrolidinylmethyl)-2-(phenylethylsulfonylmethyl)-1H-indole-3-carboxylate | 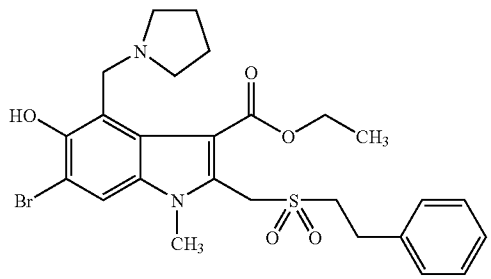 | 565.2, 563.2 [M + H] |
| 205 | Ethyl 6-bromo-1-cyclopropyl-5-hydroxy-4-(morpholinomethyl)-2-[(5-methyl-4-imidazolylmethyl)sulfinylmethyl]-1H-indole-3-carboxylate | 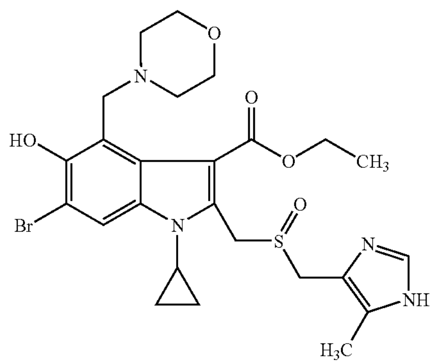 | 581.3, 579.3 [M + H] |

The Pharmacological Study of the Compounds of Present Invention

The 5-hydroxy-indole-3-carboxylate derivatives defined by formula I or II were evaluated for their in vitro anti-hepatitis B virus (HBV) activities and anti-HIV-1 protease activities.

In Vitro Anti-HBV Activity

All compounds were evaluated for their anti-HBV activities, namely the ability to inhibit the replication of HBV DNA and the production of HBsAg and HBeAg in HBV-infected 2.2.15 cells.

The samples were dissolved in DMSO for appropriate concentrations, and then each was diluted 3-fold with culture medium. The 2.2.15 cells were planted into 96-well culture plates. After 36 h, several dilutions of samples and the positive control drug Lamivudine (3TC, GlaxoWellcome Co.) were added respectively, and after 96 h, the culture medium of different dilutions was changed. The culture supernatants and 2.2.15 cells were collected respectively on the $8^{th}$ plant day. The secretion concentrations of HBsAg and HBeAg in the culture supernatants were measured by RIA on SPRIA Kit for Detection of HBsAg and HBeAg (Beijing North Institute of Biological Technology), and the replication of HBV DNA was measured by dot hybridization with $a^{32}$PdCTP (FuRui Biological Technology Ltd., China). The $IC_{50}$ and SI are as follows:

TABLE 8

Table 8 the in vitro anti-HBV activities of the compound of Examples

| Compounds | $TC_{50}$ (ug/ml) | HBsAg $IC_{50}$ (ug/ml) | SI | HBeAg $IC_{50}$ (ug/ml) | SI | DNA replication $IC_{50}$ (ug/ml) | SI |
|---|---|---|---|---|---|---|---|
| Example 17 | 62.50 | — | — | — | — | 17.82 | 3.5 |
| Example 19 | 37.04 | — | — | — | — | 13 | 2.85 |
| Example 52 | 64.15 | 4.79 | 13.39 | — | — | 3.51 | 18.27 |
| Example 55 | 21.56 | — | — | — | — | 2.2 | 9.7 |

TABLE 8-continued

Table 8 the in vitro anti-HBV activities of the compound of Examples

| Compounds | TC$_{50}$ (ug/ml) | HBsAg IC$_{50}$ (ug/ml) | SI | HBeAg IC$_{50}$ (ug/ml) | SI | DNA replication IC$_{50}$ (ug/ml) | SI |
|---|---|---|---|---|---|---|---|
| Example 57 | 51.53 | — | — | — | — | 17 | 3.03 |
| Example 58 | >500 | — | — | — | — | 57.6 | >8.7 |
| Example 59 | 288.68 | — | — | — | — | 26.64 | 10.8 |
| Example 64 | 24.69 | — | — | — | — | 0.76 | 32.48 |
| Example 67 | 34.35 | — | — | — | — | 5.4 | 6.35 |
| Example 71 | 38.32 | 18.36 | 2.09 | — | — | 23.88 | 1.60 |
| Example 72 | 106.83 | — | — | 15.41 | 6.9 | 15.41 | 6.9 |
| Example 77 | 74.07 | — | — | — | — | 18.09 | 4.09 |
| Example 79 | 17.12 | 6.30 | 2.72 | — | — | 4.47 | 3.83 |
| Example 80 | <0.91 | — | — | — | — | 0.27 | 3.37 |
| Example 81 | 35.61 | — | — | — | — | 0.715 | 49.8 |
| Example 82 | 14.25 | 7.83 | 1.82 | — | — | 6.10 | 2.34 |
| Example 83 | 35.61 | 18.31 | 1.94 | — | — | 6.38 | 5.58 |
| Example 84 | 24.69 | — | — | — | — | 0.58 | 42.57 |
| Example 85 | 14.26 | — | — | — | — | 1.52 | 9.38 |
| Example 86 | 7.13 | — | — | — | — | 0.64 | 11.14 |
| Example 87 | 21.39 | — | — | — | — | 0.53 | 40.35 |
| Example 94 | 53.42 | 7.37 | 7.25 | — | — | — | — |
| Example 116 | 8.12 | — | — | — | — | 2.56 | 3.17 |
| Example 117 | 55.56 | — | — | — | — | 11.4 | 4.87 |
| Example 119 | 21.11 | — | — | — | — | 3.6 | 5.8 |
| Example 122 | 48.1 | 11.37 | 4.23 | — | — | 13.61 | 3.54 |
| Example 125 | 48.1 | — | — | — | — | 8.76 | 5.49 |
| Example 126 | 35.61 | — | — | — | — | 6.36 | 5.60 |
| Example 128 | 53.42 | 7.23 | 7.39 | 8.06 | 6.63 | — | — |
| Example 130 | 24.69 | — | — | — | — | 5.94 | 4.16 |
| Example 133 | 40.0 | — | — | — | — | 6.37 | 6.28 |
| Example 134 | 53.42 | — | — | — | — | 3.8 | 19.1 |
| Example 135 | 53.42 | — | — | — | — | 2.4 | 22.3 |
| Example 137 | 160.2 | — | — | — | — | 35.48 | 4.51 |
| Example 138 | 18.52 | — | — | — | — | 5 | 3.74 |
| Example 142 | 106.83 | — | — | — | — | 23.78 | 4.49 |
| Example 146 | 40.0 | — | — | — | — | 13.08 | 3.06 |
| Example 149 | 95.45 | — | — | — | — | 3.41 | 27.99 |
| Example 151 | 64.15 | — | — | — | — | 1.8 | 35.6 |
| Example 152 | 192.45 | — | — | — | — | 10.2 | 18.8 |
| Example 153 | 125 | 62.16 | 2.01 | — | — | 29.30 | 4.27 |
| Example 154 | 18.52 | — | — | — | — | 5.2 | 3.63 |
| Example 158 | 125 | — | — | — | — | 26.84 | 4.66 |
| Example 162 | 128.30 | — | — | — | — | 51.72 | 2.48 |
| Example 163 | 21.39 | — | — | — | — | 0.68 | 31.45 |
| Example 164 | 17.7 | — | — | — | — | 2.0 | 8.9 |
| Example 165 | 7.76 | — | — | — | — | 3.14 | 2.47 |
| Example 166 | 53.42 | — | — | — | — | 7.53 | 7.09 |
| Example 168 | 35.61 | — | — | — | — | 7.04 | 5.06 |
| Example 173 | 24.69 | — | — | — | — | 5.04 | 4.90 |
| Example 175 | 35.61 | 2.45 | 14.53 | — | — | 4.65 | 7.66 |
| Example 177 | 106.83 | 31.46 | 3.39 | — | — | 15.89 | 6.72 |
| Example 179 | 10.69 | 1.88 | 5.69 | 1.91 | 5.60 | — | — |
| Example 180 | 51.36 | — | — | — | — | 3.56 | 14.43 |
| Example 181 | 21.38 | 1.55 | 13.79 | — | — | — | — |
| Example 182 | 64.15 | 4.66 | 13.77 | 7.69 | 8.34 | — | — |
| Example 183 | 37.04 | — | — | — | — | 3.45 | 10.74 |
| Example 184 | 53.42 | — | — | — | — | 0.94 | 56.83 |
| Example 185 | 12.35 | — | — | — | — | 1.30 | 9.5 |
| Example 189 | 258.69 | 12.52 | 20.66 | 27.96 | 9.25 | 12.37 | 20.91 |
| 3TC | 1600 | — | — | — | — | 228.0 | 7.0 |

Anti-HIV-1 Protease Activity

HIV-1 protease can cut the fluorescence labeled substrate under optimal condition and reaction system, so the activity of enzyme is determined by the fluorescence in the product of enzymatic reaction. The samples are added into the reaction system to observe the inhibitive effect on the enzyme.

The samples and the reference drug Indinavir (Glaxo Co.) were dissolved in DMSO or redistilled water for appropriate concentration. Each was diluted 5-fold and then added into the buffer containing fluorescence labeled substrate (MP Co.). The genetically engineered target enzyme (HIV-1 protease, preserved at −85° C.) was added to the buffer and incubated under the optimal reaction condition. The fluorescence was determined by FLUO star Galaxy fluorometer.

TABLE 9

Table 9 the inhibition ratio and $IC_{50}$ of the samples at different concentrations (initial concentration: 250 μg/mL)

| Compounds | C (ug/mL) | | | | | |
|---|---|---|---|---|---|---|
| | 250 (ug/ml) | 50 (ug/ml) | 10 (ug/ml) | 2.0 (ug/ml) | 0.5 (ug/ml) | $IC_{50}$ (ug/ml) |
| Example 17 | 27.6 | −17.3 | −13.0 | −8.3 | −6.1 | — |
| Example 19 | 63.9 | 20.7 | −8.9 | −8.9 | −5.6 | 133.7 |
| Example 138 | 75.7 | 12.7 | 6.4 | −2.3 | 6.8 | 63.5 |
| Example 57 | 41.0 | 15.5 | 1.9 | 9.2 | 6.4 | — |
| Example 58 | 37.4 | 22.9 | 15.9 | 11.6 | 11.7 | — |
| Example 67 | 19.3 | 0.5 | 9.4 | 10.5 | 3.2 | — |
| Example 55 | 98.0 | 30.5 | 0.1 | 6.7 | 2.1 | 26.43 |
| Example 131 | 55.1 | 7.7 | 7.1 | 14.6 | 4.6 | 156.07 |
| Example 153 | 75.3 | 24.1 | 11.2 | 14.7 | 7.2 | 70.11 |
| Example 116 | 37.5 | 11.1 | −1.5 | −2.4 | 0.4 | — |
| Example 154 | 109.3 | 19.8 | 4.8 | 13.2 | 3.2 | 23.96 |
| Example 158 | 30.1 | 8.9 | −3.7 | 3.6 | 5.2 | — |
| Example 160 | 97.8 | 71.8 | 29.1 | 11.7 | 6.1 | 12.69 |

Anti-Influenza Virus Activity

The samples were examined for the inhibitive effect on cytopathogenicity of influenza A virus to Madin-Darby canine kidney (MDCK) cells.

The samples were dissolved in DMSO for appropriate concentration, and then each was diluted twofold in culture medium. The MDCK cells were planted into 96-well culture plates. After 24 h, the cells were infected by influenza strain A/jifang/90-15 ($10^{-3}$). The virus was washed after 3 h. Several dilutions of samples and the reference drug Ribovirin (Hubei KeYi pharmaceutical factory) were added respectively. Cytopathic effect (CPE) of the cells was examined after 30 h. The 50% inhibitive concentrations ($IC_{50}$) of the samples for influenza A virus were determined by the method of Reed-Muench.

TABLE 10 the in vitro anti-influenza virus activity of the compounds of Examples

| Compounds | Influenza strain A/jifang/90-15 | | |
|---|---|---|---|
| | $TC_{50}$ (μg/ml) | $IC_{50}$ (μg/ml) | SI |
| Example 3 | 12.4 | 7.81 | 1.59 |
| Example 5 | 49.51 | 7.81 | 6.34 |
| Example 14 | 2.48 | 0.92 | 2.7 |
| Example 25 | 125.0 | 22.10 | 5.66 |
| Example 91 | 293.37 | 15.63 | 18.77 |
| Example 92 | 18.34 | 7.81 | 2.35 |
| Example 100 | 49.61 | 22.10 | 2.24 |
| Example 104 | 148.65 | 13.32 | 11.16 |

TABLE 10-continued the in vitro anti-influenza virus activity of the compounds of Examples

| Compounds | Influenza strain A/jifang/90-15 | | |
|---|---|---|---|
| | $TC_{50}$ (μg/ml) | $IC_{50}$ (μg/ml) | SI |
| Example 126 | 44.19 | 11.05 | 4.0 |
| Example 176 | 125 | 15.63 | 8.0 |
| Example 178 | 78.75 | 7.81 | 10.08 |
| Example 186 | 62.5 | 9.17 | 6.82 |
| Example 187 | 44.19 | 26.63 | 1.66 |
| Example 188 | 39.37 | 9.85 | 4.0 |
| Abidol | 62.5 | 23.2 | 2.69 |
| Ribovirin | >1000 | >33.81 | >29.57 |

What is claimed is:

1. A compound of formula I, or racemic mixture or optical isomers or pharmaceutically acceptable salts thereof:

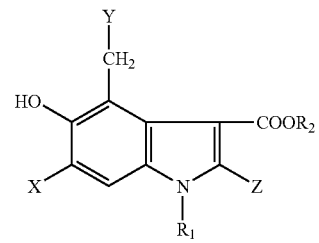

wherein:
$R_1$ is H, $C_1$-$C_6$ alkyl, or $C_3$-$C_7$ cycloalkyl, wherein said alkyl and cycloalkyl are optionally substituted with 1 to 2 substituents selected from the group consisting of hydroxyl, nitro, halo, cyano, trifluoromethyl and trifluoromethoxy;

$R_2$ is $C_1$-$C_6$ alkyl, wherein the alkyl is optionally substituted with 1 to 2 substituents selected from the group consisting of hydroxyl, nitro, halo, cyano, trifluoromethyl and trifluoromethoxy;

X is H, nitro, halo, cyano, trifluoromethyl or trifluoromethoxy;

Y is —$NR_3R_4$;

Z is

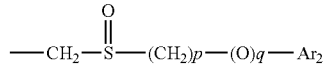

or

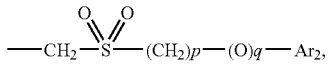

wherein p represents an integer from 0 to 4, q represents the integer 0 or 1, and when p represents the integer 0, q represents the integer 0;

$R_3$ and $R_4$ are covalently bonded together with the nitrogen to which they are attached to form guanidyl, 5- to 10-membered heterocyclic radical or 5- to 10-membered heteroaryl radical, wherein except for the nitrogen atom to which $R_3$ and $R_4$ are attached, said heterocyclic and heteraryl radicals may have optionally 1 to 4 heteroatoms selected from N, O or S, and wherein except for the nitrogen atom to which $R_3$ and $R_4$ are attached, said heterocyclic radical may optionally have 1 to 2 carbon-carbon double bond or triple bond, said heterocyclic and heteroaryl radicals can be optionally substituted with 1 to 3 same or different $R_8$;

$Ar_2$ represents $C_6$-$C_{10}$ aryl, 5- to 10-membered heteroaryl radical or 5- to 10-membered heterocyclic radical, wherein said heteroaryl and heterocyclic radicals can have 1 to 3 heteroatoms selected from N, O or S and $Ar_2$ can be optionally substituted with 1 to 3 same or different $R_9$;

$R_8$ represents $C_1$-$C_4$ alkyl, $C_1$-$C_4$ alkoxyl, halo, hydroxyl, cyano, carboxyl, ester group or nitro; and $R_9$ represents $C_1$-$C_6$ alkyl, $C_1$-$C_6$ alkoxyl, hydroxyl, $C_1$-$C_6$ alkyl or $C_1$-$C_6$ alkoxyl which is optionally substituted with hydroxyl, amino or halo, $C_1$-$C_6$ alkylsulfanyl, carboxyl group which can be free or form ester group, amide, or salts, halo, $C_1$-$C_6$ alkylacyl, nitro, cyano, amino, $C_1$-$C_6$ alkylamide group, or amine group substituted with $(C_1$-$C_6$ alkyl$)_n$, where n is 1 or 2.

2. The compound of formula I, or racemic mixture or optical isomers or pharmaceutically acceptable salts thereof according to claim 1, wherein:
X is H, or halo; and
$Ar_2$ represents $C_6$-$C_{10}$ aryl or 5- to 10-membered heteroaryl radical.

3. The compound of formula I, or racemic mixture or optical isomers or pharmaceutically acceptable salts thereof according to claim 2, wherein:
$R_1$ is H, $C_1$-$C_4$ alkyl or $C_3$-$C_7$ cycloalkyl;
$R_2$ is $C_1$-$C_4$ alkyl; and
$Ar_2$ represents $C_6$-$C_{10}$ aryl or $C_5$-$C_{10}$ heteroaryl, wherein the heteroaryl may contain 1 to 2 heteroatom(s) selected from N, O or S.

4. The compound of formula I, or racemic mixture or optical isomers or pharmaceutically acceptable salts thereof according to claim 3, wherein:
$R_1$ is $C_1$-$C_4$ alkyl or $C_3$-$C_7$ cycloalkyl;
$R_3$ and $R_4$ are covalently bonded together with the nitrogen to which they are attached to form guanidyl, 5- to 6-membered heterocyclic radical or 5- to 6-membered heteroaryl radical, wherein except for the nitrogen atom to which $R_3$ and $R_4$ are attached, said heterocyclic and heteroaryl radicals may have optionally 1 to 4 heteroatoms selected from N, O or S, and wherein said heterocyclic and heteroaryl radicals can be optionally substituted with 1 to 3 same or different $R_8$; and
$Ar_2$ represents phenyl, substituted phenyl or 5- to 6-membered heteroaryl, wherein said heteroaryl radical may have 1 to 2 heteroatoms selected from N, O or S and $Ar_2$ can be optionally substituted with 1 to 3 same or different $R_9$.

5. The compound of formula I, or racemic mixture or optical isomers or pharmaceutically acceptable salts thereof according to claim 4, wherein:
$R_1$ is methyl, ethyl, propyl, isopropyl, or cyclopropyl;
Y is —$NR_3R_4$; and
Z is

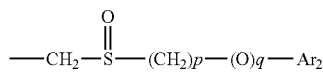

or

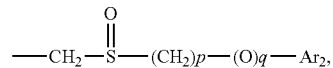

wherein p represents an integer from 0 to 2, q represents the integer 0 or 1, and when p is 0, q is 0;
$R_3$ and $R_4$ are covalently bonded together with the nitrogen to which they are attached to form guanidyl, 4-morpholino, 4-methyl-1-piperazinyl, 1-piperidino, 1-pyrrolidinyl, 1H-1,2,4-triazol-1-yl, 1-imidazolyl, 2-methyl-1-imidazolyl or 1H-tetrazol-1-yl.

6. The compound of formula I, or racemic mixture or optical isomers or pharmaceutically acceptable salts thereof according to claim 5, wherein:
Z is

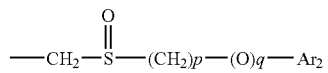

or

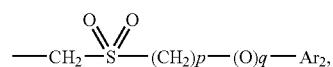

wherein p represents the integer from 0 to 2 and q represents the integer 0;
$R_3$ and $R_4$ are covalently bonded together with the nitrogen to which they are attached to form guanidyl, 4-morpholino, 4-methyl-1-piperazinyl, 1-piperidino, 1-pyrrolidinyl, 1H-1,2,4-triazol-1-yl, 1-imidazolyl, 2-methyl-1-imidazolyl or 1H-tetrazol-1-yl; and
$Ar_2$ represents phenyl or phenyl optionally substituted with 1 to 3 same or different $R_9$.

7. The compound of formula I, or racemic mixture or optical isomers or pharmaceutically acceptable salts thereof according to claim 1, wherein:
$Ar_2$ represents phenyl, substituted phenyl or 5- to 6-membered heteroaryl, wherein the heteroaryl and heterocyclic radicals may contain 1 to 3 heteroatoms selected from N, O or S and $Ar_2$ can be optionally substituted with 1 to 3 same or different $R_9$.

8. The compound of formula I, or racemic mixture or optical isomers or pharmaceutically acceptable salts thereof according to claim 7, wherein:
$Ar_2$ represents phenyl or phenyl group substituted with 1 to 3 halo.

9. The compound of formula I, or racemic mixture or optical isomers or pharmaceutically acceptable salts thereof according to claim 1, wherein:
X is H, or bromine.

10. A compound or racemic mixture or optical isomers or pharmaceutically acceptable salts thereof according to claim 1, selected from the group consisting of:
Ethyl 6-bromo-5-hydroxy-1-methyl-2-[(2-methylphenyl)sulfinylmethyl]-4-(morpholinomethyl)-1H-indole-3-carboxylate;
Ethyl 6-bromo-2-[(4-fluorophenyl)sulfinylmethyl]-5-hydroxy-1-methyl-4-(morpholinomethyl)-1H-indole-3-carboxylate;

Ethyl 6-bromo-2-[(3-chlorophenyl)sulfinylmethyl]-5-hydroxy-1-methyl-4-(morpholinomethyl)-1H-indole-3-carboxylate;
Ethyl 6-bromo-5-hydroxy-1-methyl-4-(morpholinomethyl)-2-[(4-fluorobenzyl)sulfinylmethyl]-1H-indole-3-carboxylate;
Ethyl 6-bromo-1-cyclopropyl-2-[(3,4-difluorophenyl)sulfinylmethyl]-5-hydroxy-4-[(4-methyl-1-piperazinyl)methyl]-1H-indole-3-carboxylate dihydrochloride;
Ethyl 6-bromo-2-[(2-furylmethyl)sulfinylmethyl]-5-hydroxy-1-methyl-4-(1-pyrrolidinylmethyl)-1H-indole-3-carboxylate;
Ethyl 5-hydroxy-2-[(3-methoxyphenyl)sulfonylmethyl]-1-methyl-4-(1-pyrrolidinylmethyl)-1H-indole-3-carboxylate;
Ethyl 2-[(3-furylmethyl)sulfinylmethyl]-5-hydroxy-1-methyl-4-(piperidinomethyl)-1H-indole-3-carboxylate;
Ethyl 6-bromo-5-hydroxy-1-methyl-4-(1-pyrrolidinylmethyl)-2-[(4-trifluoromethylphenyl)sulfonylmethyl]-1H-indole-3-carboxylate;
Ethyl 6-bromo-1-cyclopropyl-5-hydroxy-4-(1-pyrrolidinylmethyl)-2-[(3-trifluoromethylphenyl)sulfonylmethyl]-1H-indole-3-carboxylate;
Ethyl 6-bromo-5-hydroxy-1-methyl-4-(1-pyrrolidinylmethyl)-2-[(4-fluorobenzyl)sulfonylmethyl]-1H-indole-3-carboxylate;
Ethyl 1-cyclopropyl-5-hydroxy-4-(1-pyrrolidinylmethyl)-2-[(2-furylmethyl)sulfonylmethyl]-1H-indole-3-carboxylate;
Ethyl 6-bromo-5-hydroxy-1-methyl-4-(1-piperidinomethyl)-2-[(4-fluorobenzyl)sulfinylmethyl]-1H-indole-3-carboxylate;
Ethyl 6-bromo-2-[(3-fluorobenzyl)sulfinylmethyl]-5-hydroxy-1-methyl-4-(4-morpholinomethyl)-1H-indole-3-carboxylate;
Ethyl 6-bromo-5-hydroxy-4-[(1-imidazolyl)methyl]-1-methyl-2-(phenylsulfinylmethyl)-1H-indole-3-carboxylate;
Ethyl 6-bromo-1-cyclopropyl-5-hydroxy-4-(1-imidazolylmethyl)-2-[(4-fluorophenyl)sulfinylmethyl]-1H-indole-3-carboxylate;
Ethyl 6-bromo-1-cyclopropyl-2-[(3,4-difluorophenyl)sulfinylmethyl]-5-hydroxy-4-(1-imidazolylmethyl)-1H-indole-3-carboxylate;
Ethyl 6-bromo-2-[(4-fluorophenyl)sulfinylmethyl]-5-hydroxy-4-[(1-imidazolyl)methyl]-1-methyl-1H-indole-3-carboxylate;
Ethyl 6-bromo-5-hydroxy-4-[(1-imidazolyl)methyl]-1-methyl-2-[(2-fluorophenyl)sulfinylmethyl]-1H-indole-3-carboxylate;
Ethyl 2-(benzylsulfinylmethyl)-6-bromo-1-cyclopropyl-5-hydroxy-4-[(1-imidazolyl)methyl]-1H-indole-3-carboxylate;
Ethyl 6-bromo-1-cyclopropyl-5-hydroxy-4-[(1-imidazolyl)methyl]-2-[(4-thiazolylmethyl)sulfinylmethyl]-1H-indole-3-carboxylate;
Ethyl 6-bromo-1-cyclopropyl-5-hydroxy-4-[(1-imidazolyl)methyl]-2-[(2-furylmethyl)sulfinylmethyl]-1H-indole-3-carboxylate;
Ethyl 6-bromo-5-hydroxy-1-methyl-4-[(2-methyl-1-imidazolyl)methyl]-2-[(3,4-difluorophenyl)sulfinylmethyl]-1H-indole-3-carboxylate;
Ethyl 6-bromo-5-hydroxy-1-methyl-4-[(2-methyl-1-imidazolyl)methyl]-2-[(3-methylphenyl)sulfinylmethyl]-1H-indole-3-carboxylate;
Ethyl 6-bromo-5-hydroxy-1-methyl-4-[(2-methyl-1-imidazolyl)methyl]-2-[(2-methoxyphenyl)sulfinylmethyl]-1H-indole-3-carboxylate;
Ethyl 6-bromo-1-cyclopropyl-2-[(2,6-dichlorophenyl)sulfinylmethyl]-5-hydroxy-4-[(2-methyl-1-imidazolyl)methyl]-1H-indole-3-carboxylate;
Ethyl 6-bromo-1-cyclopropyl-2-[(4-fluorophenyl)sulfinylmethyl]-5-hydroxy-4-[(2-methyl-1-imidazolyl)methyl]-1H-indole-3-carboxylate;
Ethyl 5-hydroxy-1-methyl-4-[(2-methyl-1-imidazolyl)methyl]-2-[(4-methylphenyl)sulfinylmethyl]-1H-indole-3-carboxylate;
Ethyl 6-bromo-5-hydroxy-1-methyl-2-(phenylsulfinylmethyl)-4-[(1H-1,2,4-triazol-1-yl)methyl]-1H-indole-3-carboxylate;
Ethyl 6-bromo-5-hydroxy-1-methyl-4-[(1H-1,2,4-triazol-1-yl)methyl]-2-[(4-fluorobenzyl)sulfinylmethyl]-1H-indole-3-carboxylate;
Ethyl 6-bromo-1-cyclopropyl-5-hydroxy-4-[(1-imidazolyl)methyl]-2-[(2-furylmethyl)sulfonylmethyl]-1H-indole-3-carboxylate;
Ethyl 6-bromo-5-hydroxy-4-[(1-imidazolyl)methyl]-1-methyl-2-[(4-fluorobenzyl)sulfonylmethyl]-1H-indole-3-carboxylate;
Ethyl 1-cyclopropyl-5-hydroxy-4-[(1-imidazolyl)methyl]-2-[(4-methylphenyl)sulfonylmethyl]-1H-indole-3-carboxylate;
Ethyl 6-bromo-1-cyclopropyl-5-hydroxy-4-[(2-methyl-1-imidazolyl)methyl]-2-[(2-fluorobenzyl)sulfonylmethyl]-1H-indole-3-carboxylate;
Ethyl 6-bromo-5-hydroxy-1-methyl-4-[(2-methyl-1-imidazolyl)methyl]-2-(phenylsulfonylmethyl)-1H-indole-3-carboxylate;
Ethyl 6-bromo-5-hydroxy-1-methyl-4-[(2-methyl-1-imidazolyl)methyl]-2-(benzylsulfonylmethyl)-1H-indole-3-carboxylate;
Ethyl 6-bromo-5-hydroxy-4-[(1-imidazolyl)methyl]-1-methyl-2-[(4-trifluoromethylphenyl)sulfinyl-methyl]-1H-indole-3-carboxylate;
Ethyl 6-bromo-1-cyclopropyl-5-hydroxy-4-[(2-methyl-1-imidazolyl)methyl]-2-(benzylsulfonylmethyl)-1H-indole-3-carboxylate;
Ethyl 6-bromo-5-hydroxy-1-methyl-4-[(2-methylimidazolyl)methyl]-2-[(1-adamantanyl)sulfonylmethyl]-1H-indole-3-carboxylate;
Ethyl 6-bromo-5-hydroxy-1-methyl-4-[(2-methyl-1-imidazolyl)methyl]-2-[(4-trifluoromethylphenyl)sulfonyl-methyl]-1H-indole-3-carboxylate;
Ethyl 6-bromo-1-cyclopropyl-5-hydroxy-4-[(2-methyl-1-imidazolyl)methyl]-2-[(4-thiazolylmethyl)sulfinylmethyl]-1H-indole-3-carboxylate hydrochloride;
Ethyl 6-bromo-1-cyclopropyl-5-hydroxy-4-[(2-methyl-1-imidazolyl)methyl]-2-[(2-fluorobenzyl)sulfinyl methyl]-1H-indole-3-carboxylate;
Ethyl 6-bromo-5-hydroxy-1-methyl-4-[(2-methyl-1-imidazolyl)methyl]-2-[(4-fluorobenzyl)sulfinylmethyl]-1H-indole-3-carboxylate; and
Ethyl 6-bromo-5-hydroxy-1-methyl-4-[(2-methyl-1-imidazolyl)methyl]-2-[(4-fluorobenzyl)sulfonylmethyl]-1H-indole-3-carboxylate.

11. A pharmaceutical composition, comprising the compound or racemic mixture or optical isomers or pharmaceutically acceptable salts thereof according to claim 1 as active ingredient and pharmaceutically acceptable excipient.

* * * * *

UNITED STATES PATENT AND TRADEMARK OFFICE
CERTIFICATE OF CORRECTION

| | |
|---|---|
| PATENT NO. | : 7,960,427 B2 |
| APPLICATION NO. | : 10/592619 |
| DATED | : June 14, 2011 |
| INVENTOR(S) | : Gong et al. |

It is certified that error appears in the above-identified patent and that said Letters Patent is hereby corrected as shown below:

At page 1 (Item 56) Column 1, line 23, under Other Publications, please delete "farmasevticheskii" and insert therefore --farmatsevticheskii--.

At page 1 (Item 56) Column 2, line 3, under Other Publications, please delete "farmasevticheskii" and insert therefore --farmatsevticheskii--.

At page 1 (Item 56) Column 2, line 6, under Other Publications, please delete "farmasevticheskii" and insert therefore --farmatsevticheskii--.

At page 1 (Item 56) Column 2, line 9, under Other Publications, please delete "farmasevticheskii" and insert therefore --farmatsevticheskii--.

At page 1 (Item 56) Column 2, line 11, under Other Publications, please delete "farmasevticheskii" and insert therefore --farmatsevticheskii--.

At page 1 (Item 56) Column 2, line 20, under Other Publications, please delete "farmasevticheskii" and insert therefore --farmatsevticheskii--.

At page 2 (Item 56) Column 1, line 1, under Other Publications, please delete "hepatitisu" and insert therefore --hepatitis--.

At page 2 (Item 56) Column 2, lines 6-7, under Other Publications, please delete "Curretn" and insert therefore --Current--.

At page 2 (Item 56) Column 2, line 11, under Other Publications, please delete "Targes" and insert therefore --Targets--.

At page 2 (Item 56) Column 2, line 18, under Other Publications, please delete "activites" and insert therefore --activities--.

Signed and Sealed this
Twenty-first Day of February, 2012

David J. Kappos
*Director of the United States Patent and Trademark Office*

At column 2, line 49 (approx), please delete " $-CH_2-S-(CH_2)_n-(O)_q-Ar_1$ "

and insert therefore, -- $-CH_2-S-(CH_2)_n-(O)_q-Ar_1$, --.

At column 4, line 30, please delete "heteraryl" and insert therefore, --heteroaryl--.

At column 5, line 17, please delete "heteraryl" and insert therefore, --heteroaryl--.

At column 5, line 65, please delete "Or" and insert therefore, --or--.

At column 11, line 58, please delete "heteraryl" and insert therefore, --heteroaryl--.

At column 12, line 2, please delete "heteraryl" and insert therefore, --heteroaryl--.

At column 13, line 7, please delete "racematic" and insert therefore, --racemic--.

At column 13, line 16, please delete "parainfluenze" and insert therefore, --parainfluenza--.

At column 13, line 19, please delete "constitutents" and insert therefore, --constituents--.

At column 14, line 30, please delete " $-(CH_2)_p-(O)_q-Ar_2$ "

and insert therefore, -- $-(CH_2)_p-(O)_q-Ar_2$ --.

At column 14, line 39, please delete "Nentizescu" and insert therefore, --Nenitzescu--.

At column 14, line 47, please delete "QISH" and insert therefore, --$Q_1SH$--.

At column 15, line 60, please delete "chloroacetoacetaic" and insert therefore, --chloroacetoacetic--.

At column 17, line 50, please delete "heteraryl" and insert therefore, --heteroaryl--.

At column 22, line 42 (approx), please delete "A-6;" and insert therefore, --A-6.--.

At column 28, line 18 (Table 1), please delete "(br s, 1 H)." and insert therefore, --(brs, 1 H).--.

At column 28, line 46 (Table 1), please delete "(br s, 2 H)." and insert therefore, --(brs, 2 H).--.

At column 29, line 17 (Table 1), please delete "chiorophenyl" and insert therefore, --chlorophenyl--.

At column 33, line 7 (Table 1), please delete "thiomethy]" and insert therefore, --thiomethyl]--.

At column 45, line 33 (Table 3), please delete "thiazylmethyl)sulfoolylmethy]" and insert therefore, --thiazolylmethyl)sulfonylmethyl]--.

At column 53-54, line 3 (Table 3, Structure 2), please delete

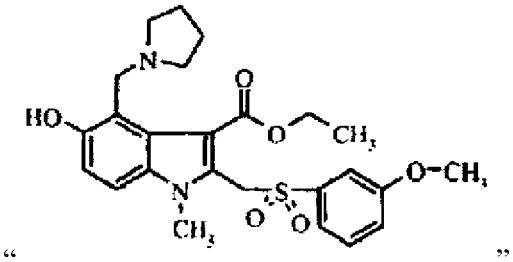

" "

and insert therefore, --

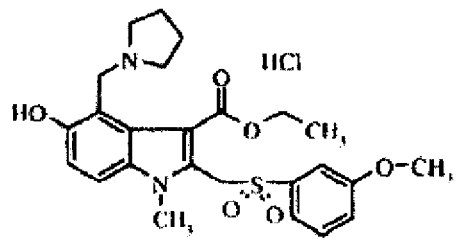

--.

At column 53-54, line 11 (Table 3), please delete "(br.s," and insert therefore, --(brs,--.

At column 53-54, line 22, please delete "furrylmethyl)" and insert therefore, --furylmethyl)--.

At column 60, line 38, please delete "arylheterocylces" and insert therefore, --arylheterocycles--.

At column 73, line 6 (Table 5), please delete "imidazoly)" and insert therefore, --imidazolyl)--.

At column 86, line 19, please delete "(brs, 1 H)." and insert therefore, --(br s, 1 H).--.

At column 86, line 23, please delete "(s, 1 H,)" and insert therefore, --(s, 1 H),--.

At column 88, line 17, please delete "(brs, 1 H)." and insert therefore, --(br s, 1 H).--.

At column 115, line 45 (approx), please delete "Ribovirin" and insert therefore, --Ribavirin--.

At column 116, line 14, please delete "Abidol" and insert therefore, --Arbidol--.

At column 116, line 15, please delete "Ribovirin" and insert therefore, --Ribavirin--.

At column 117, line 1, please delete "heteraryl" and insert therefore, --heteroaryl--.

At column 118, line 5 (approx), please delete "$—CH_2—S(=O)—(CH_2)p—(O)q—Ar_2,$"

and insert therefore, --$—CH_2—S(O_2)—(CH_2)p—(O)q—Ar_2,$--.